(12) United States Patent
Troll et al.

(10) Patent No.: US 12,065,691 B2
(45) Date of Patent: *Aug. 20, 2024

(54) RECOVERING LONG-RANGE LINKAGE INFORMATION FROM PRESERVED SAMPLES

(71) Applicant: Dovetail Genomics, LLC, Scotts Valley, CA (US)

(72) Inventors: Christopher John Troll, Santa Cruz, CA (US); Martin P. Powers, San Francisco, CA (US); Nicholas H. Putnam, Waltham, MA (US); Marco Blanchette, Santa Cruz, CA (US); Paul Hartley, San Jose, CA (US)

(73) Assignee: DOVETAIL GENOMICS, LLC, Scotts Valley, CA (US)

( * ) Notice: Subject to any disclaimer, the term of this patent is extended or adjusted under 35 U.S.C. 154(b) by 674 days.

This patent is subject to a terminal disclaimer.

(21) Appl. No.: 17/166,394

(22) Filed: Feb. 3, 2021

(65) Prior Publication Data

US 2021/0371904 A1 Dec. 2, 2021

Related U.S. Application Data

(63) Continuation of application No. 16/053,610, filed on Aug. 2, 2018, now Pat. No. 10,947,579, which is a continuation of application No. PCT/US2017/032466, filed on May 12, 2017.

(60) Provisional application No. 62/410,599, filed on Oct. 20, 2016, provisional application No. 62/336,252, filed on May 13, 2016.

(51) Int. Cl.
*C12Q 1/6806* (2018.01)
*C12Q 1/6816* (2018.01)
*C40B 40/06* (2006.01)

(52) U.S. Cl.
CPC ......... *C12Q 1/6806* (2013.01); *C12Q 1/6816* (2013.01); *C40B 40/06* (2013.01)

(58) Field of Classification Search
CPC .. C12Q 1/68; C12Q 1/6816; C12Q 2523/101; C12N 15/11; C40B 40/06
See application file for complete search history.

(56) References Cited

U.S. PATENT DOCUMENTS

| | | |
|---|---|---|
| 1,045,793 A | 11/1912 | Houdard |
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,988,617 A | 1/1991 | Landegren et al. |
| 5,143,854 A | 9/1992 | Pirrung et al. |
| 5,234,809 A | 8/1993 | Boom et al. |
| 5,242,794 A | 9/1993 | Whiteley et al. |
| 5,348,853 A | 9/1994 | Wang et al. |
| 5,476,930 A | 12/1995 | Letsinger et al. |
| 5,494,810 A | 2/1996 | Barany et al. |
| 5,567,583 A | 10/1996 | Wang et al. |
| 5,571,639 A | 11/1996 | Hubbell et al. |
| 5,593,839 A | 1/1997 | Hubbell et al. |
| 5,705,628 A | 1/1998 | Hawkins |
| 5,780,613 A | 7/1998 | Letsinger et al. |
| 5,786,146 A | 7/1998 | Herman et al. |
| 5,837,832 A | 11/1998 | Chee et al. |
| 5,989,823 A | 11/1999 | Jayasena et al. |
| 5,994,056 A | 11/1999 | Higuchi |
| 6,033,854 A | 3/2000 | Kurnit et al. |
| 6,110,709 A | 8/2000 | Ausubel et al. |
| 6,117,635 A | 9/2000 | Nazarenko et al. |
| 6,171,785 B1 | 1/2001 | Higuchi |
| 6,174,670 B1 | 1/2001 | Wittwer et al. |
| 6,225,109 B1 | 5/2001 | Juncosa et al. |
| 6,287,766 B1 | 9/2001 | Nolan et al. |
| 6,326,145 B1 | 12/2001 | Whitcombe et al. |
| 6,416,950 B1 | 7/2002 | Lohse et al. |
| 6,449,562 B1 | 9/2002 | Chandler et al. |
| 6,582,938 B1 | 6/2003 | Su et al. |

(Continued)

FOREIGN PATENT DOCUMENTS

| | | |
|---|---|---|
| AU | 2012222108 A1 | 7/2013 |
| CN | 104232616 A | 12/2014 |

(Continued)

OTHER PUBLICATIONS

Berkum et al., J. of Visualized Experiments 39:e1869 pp. 1-7 (Year: 2010).*
Simonis et al.Nature Genetics 38(11) :1348 (Year: 2006).*
Splinter et al., Methods in Enzymology 375 : 493 (Year: 2004).*
Adams, et al. The Genome Sequence of *Drosophila melanogaster.* Science Mar. 24, 2000, 287.5461: 2185-2195.
Ahlfen et al., Determinants of RNA Quality from FFPE Samples. PLOS One 12: e1261 (2007).
Bansal et al., Hapcut: an efficient and accurate algorithm for the haplotype assembly problem, Bioinformatics, 24(16): i153-i159 (Aug. 9, 2008).

(Continued)

*Primary Examiner* — Ethan C Whisenant
(74) *Attorney, Agent, or Firm* — Wilson Sonsini Goodrich & Rosati

(57) ABSTRACT

The disclosure provides methods to isolate genome or chromosome level structural information from preserved samples. In some cases, samples preserved under conditions where long-range nucleic acid information is believed to be irreparably lost, such as FFPE samples, are treated to recover nucleic acid-protein complexes stabilized as part of the sample preservation process. The complexes are processed so as to recover information regarding which nucleic acids are bound to a common complex, and the information is used to recover genomic structural information.

17 Claims, 19 Drawing Sheets

(56) References Cited

U.S. PATENT DOCUMENTS

| | | |
|---|---|---|
| 6,632,598 B1 | 10/2003 | Zhang et al. |
| 6,787,308 B2 | 9/2004 | Balasubramanian et al. |
| 6,833,246 B2 | 12/2004 | Balasubramanian |
| 6,897,023 B2 | 5/2005 | Fu et al. |
| 6,969,488 B2 | 11/2005 | Bridgham et al. |
| 7,001,724 B1 | 2/2006 | Greenfield |
| 7,361,468 B2 | 4/2008 | Liu et al. |
| 7,414,117 B2 | 8/2008 | Saito et al. |
| 7,425,415 B2 | 9/2008 | Pfeifer et al. |
| 7,709,179 B2 | 5/2010 | Iwashita |
| 7,709,197 B2 | 5/2010 | Drmanac |
| 7,901,891 B2 | 3/2011 | Drmanac |
| 7,985,546 B2 | 7/2011 | Church et al. |
| 8,058,004 B2 | 11/2011 | Oleinikov |
| 8,071,296 B2 | 12/2011 | Ruan et al. |
| 8,076,070 B2 | 12/2011 | Chen et al. |
| 8,153,373 B2 | 4/2012 | De Laat et al. |
| 8,278,112 B2 | 10/2012 | Shokat et al. |
| 8,367,322 B2 | 2/2013 | Barany et al. |
| 8,642,295 B2 | 2/2014 | De Laat et al. |
| 8,673,562 B2 | 3/2014 | Drmanac |
| 8,741,577 B2 | 6/2014 | Graneli et al. |
| 8,841,075 B1 | 9/2014 | Borner et al. |
| 9,273,309 B2 | 3/2016 | Dekker et al. |
| 9,411,930 B2 | 8/2016 | Green, Jr. et al. |
| 9,434,985 B2 | 9/2016 | Dekker et al. |
| 9,688,981 B2 | 6/2017 | Dekker et al. |
| 9,708,648 B2 | 7/2017 | Dekker et al. |
| 9,715,573 B2 | 7/2017 | Putnam et al. |
| 9,910,955 B2 | 3/2018 | Green, Jr. et al. |
| 10,066,227 B2 | 9/2018 | Dekker et al. |
| 10,089,437 B2 | 10/2018 | Green et al. |
| 10,318,706 B2 | 6/2019 | Putnam |
| 10,457,934 B2 | 10/2019 | Green et al. |
| 10,526,641 B2 | 1/2020 | Fields et al. |
| 10,529,443 B2 | 1/2020 | Green, Jr. et al. |
| 10,745,744 B2 | 8/2020 | Dekker et al. |
| 10,825,553 B2 | 11/2020 | Green, Jr. et al. |
| 10,947,579 B2 * | 3/2021 | Troll ................... C12Q 1/6816 |
| 10,975,417 B2 | 4/2021 | Green, Jr. et al. |
| 11,081,209 B2 | 8/2021 | Green, Jr. et al. |
| 11,091,758 B2 | 8/2021 | Rokhsar et al. |
| 11,326,159 B2 | 5/2022 | Rokhsar |
| 11,535,844 B2 | 12/2022 | Dekker et al. |
| 11,600,361 B2 | 3/2023 | Putnam et al. |
| 11,807,896 B2 | 11/2023 | Rice et al. |
| 2002/0012930 A1 | 1/2002 | Rothberg et al. |
| 2002/0190663 A1 | 12/2002 | Rasmussen |
| 2003/0022207 A1 | 1/2003 | Balasubramanian et al. |
| 2003/0044781 A1 | 3/2003 | Korlach et al. |
| 2003/0064398 A1 | 4/2003 | Barnes |
| 2003/0068629 A1 | 4/2003 | Rothberg et al. |
| 2003/0100102 A1 | 5/2003 | Rothberg et al. |
| 2003/0148344 A1 | 8/2003 | Rothberg et al. |
| 2003/0170689 A1 | 9/2003 | Stamatoyannapoulos et al. |
| 2003/0228627 A1 | 12/2003 | Emerson et al. |
| 2004/0106110 A1 | 6/2004 | Balasubramanian et al. |
| 2004/0197779 A1 | 10/2004 | Apffel |
| 2004/0225004 A1 | 11/2004 | Zeligs |
| 2004/0248161 A1 | 12/2004 | Rothberg et al. |
| 2005/0079510 A1 | 4/2005 | Berka et al. |
| 2005/0100932 A1 | 5/2005 | Lapidus et al. |
| 2005/0124022 A1 | 6/2005 | Srinivasan et al. |
| 2005/0130161 A1 | 6/2005 | Fraser et al. |
| 2005/0260625 A1 | 11/2005 | Wang |
| 2006/0012784 A1 | 1/2006 | Ulmer |
| 2006/0012793 A1 | 1/2006 | Harris |
| 2006/0024678 A1 | 2/2006 | Buzby |
| 2006/0024711 A1 | 2/2006 | Lapidus et al. |
| 2006/0078909 A1 | 4/2006 | Srinivasan et al. |
| 2006/0078937 A1 | 4/2006 | Korlach et al. |
| 2006/0252025 A1 | 11/2006 | Nitta et al. |
| 2006/0252061 A1 | 11/2006 | Zabeau et al. |
| 2007/0172839 A1 | 7/2007 | Smith et al. |
| 2007/0231817 A1 | 10/2007 | De Laat et al. |
| 2007/0277251 A1 | 11/2007 | Wartiovaara et al. |
| 2008/0233101 A1 | 9/2008 | Sauer |
| 2009/0011943 A1 | 1/2009 | Drmanac et al. |
| 2009/0111115 A1 | 4/2009 | Drmanac et al. |
| 2009/0186352 A1 | 7/2009 | Akoulitchev et al. |
| 2009/0191598 A1 | 7/2009 | Ruan et al. |
| 2009/0202998 A1 | 8/2009 | Schlumpberger et al. |
| 2009/0233291 A1 | 9/2009 | Chen et al. |
| 2009/0269771 A1 | 10/2009 | Schroeder |
| 2009/0298064 A1 | 12/2009 | Batzoglou et al. |
| 2010/0062947 A1 | 3/2010 | De Laat et al. |
| 2010/0081141 A1 | 4/2010 | Chen et al. |
| 2010/0093986 A1 | 4/2010 | Zwick et al. |
| 2010/0093992 A1 | 4/2010 | Cherkasov et al. |
| 2010/0130373 A1 | 5/2010 | Dekker et al. |
| 2010/0267571 A1 | 10/2010 | Watanabe et al. |
| 2011/0033854 A1 | 2/2011 | Drmanac et al. |
| 2011/0256593 A1 | 10/2011 | Hsieh et al. |
| 2011/0287947 A1 | 11/2011 | Chen et al. |
| 2011/0300537 A1 | 12/2011 | Slepnev, I |
| 2011/0306504 A1 | 12/2011 | Xiao et al. |
| 2012/0197533 A1 | 8/2012 | Nazarenko et al. |
| 2012/0302449 A1 | 11/2012 | Dong et al. |
| 2012/0330559 A1 | 12/2012 | Jiang et al. |
| 2013/0005585 A1 | 1/2013 | Anderson et al. |
| 2013/0045872 A1 | 2/2013 | Zhou et al. |
| 2013/0053254 A1 | 2/2013 | Hollander |
| 2013/0096009 A1 | 4/2013 | Dekker et al. |
| 2013/0183672 A1 | 7/2013 | De Laat et al. |
| 2013/0203605 A1 | 8/2013 | Shendure et al. |
| 2013/0259839 A1 | 10/2013 | Aharonov et al. |
| 2013/0310548 A1 | 11/2013 | Park |
| 2014/0031241 A1 | 1/2014 | Nicol et al. |
| 2014/0057799 A1 | 2/2014 | Johnson et al. |
| 2014/0141982 A1 | 5/2014 | Jacobson et al. |
| 2014/0220587 A1 | 8/2014 | Green, Jr. et al. |
| 2015/0316500 A1 | 11/2015 | Dale et al. |
| 2015/0363550 A1 | 12/2015 | Green, Jr. et al. |
| 2016/0289738 A1 | 10/2016 | Grosveld et al. |
| 2016/0305855 A1 | 10/2016 | Richardson et al. |
| 2016/0319365 A1 | 11/2016 | Saffroy et al. |
| 2017/0159109 A1 | 6/2017 | Zheng et al. |
| 2017/0276598 A1 | 9/2017 | Ikuyama |
| 2019/0143328 A1 | 5/2019 | Savran et al. |

FOREIGN PATENT DOCUMENTS

| | | |
|---|---|---|
| DE | 10149786 A1 | 7/2003 |
| DE | 10214395 A1 | 10/2003 |
| DE | 10356837 A1 | 6/2005 |
| DE | 102004009704 A1 | 9/2005 |
| DE | 102004025744 A1 | 12/2005 |
| DE | 102004025745 A1 | 12/2005 |
| DE | 102004025746 A1 | 12/2005 |
| DE | 102004025694 A1 | 2/2006 |
| DE | 102004025695 A1 | 2/2006 |
| DE | 102004025696 A1 | 2/2006 |
| EP | 0476014 A1 | 3/1992 |
| EP | 0624059 A1 | 11/1994 |
| EP | 0717113 A2 | 6/1996 |
| EP | 0728520 A1 | 8/1996 |
| EP | 1967582 A1 | 9/2008 |
| EP | 2083090 A1 | 7/2009 |
| EP | 2624059 A1 | 8/2013 |
| EP | 2811022 A1 | 12/2014 |
| GB | 2519255 A | 4/2015 |
| JP | 2016506733 A | 3/2016 |
| JP | 2019088295 A | 6/2019 |
| WO | WO-9015070 A1 | 12/1990 |
| WO | WO-9210092 A1 | 6/1992 |
| WO | WO-9309668 A1 | 5/1993 |
| WO | WO-9511995 A1 | 5/1995 |
| WO | WO-9729212 A1 | 8/1997 |
| WO | WO-9841651 A1 | 9/1998 |
| WO | WO-0014281 A2 | 3/2000 |
| WO | WO-02088382 A2 | 11/2002 |
| WO | WO-02103046 A2 | 12/2002 |
| WO | WO-03020968 A2 | 3/2003 |
| WO | WO-03031947 A2 | 4/2003 |

(56) References Cited

FOREIGN PATENT DOCUMENTS

| | | |
|---|---|---|
| WO | WO-03042657 A2 | 5/2003 |
| WO | WO-2005001113 A2 | 1/2005 |
| WO | WO-2005005655 A1 | 1/2005 |
| WO | WO-2005005657 A1 | 1/2005 |
| WO | WO-2005044836 A2 | 5/2005 |
| WO | WO-2006040550 A1 | 4/2006 |
| WO | WO-2006097320 A2 | 9/2006 |
| WO | WO-2007004057 A2 | 1/2007 |
| WO | WO-2007093819 A2 | 8/2007 |
| WO | WO-2008008845 A2 | 1/2008 |
| WO | WO-2008024473 A2 | 2/2008 |
| WO | WO-2008127281 A2 | 10/2008 |
| WO | WO-2008143903 A2 | 11/2008 |
| WO | WO-2009053039 A1 | 4/2009 |
| WO | WO-2009147386 A1 | 12/2009 |
| WO | WO-2010011774 A1 | 1/2010 |
| WO | WO-2010036323 A1 | 4/2010 |
| WO | WO-2011056872 A2 | 5/2011 |
| WO | WO-2012005595 A2 | 1/2012 |
| WO | WO-2012028737 A1 | 3/2012 |
| WO | WO-2012045012 A2 | 4/2012 |
| WO | WO-2012047726 A1 | 4/2012 |
| WO | WO-2012054873 A2 | 4/2012 |
| WO | WO-2012106546 A2 | 8/2012 |
| WO | WO-2012142531 A2 | 10/2012 |
| WO | WO-2012142611 A2 | 10/2012 |
| WO | WO-2012150317 A1 | 11/2012 |
| WO | WO-2013078470 A2 | 5/2013 |
| WO | WO-2014012010 A1 | 1/2014 |
| WO | WO-2014047561 A1 | 3/2014 |
| WO | WO-2014121091 A1 | 8/2014 |
| WO | WO-2015075196 A1 | 5/2015 |
| WO | WO-2015089243 A1 | 6/2015 |
| WO | WO-2015123588 A1 | 8/2015 |
| WO | WO-2016019360 A1 | 2/2016 |
| WO | WO-2016044313 A1 | 3/2016 |
| WO | WO-2016061517 A2 | 4/2016 |
| WO | WO-2016089920 A1 | 6/2016 |
| WO | WO-2016134034 A1 | 8/2016 |
| WO | WO-2016154540 A1 | 9/2016 |
| WO | WO-2016164313 A1 | 10/2016 |
| WO | WO-2016207647 A1 | 12/2016 |
| WO | WO-2016207653 A1 | 12/2016 |
| WO | WO-2016207661 A1 | 12/2016 |
| WO | WO-2017070123 A1 | 4/2017 |
| WO | WO-2017147279 A1 | 8/2017 |
| WO | WO-2017197300 A1 | 11/2017 |
| WO | WO-2018195091 A1 | 10/2018 |
| WO | WO-2019094636 A1 | 5/2019 |
| WO | WO-2019152543 A1 | 8/2019 |
| WO | WO-2020264185 A1 | 12/2020 |
| WO | WO-2022147129 A1 | 7/2022 |
| WO | WO-2023091592 A1 | 5/2023 |
| WO | WO-2023146922 A2 | 8/2023 |

OTHER PUBLICATIONS

Bennike et al., Comparing the proteome of snap frozen, RNAlater preserved, and formalin-fixed paraffin-embedded human tissue samples. EuPA Open Proteomics 1-: 9-18 (2016).

Bhudevi et al., Detection of bovine viral diarrhea virus in formalin fixed paraffin embedded tissue sections by real time RT-PCR (Taqman). J. of Virological Methods 109: 25-30 (2003).

Bresters et al., The duration of fixation influences the yield of HCV cDNA-PCR products from FFPE liver tissue. J. of Virological Methods 489: 267-272 (1994).

Burton, J.N. et al. Chromosome-scale scaffolding of de novo genome assemblies based on chromatin interactions. Nat. Biotechnol., 31(12):1119-1125, Dec. 2013.

Cai et al., "SATB1 packages densely looped transcriptionally active chromatin for coordinated expression of cytokine genes," Nature Genetics, 2006, vol. 38, No. 11, pp. 1278-1288.

Chapman, et al. Meraculous: de novo genome assembly with short paired-end reads. PloS one. 2011, 6.8: e23501.

Constans, A. All in the Family Scientist 13: 36 (2003).

Constans. Beyond Sanger: Toward the $1,000 Genome—The Scientist—Magazine of the Life Sciences. The Scientist. Jun. 30, 2003; 17(13):36.

Cortese, J. Array of options. Scientist. 2000, 14.11: 26.

Cortese, J. The array of today. Scientist. 2000, 14.17: 25.

Cronin et al., Measurement of Gene Expression in Archival Paraffin-Embedded Tissues. Am J. of Pathology 164(1): 35-42 (2004).

Dekker et al., "Capturing chromosome conformation," Science, 2002, vol. 295, pp. 1306-1311.

Delpech et al., DNA extraction assays from formalin fixed tissues: Paternity testing from a 3-week-old embryo. International Congress Series 1261:471-472 (2004).

Dostie et al., "Chromosome Conformation Capture Carbon Copy (5C): a massively parallel solution for mapping interaction between genomic elements," Genome research, 2006, vol. 16, No. 10, pp. 1299-1309.

Drmanac et al. Human genome sequencing using unchained base reads on self-assembling DNA nanoarrays. Science. 327: 78-81 (2010).

Ekins, R. et al. Microarrays: Their Origins and applications. Trends in Biotechnology, 17(6); 217-218 (Jun. 1999).

Fan et al. "A versatile assay for high-throughput gene expression profiling on universal array matrices." Genome Research, 2004, vol. 14 No. 5 pp. 878-885.

Fangman, et al. Activation of replication origins within yeast chromosomes, Annual Review of Cell Biology, 7(1); 375-402 (1991).

Fodor, et al. Light-directed, spatially addressable parallel chemical synthesis. Science. Feb. 15, 1991, 251.4995: 767-773.

Fyodorov, et al. Chromatin assembly in vitro with purified recombinant ACF and NAP-1. Methods in enzymology. 2002, 371: 499-515.

Garaj, et al. Graphene as a sub-nanometer trans-electrode membrane. Nature. Sep. 9, 2010, 467.7312: 190-193 . . . .

Gilmour, David S., et al. Detecting protein-DNA interactions in vivo: distribution of RNA polymerase on specific bacterial genes. Proceedings of the National Academy of Sciences. (1984) 81(14): 4275-4279.

Gwynne, P. et al. Microarray analysis: the next revolution in molecular biology. Science. pp. 1-6 (Aug. 6, 1999).

Han et al., Trypsin and Reduction Method to Prepare DNA from FormalinFixed and Paraffin Embedded Samples for Methylation Analysis. Histopathology 54(6): 773-775 (2009).

Heid, C.A. et al. Real time quantitative PCR. Genome Research, 6(10): 986-994 (1996).

Herschleb, J. et al. Pulsed-field gel electrophoresis. Pulsed-field gel electrophoresis. Nature Protocols 2(3):677-84 (Mar. 29, 2007).

Jansen, et al. Nucleosome Positioning in *Saccharomyces cerevisiae*. Microbiology and Molecular Biology Reviews, Jun. 2011, pp. 301-320.

Kalhor, R., et al. Genome architectures revealed by tethered chromosome conformation capture and population-based modeling. Nat. Biotechnol., 30(1):90-98, Jan. 2012.

Kaplan, et al. Nat. Biotechnol. 2013, 31: 1139-1143.

Karmakar et al., Organocatalytic Removal of Formaldehyde Adducts from RNA and DNA Bases. Nature Chemistry 7(9): 752-758 (2015).

Kawashima et al., Efficient extraction of proteins from FFPE tissues concentration of tris(hydroxymethyl)aminomethane. Clinical Proteomics 11(4): 2-6 (2014).

Kitzman, Jacob O. et al. Haplotype-resolved genome sequencing of a Gujarati Indian individual, Nature Biotechnology, 29(1): 59-63 (Jan. 2011).

Kundu et al. Activator-dependent transcription from chromatin in vitro involving targeted histone acetylation by p300. Molecular cell. 2000, 6.3: 551-561.

Kuo et al. In Vivo Cross-Linking and Immunoprecipitation for Studying Dynamic Protein: DNA Associations in a Chromatin Environment. Methods 19:425-433 (1999).

Lasken, Roger S. et al. Mechanism of chimera formation during the Multiple Displacement Amplification reaction. BMC biotechnology. 7(19):1-11 (Apr. 12, 2007).

(56) References Cited

OTHER PUBLICATIONS

Lemieux, B. et al. Overview of DNA chip technology. Molecular Breeding 4: 277-289 (1998).
Levene, et al. Zero-mode waveguides for single-molecule analysis at high concentrations. Science. Jan. 31, 2003;299(5607):682-6.
Lieberman-Aiden, et al. "Comprehensive mapping of long range interactions reveals folding principles of the human genome." Science. Oct. 9, 2009; 326(5950): 289-293. doi: 10.1126/science.1181369.
Lin et al., High-quality genomic DNA extraction from formalin-fixed and paraffin-embedded samples deparaffinized using mineral oil. Anal Biochem 395(2):265-267 (2009).
Lupski, James R. et al. Whole-genome sequencing in a patient with Charcot-Marie-Tooth neuropathy. New England Journal of Medicine, 362(13): 1181-1191 (Apr. 1, 2010).
Lusser, Alexandra et al. Strategies for the reconstitution of chromatin. Nature Methods, 1(1):19-26 (Oct. 2004).
Ma, H. et al. Application of Real-time Polymerase Chain Reaction (RT-PCR), The Journal of American Science, 2 (3):1-15 (Aug. 10, 2006).
Macabeo-Ong et al., Effect of Duration of Fixation on Quantitative Reverse Transcription PCR Analyses. Modern Pathology 15(9): 979-987 (2001).
Maniatis, et al. Molecular Cloning: A Laboratory Manual, Cold Spring Harbor, N.Y., pp. 280-281 (1982).
Margulies, M. et al. Genome sequencing in open microfabricated high density picolitre reactors. Nature 437(7057):376-380 (Sep. 15, 2005).
Marshall, A. et al. DNA chips: an array of possibilities. Nature Biotechnology, 16(1): 27-31 (Jan. 1998).
Mary, I. et al. Metaproteomic and metagenomic analyses of defined oceanic microbial populations using microwave cell fixation and flow cytometric sorting. FEMS Microbiol Ecol. 74(1):10-18 (Oct. 2010). E-Pub. Jul. 5, 2010.
Masuda et al., Analysis of chemical modification of RNA from formalin-fixed samples and optimization of molecular biology applications for such samples. Nucleic Acids Research 27(22):4436-4443 (1999).
Nazarenko, I.A. et al. A closed tube format for amplification and detection of DNA based on energy transfer. Nucleic acids research, 25(12):2516-2521 (Jun. 15, 1997).
Nelson et al. Protocol for the fast chromatin immunoprecipitation (ChIP) method. Nature Protocols 1(1):179-185 (2006).
Oliveira et al. Translocation capture sequencing: A method for high throughput mapping of chromosomal rearrangements. J. of Immunological Methods 375:176-181 (2012).
Orlando. Mapping chromosomal proteins in vivo by formaldehydecrosslinked-chromatin immunoprecipitation. TIBS 25:99-104 (2000).
Park. ChIP-seq: advantages and challenges of a maturing technology. Nature Reviews Genetics vol. 10, pp. 669-680 (2009) . . . .
PCT/US2014/014184 International Preliminary Report on Patentability dated Aug. 13, 2015.
PCT/US2014/014184 International Search Report dated Apr. 23, 2014.
Peng, Z. et al. Generation of long insert pairs using a Cre-LoxP Inverse PCR approach, PLoS One, 7(1): e29437 (2012) E-Pub Jan. 9, 2012.
Peters, B.A. et al. Accurate whole-genome sequencing and haplotyping from 10 to 20 human cells. Nature, 487(7406):190-195 (Jul. 11, 2012).
Potluri et al., Genomic DNA extraction methods using FFPE tissue. Analytical Biochemistry 486: 17-23 (2015).
Rios, J. et al. Identification by whole-genome resequencing of gene defect responsible for severe hypercholesterolemia. Human Molecular Genetics, 19(22): 4313-4318 (Nov. 15, 2010). E-Pub Aug. 18, 2010).
Rodriguez et al., DNA extraction from formalin fixed franciscana tissues. Latin American Journal of Aquatic Mammals 1(1):123-128 (2000).
Sambrook, et al. Mixed Oligonucleotide-primed Amplification of cDNA (MOPAC). Cold Spring Harbor Protocols, pp. 1-30 (2006).
Sato et al., Comparison of the DNA Extraction Methods for PCR Amplification from FFPE Tissues. Diagnostic Molecular Pathology 10(4): 265-271 (2001).
Schena M. (ed.), Microarray Biochip Technology (2000), ISBN-10: 1881299376 ISBN-13: 978-1881299370.
Schena, M. et al. PCR applications: protocols for functional genomics. Chapter 28: Parallel analysis with biological chips. Eds. Michael A. Innis, David H. Gelfand, John J. Sninsky. Academic Press. ISBN: 0-12-372185-7. pp. 445-456 (1999) .
Schena, Mark et al. Genes, genomes, and chips. DNA microarrays: A practical approach. Oxford University Press, pp. 1-18 (1999); ISBN-10: 1881299376 ISBN-13: 978-1881299370.
Schwartz, D.C. et al. Separation of yeast chromosome-sized DNAs by pulsed field gradient gel electrophoresis. Cell 37(1): 67-75 (May 1984).
Selvaraj et al. Whole-genome haplotype reconstruction using proximity-ligation and shotgun sequencing. Nat. Biotechnol. 2013, 31:1113-1119.
Sewards, Richard, Combined Search and Examination Report under Sections 17 & 18(3), Great Britain Patent Application No. GB1520448.0, Date of Report: May 31, 2016.
Shalon, D. et al. A DNA microarray system for analyzing complex DNA samples using two-color fluorescent probe hybridization. Genome research, 6(7): 639-645 (Jul. 1996).
Simpson, J.T. et al. Efficient de novo assembly of large genomes using compressed data structures. Genome Res, 22(3): 549-556 (Mar. 2012). E-Pub Dec. 7, 2011. doi: 10.1101/gr.126953.111.
Solomon, M.J. et al. Formaldehyde-mediated DNA-protein crosslinking: a probe for in vivo chromatin structures. Proceedings of the National Academy of Sciences, 82(19): 6470-6474 (Oct. 1985).
Solomon, M.J. et al. Mapping protein-DNA interactions in vivo with formaldehyde: evidence that histone H4 is retained on a highly transcribed gene. Cell, 53(6):937-947 (Jun. 17, 1988).
Soni, et al. Progress toward ultrafast DNA sequencing using solid-state nanopores. Clin Chem, 53(11):1996-2001 (Nov. 2007). Epub Sep. 21, 2007.
Srinivasan et al., Effect of fixatives and tissue processing on the content and integrity of nucleic acids. Am. J. of Pathology 161(16): 1961 (2002).
Tanizawa, H. et al., Mapping of long-range associations throughout the fission yeast genome reveals global genome organization linked to transcriptional regulation. Nucleic Acid Research, 38(22):8164-8177 (Dec. 2010). Epub Oct. 28, 2010.
Teague, B. et al. High-resolution human genome structure by single-molecule analysis. Proceedings of the National Academy of Sciences, 107(24): 10848-10853 (Jun. 15, 2010).
Thavarajah et al. Chemical and physical basics of routine formaldehyde fixation. J. of Maxxillo facial Pathology 16(3):400-405 (2012).
Thavarajah et al., Chemical and physical basics of routine formaldehyde fixation. J. of Oral and Maxillofac Pathology 16(3): 400-405 (2012).
The Definition of "N50" from Metagenomics. Printed on Jun. 4, 2020.
Tyagi, S. et al. Molecular beacons: probes that fluoresce upon hybridization. Nature Biotechnology, 14(3):303-308 (Mar. 1996).
Umbarger, M.A. Chromosome conformation capture assays in bacteria. Methods 58(3):212-220 (Nov. 2012).
U.S. Appl. No. 16/053,610 Non-Final Office Action dated Dec. 20, 2018.
U.S. Appl. No. 16/128,297 Non-Final Office Action dated Nov. 18, 2020.
U.S. Appl. No. 15/561,447 Final Office Action dated Jun. 10, 2020.
U.S. Appl. No. 15/561,447 Non-Final Office Action dated Jan. 31, 2020.
U.S. Appl. No. 16/053,610 Office Action dated May 1, 2019.
Van Beers et al., A multiplex PCR predictor for aCGH success of FFPE samples. Br. J. of Cancer 94: 333-337 (2006).
Venter, J.C. et al. The sequence of the human genome. Science, 291(5507):1304-1351 (Feb. 16, 2001).

(56) References Cited

OTHER PUBLICATIONS

Werner et al., Effect of Formalin Tissue Fixation and Processing on Immunohistochemistry. Am J. of Surgical Pathology 24(7): 1016-1019 (2000).
Whitcombe, D. et al. Detection of PCR Products Using Self-probing Amplicons and Fluorescence. Nature Biotechnology, 17(8):804-807 (Aug. 1999).
Wing, R.D., et al. An improved method of plant megabase DNA isolation in agarose microbeads suitable for physical mapping and YAC cloning. The Plant Journal, 4(5):893-898 (1993).
Zhou, S. et al. A single molecule scaffold for the maize genome. PLoS Genetics, 5(11):e1000711; pp. 1-14 (Nov. 20, 2009).
Abecasis et al., A map of human genome variation from population-scale sequencing (1000 Genomes Project Consortium). Nature . 467(7319):1061-1073 (2010).
Adey et al., In vitro, long-range sequence information for 19 de novo genome assembly via transposase contiguity. Genome Res. 24(12):2041-2049 (2014).
Alkan et al., Genome structural variation discovery and genotyping. Nat Rev Genet. 12(5):363-376 (2011).
Alkan et al., Limitations of next-generation genome sequence assembly. Nat. Methods. 8(1):61-65 (2011).
Allison, Recombinant DNA technology and molecular cloning, Ch. 8:180-231. Fundamental Molecular Biology. Wiley-Blackwell (2007).
Altschul et al., Gapped BLAST and PSI-BLAST: A New Generation of Protein Database Search Programs. Nucleic Acids Research 25(17):3389-3402 (1997).
Amini et al., Haplotype-resolved whole-genome sequencing by contiguity-preserving transposition and combinatorial indexing. Nat Genet. 46(12):1343-1349 (2014).
Belton et al. Hi-C: a comprehensive technique to capture the conformation of genomes. Methods 58(3):268-276 (2012).
Blander, G. et al.SIRT1 Shows No Substrate Specificity in Vitro. Journal of biological Chemistry. 280:9780-9785 (2005).
Blecher-Gonen et al., High-throughput chromatin immunoprecipitation for genome-wide mapping of in vivo protein-DNA interactions and epigenomic states. Nature Protocols, 8(3):539-554 (2013).
Bolger et al., Trimmomatic: a flexible trimmer for Illumina sequence data. Bioinformatics, 30(15):2114-2120 (2014).
Bradnam et al., Assemblathon 2: evaluating de novo methods of genome assembly in three vertebrate species. Gigascience, 2(1):10, pp. 1-30 (2013).
Cleveland et al., Centromeres and kinetochores: from epigenetics to mitotic checkpoint signaling. Cell. 112(4):407-421 (2003).
De Koning et al., Repetitive elements may comprise over two-thirds of the human genome. PLoS Genet., 7(12):e1002384, pp. 1-12 (2011).
Dejica et al. Cleavage of type II collagen by cathepsin K in human osteoarthritic cartilage. Am J Pathol. 173(1):161-169 (2008).
Dekker et al., A closer look at long-range chromosomal interactions. Trends in Biochemical Science (Jun. 2003) 28(6):277-280.
Dekker et al., Exploring the three-dimensional organization of genomes: interpreting chromatin interaction data. Nat Rev Genet. 14(6):390-403 (2013).
Delaneau et al., Shape-IT: new rapid and accurate algorithm for haplotype inference. BMC Bioinformatics. 16:9:540, pp. 1-14 (2008).
Dixon et al., Topological domains in mammalian genomes identified by analysis of chromatin interactions. Nature, 485(7398):376-380 (2012).
Dower, et al. Recombinant and synthetic randomized peptide libraries. Ann. Rep. Med. Chem. 26:271-280 (1991).
Duitama et al., Fosmid-based whole genome haplotyping of a HapMap trio child: evaluation of single individual haplotyping techniques. Nucleic Acids Res. 40(5):2041-2053 (2012).
Eisenstein, Oxford Nanopore announcement sets sequencing sector abuzz. Nat Biotechnol. 30(4): 295-296 (2012).
Enoiu et al., Repair of cisplatin-induced DNA interstand crosslinks by a replication-independent pathway involving transcription-coupled repair and translesion synthesis. Nucleic Acids Research, 40(18):8953-8964 (2012).
Fang et al., Mapping of long-range chromatin interactions by proximity ligation-assisted ChIP-seq. Letter to the Editor—Cell Research 26: 1345-1348 (2016).
Ferraiuolo et al., From cells to chromatin: capturing snapshots of genome organization with 5C technology. Methods. 58(3):255-267 (2012).
Flot et al., Contact genomics: scaffolding and phasing (meta) genomes using chromosome 3D physical signatures. FEBS Letters 589(20 Pt A):2966-2974 (2015).
Fullwood, et al. An oestrogen-receptor-alpha-bound human chromatin interactome. Nature. Nov. 5, 2009;462(7269):58-64. doi: 10.1038/nature08497.
Fullwood et al. ChIP-based methods for the identification of long-range chromatin interactions. J Cell Biochem. 107(1):30-39 (2009).
Fullwood, et al. Next Generation DNA sequencin of paired-end tags (PET) for transcriptome and genome analyses. Genome Research. 19(4):521-532 (Apr. 2009).
Fullwood et al., Chromatin interaction analysis using paired-end tag sequencing. Jan. 2010. Curr. Prot. In Mol. Biol. Chapter 21; unit 21 .15.1-25 . . . .
Garstecki et al., Formation of bubbles and droplets in microfluidic systems. Technical sciences 53(4): 69 (2005).
GE Healthcare: Instructions 71-7106-00AF Activated Thiol Sepharose 4B (pp. 1-12) (Jul. 2008).
Gish et al. Identification of protein coding regions by database similarity search. Nature Genetics 3:266-272 (1993).
Gnerre et al., High-quality draft assemblies of mammalian genomes from massively parallel sequence data. Proc. Natl. Acad. Sci. U.S.A., 108 (4):1513-1518, Jan. 2011.
Goodwin et al., Oxford nanopore sequencing and de novo assembly of a eukaryotic genome. bioRxiv, pp. 1-28 (Jul. 15, 2015).
Green et al., Three crocodilian genomes reveal ancestral patterns of evolution among archosaurs. Science. 346(6215):1254449, pp. 1-11 (2014).
Grunenwald et al., Rapid, high-throughput library preparation for next-generation sequencing. Nature Methods. Volume 7, iii-iv (2010).
Haussler, D., et al. Genome 10K: a proposal to obtain whole-genome sequence for 10,000 vertebrate species. J. Hered., 100(6):659-674, 2009.
Hesselberth et al., Global mapping of protein-DNA interactions in vivo by digital genomic footprinting. Nat Methods 6(4):283-289 (2009).
Higashi-Fujime S, et al. Muscle actin cleaved by proteinase K: its polymerization and in vitro motility. J Biochem. 112(4):568-572 (1992).
Hsieh et al., Mapping nucleosome resolution chromosome folding in yeast by Micro-C. Cell. 162(1):108-119 (2015).
Juric et al., MAPS: Model-based analysis of long-range chromatin interactions from PLAC-seq and HiChIP experiments. PLoS Comput Biol. 15(4):e1006982, pp. 1-24 (2019).
Kidd et al., Mapping and sequencing of structural variation from eight human genomes. Nature, 453(7191):56-64 (2008).
Kitzman et al., Haplotype-resolved genome sequencing of a Gujarati Indian individual, Nature Biotechnology, 2011, 29(1): 59-63.
Korbel et al., Genome assembly and haplotyping with Hi-C. Nat Biotechnol. 31(12):1099-1101 (2013).
Koren et al., Reducing assembly complexity of microbial genomes with single-molecule sequencing. Genome Biol. 14(9):R101, pp. 1-16 (2013).
Koren et al., Hybrid error correction and de novo assembly of single-molecule sequencing reads. Nature biotechnology, 30(7):693-700, 2012.
Kotoulas et al., Adaptive routing in structured peer-to-peer overlays. In: 3rd Intl. IEEE workshop (COPS workshop at WETICE07), 6pages (2007). Available at https://citeseerx.ist.psu.edu/document?repid=rep1&type=pdf&doi=4cf1f4ff43917d7008caac61ddf3fb8d0f9feb94 NPL_LIU-COPE-an-accurate-2012.
Krietenstein et al., Ultrastructural details of mammalian chromosome architecture. bioRxiv preprint 639922, pp. 1-15 (2019). https://www.biorxiv.org/content/10.1101/639922v1http://dx.doi_org/10.1101/639922.

(56) References Cited

OTHER PUBLICATIONS

Lee et al. Chromatin immunoprecipitation and microarray-based analysis of protein location, Nature Protocols 1(2): 729-748 (2006).
Li et al., De novo assembly of human genomes with massively parallel short read sequencing. Genome Res. 20(2):265-272 (2010).
Li et al., OCEAN-C: mapping hubs of open chromatin interactions across the genome reveals gene regulatory networks. Genome Biol. 19(1):54, pp. 1-14 (2018).
Liu et al., COPE: an accurate k-mer-based pair-end reads connection tool to facilitate genome assembly. Bioinformatics, 28(22): 2870-2874 (2012).
Ma et al., Fine-scale chromatin interaction maps reveal the cis-regulatory landscape of human lincRNA genes. Nat Methods. 12(1):71-78 (2015).
Ma et al., Using DNase Hi-C techniques to map global and local three-dimensional genome architecture at high resolution. bioRxiv preprint184846, pp. 1-55 (2018). Available at doi: https://doi.org/10.1101/184846.
Madden et al. Applications of network BLAST server. Methods Enzymol. 266:131-141 (1996).
Marie-Nelly et al., High-quality genome (re)assembly using chromosomal contact data. Nature Communications 5:5695, pp. 1-10 (2014).
Melters et al., Comparative analysis of tandem repeats from hundreds of species reveals unique insights into centromere evolution. Genome Biol. 14(1):R10, pp. 1-20 (2013).
Meyer et al., Illumina sequencing library preparation for highly multiplexed target capture and sequencing. Cold Spring Harb Protoc, 2010(6):pdb.prot5448 pp. 1-21 (2010).
Mifsud et al., Mapping long-range promoter contacts in human cells with high-resolution capture Hi-C. Nat Genet. 47(6):598-606 (2015).
Miller et al. A Simple salting out procedure for extracting DNA from human nucleated cells. Nucleic Acids Res. 16(3):1215 (1988).
Mornet et al., Proteolysis and the domain organization of myosin subfragment 1. Proc Natl Acad Sci USA. 81(3):736-739 (1984).
Morrison et al., Retinoblastoma Protein Transcriptional Repression through Histone Deacetylation of a Single Nucleosome.Molecular and Cellular biology 22(3):856-865 (2002).
Myers et al., A Whole-Genome Assembly of *Drosohila*. Science, 287(5461):2196-2204 (2000).
Nagaki et al., Chromatin immunoprecipitation reveals that the 180-bp satellite repeat is the key functional DNA element of *Arabidopsis thaliana* centromeres. Genetics. 163(3):1221-1225 (2003).
Nature Genetics: The chipping forecast (Ed. Phimister et al.). Special supplement to Nature Genetics vol. 21, pp. 1-6 (1999). Available at https://www.nature.com/collections/lsggkwfybr.
Nickerson et al., The nuclear matrix revealed by eluting chromatin from cross-linked nucleus. Proc. Natl. Acad. Sci 94:4446-4450 (1997).
O'Neill LP, Turner BM. Immunoprecipitation of native chromatin: NChIP. Methods. Sep. 2003;31(1):76-82.
PCT/US2017/032466 International Search Report and Written Opinion Mailed Aug. 22, 2017.
Putnam et al., Chromosome-scale shotgun assembly using an in vitro method for long-range linkage. Genome Res. 26(3):342-350 (2016).
Putnam et al., Supplemental Material—Chromosome-scale shotgun assembly using an in vitro method for long-range linkage. Genome Research 26:342-350 (2016).
Putnam et al., Chromosome-scale shotgun assembly using an in vitro method for long-range linkage. arXiv:1502.05331[q-bio.GN] pp. 1-25. Feb. 18, 2015 (Retrieved from the Internet Oct. 8, 2015).
Quail, M.A. et al. A tale of three next generation sequencing platforms: comparison of Ion Torrent, Pacific Biosciences and Illumina MiSeq sequencers. BMC Genomics, 13:341 (2012).
Ramani et al., Mapping 3D genome architecture through in situ DNase Hi-C. Nat Protoc. 11(11):2104-2121 (2016).
Ramani, et al. Massively multiplex single-cell Hi-C. Nat Methods. 14(3): 263-266 (2017).
Rao et al., A 3D map of the human genome at kilobase resolution reveals principles of chromatin looping. Cell. 159:1665-1680 (2014).
Riley et al., Rapid whole genome optical mapping of *Plasmodium falciparum*. Malar J. 10:252, pp. 1-8 (2011).
Rozowsky et al. AlleleSeq: analysis of allele-specific expression and binding in a network framework. Mol. Syst. Biol., 7:522; pp. 1-15 (2011).
Salzberg et al., GAGE: A critical evaluation of genome assemblies and assembly algorithms. Genome Res., 22(3):557-567 (2012).
Sambrook et al., Mixed Oligonucleotide-primed Amplification of cDNA (MOPAC). Cold Spring Harbor Protocols 2006(1):pdb.prot3484, 2006.
Schloss et al., A statistical toolbox for metagenomics: assessing functional diversity in microbial communities, BMC Bioinformatics 9(34):1-15 (2008).
Schmidt et al., ChIP-seq: using high-throughput sequencing to discover protein-DNA interactions. Methods 48(3): 240-248 (2009).
Schutze et al., A calibrated diversity assay for nucleic acid libraries using DiStRO—a Diversity Standard of Random Oligonucleotides. Nucleic Acids Res. 38(4):e23, pp. 1-5 (2010).
Selvaraj, S. et al. Complete haplotype phasing of the MHC and KIR loci with targeted HaploSeq. BMC Genomics 16:900, pp. 1-7 (2015).
Sexton et al., Sensitive detection of chromatin coassociations using enhanced chromosome conformation capture on chip. Nature Protocols. 7(7):1335-1350 (2012).
Shedlock et al., Phylogenomics of nonavian reptiles and the structure of the ancestral amniote genome. Proc. Natl. Acad. Sci. U.S.A. 104(8):2767-2772 (2007).
Sheridan, Milestone approval lifts Illumina's NGS from research into clinic. Nature Biotechnology, 32(2):111-112 (2014).
Shiio et al., Quantitative proteome analysis using isotope-coded affinity tags and mass spectrometry. Nature Protocols, 1(1): 139-145 (2006).
Sigma Protein A immobilized product sheet (Published Mar. 2001) accessed on Apr. 14, 2016.
Slotkin et al., Transposable elements and the epigenetic regulation of the genome. Nat Rev Genet. 8(4):272-285 (2007).
Splinter, 3C Technology: Analyzing the Spatial Organization of Genomic Loci In Vivo Methods in Enzymology, 375:493-507 (2004).
Stadhouders et al., Multiplexed chromosome conformation capture sequencing for rapid genome-scale high-resolution detection of long-range chromatin interactions. Nature Protocols. 8(3):509-524 (2013). . . . .
Stankiewicz et al., Structural variation in the human genome and its role in disease. Annu Rev Med. 61:437-455 (2010).
Stephens et al., Complex landscapes of somatic rearrangement in human breast cancer genomes. Nature. 462(7276):1005-1010 (2009).
Storek et al., High-resolution footprinting of sequence-specific protein-DNA contacts, Nature Biotechnology, 20(2):183-186 (2002).
Syed, F. et al. Optimized library preparation method for next-generation sequencing. Application Note Abstract, Nature Methods 6:i-ii (2009).
Tewhey et al., The importance of phase information for human genomics. Nat Rev Genet. 12(3):215-223 (2011).
Torjesen, Genomes of 100,000 people will be sequenced to create an open access research resource. BMJ, 347:f6690, pp. 1-2 (2013).
Treangen et al., Repetitive DNA and next-generation sequencing: computational challenges and solutions. Nat Rev Genet. 13(1):36-46 (2011).
Troll et al. Structural Variation Detection by Proximity Ligation from Formalin-Fixed, Paraffin-Embedded Tumor Tissue. J Mol Diagn. 21(3):375-383 (2019).
Tucker et al., Massively parallel sequencing: the next big thing in genetic medicine. Am J Hum Genet. 85(2):142-154 (2009).
Tuzun et al. Fine-scale structural variation of the human genome. Nat. Genet., 37(7):727-732 (Jul. 2005).
Tyagi S, et al. Molecular beacons: hybridization probes for detection of nucleic acids in homogeneous solutions. In: Kessler, C. (eds) Nonradioactive Analysis of Biomolecules. Springer Lab Manuals. Springer, Berlin, Heidelberg. 2000.

(56) References Cited

OTHER PUBLICATIONS

U.S. Appl. No. 16/053,610 Non-Final Office Action dated May 12, 2020.
U.S. Appl. No. 17/166,394 Non-Final Office Action dated Oct. 3, 2023.
Vogelstein, et al. Cancer genome landscapes. Science 339(6127):1546-58 (2013).
Voskoboynik, A. et al. The genome sequence of the colonial chordate, Botryllus schlosseri. eLife, 2:e00569, pp. 1-24 (2013).
Wang et al., The 3D Genome Browser: a web-based browser for visualizing 3D genome organization and long-range chromatin interactions. Genome Biol. 19(1):151, pp. 1-12 (2018).
Weisenfeld N.I., et al. Comprehensive variation discovery in single human genomes. Nat. Genet. 46(12):1350-1355 (Dec. 2014) . . . .
Williams et al., Amplification of complex gene libraries by emulsion PCR. Nature Methods. 3(7):545-550 (2006).
Williams et al., Paired-end sequencing of Fosmid libraries by Illumina. Genome Res. 22(11):2241-2249 (2012).
Wu et al., Long-span, mate-pair scaffolding and other methods for faster next-generation sequencing library creation. Nat. Methods. i-ii (Sep. 2012).
Wu et al., Stability of Genomic DNA at Various Storage Conditions. Annual ISBER Conference. 1 page (2009).
Wu et al. GMAP: a genomic mapping and alignment program for mRNA and EST sequences. Bioinformatics, 21(9):1859-1875 (2005).
Xie et al., A novel motif in telomerase reverse transcriptase regulates telomere repeat addition rate and processivity. Nucleic Acids Res. 38(6):1982-1996 (2010).
Xie et al. De Novo Plant Genome Assembly Based on Chromatin Interactions: A Case Study of *Arabidopsis thaliana.* Mol Plant 8(3):489-92 (2015).
Zhang, et al. A greedy algorithm for aligning DNA sequences. J Comput Biol. 7(1-2):203-214 (2000).
Zhang, J. et al. PowerBLAST: A New Network BLAST Application for Interactive or Automated Sequence Analysis and Annotation Genome Res., vol. 7, pp. 649-656, (1997).
Zinchenko, A. et al. Compaction of Single-Chain DNA by Histone-Inspired Nanoparticles. Physical Review Letters, 95(22); 228101 (2005).

\* cited by examiner

RECOVERING LONG-RANGE LINKAGE INFORMATION FROM PRESERVED SAMPLES

CROSS-REFERENCE

This application is a continuation of U.S. patent application Ser. No. 16/053,610, filed Aug. 2, 2018, which is a continuation of International Patent Application PCT/US2017/032466, filed May 12, 2017, which claims benefit of U.S. Provisional Patent Application No. 62/336,252, filed May 13, 2016, and U.S. Provisional Patent Application No. 62/410,599, filed Oct. 20, 2016, each of which is hereby incorporated by reference in its entirety.

GOVERNMENT SUPPORT

This invention was made with government support under R43HG008847 awarded by the National Institutes of Health. The government has certain rights in the invention.

BACKGROUND

It remains difficult in theory and in practice to produce high-quality, highly contiguous genome sequences. This problem is compounded when one attempts to recover genome sequences, phasing information, or other genetic information is desired from preserved samples such as formalin-fixed, paraffin-embedded (FFPE) samples. FFPE samples are the most common banked clinical and cancer sample type. However, the fixation and embedding steps, as well as additional factors such as dehydration and long term storage, are thought to lead to DNA damage. Additional DNA damage and fragmentation may occur during DNA extraction procedures, which often include overnight proteinase K treatment and boiling to reverse crosslinking. Typical DNA fragment lengths post-extraction are less than 500 base pairs, and often less than 300 base pairs.

SUMMARY

Provided herein are methods of obtaining genome structural information from preserved samples, such as samples stored pursuant to a surgical excision or archived pursuant to a drug trial. Some such methods comprise obtaining a preserved sample from a subject, the sample comprising nucleic acids; and deriving genomic structural information by analyzing the nucleic acids in the sample. In some cases, the preserved sample is crosslinked for example using at least one of a formaldehyde, a formalin, UV light, mitomycin C, nitrogen mustard, melphalan, 1,3-butadiene diepoxide, cis diaminedichloroplatinum(II) and cyclophosphamide. Alternatively, the preserved sample is crosslinked using formalin. Often, the preserved sample maintains positional information as to nucleic acids within it. Optionally, the preserved sample is an embedded sample such as a formalin fixed paraffin-embedded (FFPE) sample. The genomic structural information is sufficient to be indicative of at least one of an inversion, an insertion, a deletion, and a translocation relative to a reference genome, if present in the sample genome. A number of reference genomes are consistent with the disclosure herein, such as a wild type genome of a species common to the subject, or a genome obtained from a reference tissue of the subject. Methods often comprise deriving information indicative of phase status for a first segment and a second segment of the nucleic acids. Optionally, the methods comprise tagging exposed nucleic acid ends of the sample so as to convey physical linkage information. In some cases, the tagging comprises ligating oligonucleotides to a DNA protein complex released from the preserved sample such that the oligonucleotides convey information indicative of a common complex. The oligonucleotides comprise base sequence specific to a complex or unique to a complex. Alternately, in preferred embodiments the tagging comprises ligating a first nucleic acid segment of the complex to a second segment of the complex to form a paired end molecule. In these cases, some methods comprise sequencing a portion of the first nucleic acid segment and a portion of the second nucleic acid segment. Contigs having unique sequence common to the portion of the first nucleic acid segment and contigs having unique sequence common to the portion of the second nucleic acid segment are assigned to a common scaffold in a nucleic acid assembly. Some methods comprise contacting the paired end nucleic acid molecule to a set of probes, such as antibodies or nucleic acid probes that are fluorescent probes or capable of supporting amplification, and that anneal to a first locus and a second locus implicated in a genome structural rearrangement. Often, the first locus and the second locus are not adjacent in a genome unaffected by the genome structural rearrangement. Alternately, the first locus and the second locus are adjacent in a genome unaffected by the genome structural rearrangement. Optionally, the method comprises sequencing nucleic acids of the sample when contacting the set of probes indicates a rearrangement. Some methods comprise contacting the paired end nucleic acid molecule to a set of probes that comprises nucleic acid primers. In some cases, the set of nucleic acid primers anneal to a first locus and a second locus implicated in a genome structural rearrangement. In these cases, the set of nucleic acid primers yield an amplicon in a nucleic acid amplification reaction when the first locus and the second locus form a ligated paired end molecule. Similarly, in some cases, the set of nucleic acid primers do not yield an amplicon in a nucleic acid amplification reaction when the first locus and the second locus do not form a ligated paired end molecule. In some cases, the first locus and the second locus are not adjacent in a genome unaffected by the genome structural rearrangement. Alternatively, the first locus and the second locus are adjacent in a genome unaffected by the genome structural rearrangement. Some embodiments optionally comprise sequencing nucleic acids of the sample when an amplicon is generated from the set of nucleic acid primers contacted to the paired end nucleic acid molecule. Preferably, the preserved tissue sample is treated to isolate nucleic acids such that protein DNA complexes are not destroyed. In some cases, the protein DNA complexes are isolated such that a first nucleic acid segment and a second nucleic acid segment are held together independent of a phosphodiester backbone. In some cases, the preserved tissue sample is treated by contacting the preserved tissue sample to xylene. In some cases, the preserved tissue sample is treated by contacting the preserved tissue sample to ethanol. In some cases, the preserved tissue sample is treated by protecting the sample from boiling conditions. In some cases, the preserved tissue sample is treated by contacting the preserved tissue sample to at least one of an anthranilate and a phosphanilate. In some cases, the preserved tissue sample is treated at a temperature not greater than 40° C. Optionally, the DNA protein complexes comprise chromatin. In some cases, the preserved tissue sample preserves positional information reflective of its configuration in a tissue. Often, the preserved tissue sample is not homogenized during preservation or prior to isolating nucleic acids, such that positional information of a DNA protein complex excised from the sample is preserved and available as part of the genome structural analysis. In some cases, the preserved tissue sample is stored for at least one week prior to isolating nucleic acids. In some cases, the preserved tissue sample is stored for at least 6 months prior to isolating nucleic acids. In some cases, the preserved tissue sample is transported from a collection point prior to isolating nucleic acids. In some cases, the preserved tissue sample is collected in a sterile environment. In some cases, the preserved tissue sample is positioned in a nonsterile environment prior to isolating nucleic acids.

Provided herein are methods of obtaining long distance sequence information, such as genomic structural information from a preserved sample, such as a crosslinked paraffin-embedded tissue sample. Some such methods comprise: isolating nucleic acids from the crosslinked paraffin-embedded tissue sample such that protein DNA complexes are not destroyed or disrupted; tagging a protein DNA complex such that a first DNA segment and a second DNA segment are identified as arising from a common protein DNA complex; separating the first DNA segment and the second DNA segment from the common DNA complex; generating sequence information from the first DNA segment and the second DNA segment; and assigning sequence information sharing tag sequence indicative of a common protein DNA complex to a common genomic structure. In some cases, the crosslinked paraffin-embedded tissue is not homogenized prior to isolating nucleic acids. In some cases, the tag sequence comprises an oligo tag that identifies a complex. In some cases, the tag sequence arises from ligating the first segment to the second segment. In some cases, isolating nucleic acids from the preserved sample, such as a crosslinked paraffin-embedded tissue sample such that protein DNA complexes are not destroyed or disrupted comprises contacting the crosslinked paraffin-embedded tissue sample to xylene. In some cases, isolating nucleic acids from the preserved sample, such as a crosslinked paraffin-embedded tissue sample such that protein DNA complexes are not destroyed or disrupted comprises contacting the crosslinked paraffin-embedded tissue sample to ethanol. In some cases, isolating nucleic acids from the preserved sample, such as a crosslinked paraffin-embedded tissue sample such that protein DNA complexes are not destroyed or disrupted comprises contacting the crosslinked paraffin-embedded tissue sample to ethanol. In some cases, isolating nucleic acids from the preserved sample, such as a crosslinked paraffin-embedded tissue sample such that protein DNA complexes are not disrupted comprises protecting the sample from boiling conditions. In some cases, separating the first DNA segment and the second DNA segment from the common DNA complex comprises proteinase K treatment. Extraction processes optionally do not involve the addition of any crosslinking agent during the extraction process. Rather, complexes generated pursuant to sample preservation are relied upon so as to minimize the number of exposures to crosslinking that potentially harm nucleic acids in the preserved. Alternately, nucleic acids are isolated and a crosslinking agent is added only after nucleic acid isolation and chromatin reassembly.

Provided herein are methods of obtaining long distance sequence information, such as genomic structural information from a preserved sample, such as a crosslinked paraffin-embedded tissue sample. Some such methods comprise: isolating nucleic acids from the crosslinked paraffin-embedded tissue sample such that nucleic acid fragments of greater than 50 kb are recovered; contacting the nucleic acids to a plurality of nucleic acid binding moieties to form at least one complex such that a first DNA segment and a second DNA segment of a nucleic acid molecule are held together independent of their common phosphodiester backbone; cleaving at least one phosphodiester backbone of the at least one complex; tagging the at least one complex such that the first DNA segment and a second DNA segment are identified as arising from a common complex; separating the first DNA segment and the second DNA segment from the common complex; generating sequence information from the first DNA segment and the second DNA segment; and assigning sequence information sharing tag sequence indicative of a common protein DNA complex to a common genomic structure. In some cases, the crosslinked paraffin-embedded tissue sample is not homogenized prior to isolating nucleic acids. In some cases, the tag sequence comprises an oligo tag that identifies a complex. In some cases, the tag sequence arises from ligating the first DNA segment to the second DNA segment. In some cases, isolating nucleic acids from the preserved sample, such as a crosslinked paraffin-embedded tissue sample such that nucleic acid fragments of greater than 50 kb are recovered comprises contacting the preserved sample, such as a crosslinked paraffin-embedded tissue sample to at least one of an anthranilate and a phosphanilate. In some cases, the isolating is performed at a temperature not greater than 40° C. In some cases, the isolating is performed at a temperature not greater than 40° C. In some cases, separating the first DNA segment and the second DNA segment from the common DNA complex comprises proteinase K treatment. In some cases, the plurality of nucleic acid binding moieties comprises nuclear proteins. In some cases, the plurality of nucleic acid binding moieties comprises transposase. In some cases, the plurality of nucleic acid binding moieties comprises histones. In some cases, the plurality of nucleic acid binding moieties comprises nucleic acid binding proteins. In some cases, the plurality of nucleic acid binding moieties comprises nanoparticles. In some cases, cleaving at least one phosphodiester backbone of the at least one complex comprises contacting to a restriction endonuclease. In some cases, wherein cleaving at least one phosphodiester backbone of the at least one complex comprises contacting to a nonspecific endonuclease. In some cases, cleaving at least one phosphodiester backbone of the at least one complex comprises shearing the DNA. In some cases, cleaving at least one phosphodiester backbone of the at least one complex comprises contacting to a transposase. In some cases, cleaving at least one phosphodiester backbone of the at least one complex comprises contacting to a topoisomerase.

Provided herein are methods of recovering spatially distributed genomic structural information from a preserved tissue sample. Some such methods comprise: obtaining a tissue sample; extracting a portion from a first position of said preserved tissue sample, such as a fixed three-dimensional paraffin-embedded tissue sample; isolating nucleic acids from the portion from the first position such that protein DNA complexes are not destroyed or disrupted; tagging a protein DNA complex such that a first DNA segment and a second DNA segment are identified as arising from a common protein DNA complex; separating the first DNA segment and the second DNA segment from the common DNA complex; generating sequence information from the first DNA segment and the second DNA segment; assigning sequence information sharing tag sequence indicative of a common protein DNA complex to a common genomic structure; and assigning the common genomic structure to the first position of the preserved tissue sample.

In some cases, the preserved tissue sample is not homogenized prior to isolating nucleic acids. In some cases, the tissue sample comprises a fixed three-dimensional paraffin-embedded tissue sample. In some cases, the tag sequence comprises an oligo tag that identifies a complex. In some cases, the tag sequence arises from ligating the first segment to the second segment. In some cases, isolating nucleic acids from the crosslinked paraffin-embedded tissue sample such that protein DNA complexes are not destroyed or disrupted comprises contacting the crosslinked paraffin-embedded tissue sample to xylene. In some cases, isolating nucleic acids from the crosslinked paraffin-embedded tissue sample such that protein DNA complexes are not destroyed or disrupted comprises contacting the crosslinked paraffin-embedded tissue sample to ethanol. In some cases, isolating nucleic acids from the crosslinked paraffin-embedded tissue sample such that protein DNA complexes are not destroyed or disrupted comprises protecting the sample from boiling conditions. In some cases, separating the first DNA segment and the second DNA segment from the common DNA complex comprises proteinase K treatment. In some cases, the tissue sample comprises a fixed three-dimensional paraffin-embedded tissue sample.

Provided herein are methods of reevaluating a treatment regimen trial outcome. Some such methods comprise: obtaining data relating to the treatment regimen outcome in a patient population; obtaining preserved tissue samples, such as fixed tissue samples from a plurality of patients of said patient population; extracting nucleic acid complexes from said fixed tissue samples; determining genomic structural information using said nucleic acid complexes for a plurality of said fixed tissue samples; and correlating the data relating to the treatment regimen outcome to the genomic structural information so as to identify genomic structural information relevant to the treatment regimen outcome. In some cases the preserved tissue sample is not homogenized prior to extracting nucleic acids. In some cases, extracting nucleic acid complexes from said fixed tissue samples; and determining genomic structural information using said nucleic acid complexes for a plurality of said fixed tissue samples comprises any of the methods disclosed herein.

Provided herein are methods of nucleotide sequence assembly. Some such methods comprise: providing a fixed tissue sample; recovering a crosslinked DNA:protein complex from said fixed tissue sample; ligating a first section of DNA from said crosslinked DNA:protein complex to a second section of DNA from said crosslinked DNA:protein complex, thereby forming a ligated DNA; extracting said ligated DNA from said crosslinked DNA:protein complex; sequencing said ligated DNA: and using information from said sequencing to assemble a nucleotide sequence. In some cases, said fixed tissue sample is formalin-fixed. In some cases, the fixed tissue sample is not homogenized prior to isolating nucleic acids. In some cases, said fixed tissue is formalin-fixed paraffin-embedded (FFPE In some cases, said crosslinked DNA:protein complex comprises chromatin. In some cases, said ligating comprises blunt-end ligation. In some cases, the methods disclosed herein further comprise, prior to said ligating, digesting DNA from said crosslinked DNA:protein complex. In some cases, said digesting comprises restriction enzyme digestion. In some cases, the methods disclosed herein further comprise, subsequent to said digesting, filling in sticky ends from said digesting to produce blunt ends. In some cases, wherein said filling in is performed using a biotinylated nucleotide. In some cases, said recovering comprises binding DNA from said crosslinked DNA:protein complex to a solid support. In some cases, said extracting comprises digesting protein from said crosslinked DNA:protein complex. In some cases, said information comprises long-range information over a distance of more than 2000 base pairs (bp). In some cases, said distance is more than 10,000 bp. In some cases, said distance is more than 100,000 bp. In some cases, said distance is more than 200,000 bp. In some cases, the methods disclosed herein further comprise, prior to said recovering, dissolving an embedding material of said fixed tissue sample. In some cases, said embedding material comprises paraffin.

Provided herein are methods of tissue sample analysis. Some such methods comprise: providing a fixed tissue sample; collecting a first portion of said fixed tissue sample and a second portion of said fixed tissue sample, wherein said first portion and said second portion are from different regions of said fixed tissue sample; recovering a first crosslinked DNA:protein complex from said first portion and a second crosslinked DNA:protein complex from said second portion; (i) ligating a first section of DNA from said first crosslinked DNA:protein complex to a second section of DNA from said first crosslinked DNA:protein complex, thereby forming a first ligated DNA, and (ii) ligating a second section of DNA from said second crosslinked DNA:protein complex to a second section of DNA from said second crosslinked DNA:protein complex, thereby forming a second ligated DNA: extracting said first ligated DNA from said first crosslinked DNA:protein complex and said second ligated DNA from said second crosslinked DNA:protein complex; sequencing said first ligated DNA and said second ligated DNA; and using information from said sequencing to assemble a first nucleotide sequence and a second nucleotide sequence. In some cases, the fixed tissue sample is not homogenized prior to isolating nucleic acids. In some cases, said fixed tissue sample is formalin-fixed. In some cases, said fixed tissue is formalin-fixed paraffin-embedded (FFPE). In some cases, said first crosslinked DNA:protein complex and said second crosslinked DNA:protein complex each comprise chromatin. In some cases, said ligating in (d)(i) and in (d)(ii) comprises blunt-end ligation. In some cases, the methods disclosed herein further comprise, prior to said ligating in (d)(i) and in (d)(ii), digesting DNA from said first crosslinked DNA:protein complex and from said second crosslinked DNA:protein complex. In some cases, said digesting comprises restriction enzyme digestion. In some cases, the methods disclosed herein further comprise, subsequent to said digesting, filling in sticky ends from said digesting to produce blunt ends. In some cases, said filling in is performed using a biotinylated nucleotide. In some cases, said recovering comprises binding DNA from said first crosslinked DNA:protein complex and from said second crosslinked DNA:protein complex to a solid support. In some cases, said extracting comprises digesting protein from said first crosslinked DNA:protein complex and from said second crosslinked DNA:protein complex. In some cases, said information comprises long-range information over a distance of more than 2000 base pairs (bp). In some cases, said distance is more than 10,000 bp. In some cases, said distance is more than 100,000 bp In some cases, said distance is more than 200,000 bp. In some cases, the methods disclosed herein further comprise, prior to said recovering, dissolving an embedding material of said fixed tissue sample. In some cases, said embedding material comprises paraffin.

Also provided herein are kits for obtaining genomic structural information from a preserved sample. Some such kits comprise: a buffer, a DNA binding agent, an affinity tag binding agent, deoxynucleotides, tagged deoxynucleotides, a DNA fragmenting agent, an end repair enzyme, a ligase, a protein removal agent, and instructions for use in obtaining genomic structural information from the preserved sample. Optionally, the kits further comprise reagents for PCR or instructions for use of the kit in combination with PCR reagents. In some cases, reagents for PCR comprise a buffer, nucleotides, a forward primer, a reverse primer, and a thermostable DNA polymerase. Various buffers comprise at least one of a restriction digest buffer, an end repair buffer, a ligation buffer, a TE buffer, a wash buffer, a TWB solution a NTB solution, a LWB solution, a NWB solution, and a crosslink reversal buffer. In some cases, the restriction digest buffer comprises a DpnII buffer. For example, the end repair buffer often comprises NEB buffer 2. The ligation buffer often comprises T4 DNA ligase buffer, BSA, and Triton X-100. The TE buffer often comprises tris and EDTA. In some cases, the wash buffer comprises tris and sodium chloride. In some cases, the TWB solution comprises tris, EDTA, and Tween 20. In some cases, the NTB solution comprises tris, EDTA, and sodium chloride. In some cases, the LWB solution comprises tris, lithium chloride, EDTA, and Tween 20. In some cases, the NWB solution comprises tris, sodium chloride, EDTA, and Tween 20. In some cases, the crosslink reversal buffer comprises tris. SDS, and calcium chloride. In some cases, the DNA binding agent comprises chromatin capture beads. In some cases, the chromatin capture beads comprise a PEG-800 powder, a tris buffer, sodium chloride, EDTA, a surfactant, TE buffer, and sera-mag beads. In some cases, the affinity tag binding agent comprises streptavidin beads. In some cases, the streptavidin beads comprise dynabeads. In some cases, the deoxynucleotides comprise at least three of dATP, dTTP, dGTP, and dCTP. In some cases, the biotinylated deoxynucleotide comprises at least one of biotinylated dCTP, biotinylated dATP, biotinylated dTTP, and biotinylated dGTP. In some cases, the DNA fragmenting agent is at least one of a restriction enzyme, a transposase, a nuclease, a sonication device, a hydrodynamic shearing device, and a divalent metal cation. In some cases, the restriction enzyme comprises DpnII. In some cases, the end repair enzyme comprises at least one of T4 DNA polymerase, klenow DNA polymerase, and T4 polynucleotide kinase. In some cases, the ligase comprises a T4 DNA ligase. In some cases, the protein removal agent comprises at least one of a protease and a phenol. In some cases, the protease comprises at least one of a proteinase K, a *Streptomyces griseus* protease, a serine protease, a cysteine protease, a threonine protease, an aspartic protease, a glutamic protease, a metalloprotease, and an asparagine peptide lyase. In some cases, the kit optionally comprises a solvent for removing an embedding material. In some cases, the solvent is at least one of a xylene, a benzene, and a toluene, considering the kit components listed herein and substantially equivalent variants thereof, alternative kits are contemplated wherein at least one commercially available kit component is excluded, being replaced by instructions for successful use of the remaining components in combination with reagents independently obtained.

INCORPORATION BY REFERENCE

All publications, patents, and patent applications mentioned in this specification are herein incorporated by reference to the same extent as if each individual publication, patent, or patent application was specifically and individually indicated to be incorporated by reference. All publications, patents, and patent applications mentioned in this specification are herein incorporated by reference in its entirety as well as any references cited therein.

BRIEF DESCRIPTION OF THE DRAWINGS

FIG. 4A, FIG. 43, and FIG. 4C depict image analysis-based results at the same pair of chromosomes compared in three different samples.

FIG. 6A shows equal bin sizes and FIG. 6B shows bin interpolation.

FIG. 9A depicts data for an 80 kb inversion with flanking 20 kb repetitive regions.

FIG. 9B depicts data for a phased heterozygous deletion.

DETAILED DESCRIPTION

A large repository of biological information is stored in preserved samples, such as formalin-fixed paraffin embedded (FFPE) tissue samples, such samples are routinely obtained during surgery such as surgery to excise a diseased or damaged tissue from a patient. However, crosslinking that occurs during preservation of such samples was thought to prohibit DNA extraction from these samples. Preservation and storage are technically straightforward and economical, and as a result large numbers of patient samples have been stored using this approach. As a result, obtaining and preserving samples from, for example, tumor tissue of patients undergoing a cancer therapeutic trial has long been routine.

Figure 1A:
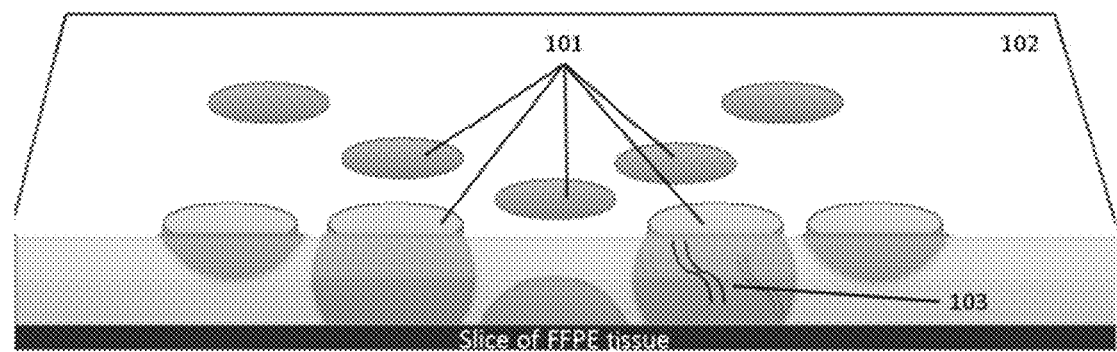
FIG. 1A depicts an exemplary schematic of a formalin fixed, paraffin embedded (FFPE) tissue sample.

Until recently these samples were useful only for accessing structural information. Three-dimensional tissue sections were well-preserved and available for morphological analysis, but the process of tissue preservation prohibited accessing genome-level information from the preserved samples. For example, FIG. 1A depicts an exemplary schematic of a preserved sample (e.g., an FFPE sample). Cells 101 are depicted as spatially distributed within the tissue 102 of the fixed sample, such that their three-dimensional distribution is preserved. Nucleic acids 103 are present within cells.

Efforts have been made to obtain nucleic acid information from these samples, but the nucleic acids obtained are short and highly degraded such that only local sequence information is obtainable. Accordingly, genome level information regarding rearrangements is not readily obtainable. Rearrangements can include but are not limited to deletions, duplications, insertions, inversions or reversals, translocations, joins, fusions, and fissions.

In a number of known disorders it is these genome-scale rearrangements that have been implicated in disease. Gene fusions, particularly those resulting from genome rearrangements, are particularly common in some cancers, and are often indicative of disease outcome in response to therapy. Generally, these rearrangement patterns do not reliably correlate to one or another morphological structure in a preserved sample. Rather, they must be genotyped directly. As a result, this information was unavailable despite tumor samples themselves being preserved, and data regarding the tumors' response to chemotherapy or other therapy being readily available.

Methods and compositions herein relate to the determination of genomic structural information from preserved samples, such as the samples contemplated above. Some methods herein rely upon approaches that utilize extraction approaches so as to access genomic structural information contained in preserved samples. Protein DNA complexes are extracted from the samples such that complexes are not destroyed or disrupted, and utilize the fact that a first segment and a second segment of nucleic acid are held together independent of their phosphodiester backbones. The segments are tagged, either using oligos or by ligating the segments to one another, and sequence information is obtained allowing one to assign contigs to which the sequence information maps to a common scaffold. By assessing the frequency and types of read pairs generated by evaluating ligated segments, one may infer both physical linkage or phase information, and determine the presence of particular genomic structural rearrangements, such as structural rearrangements implicated in a disorder.

Also preserved in these samples is the three-dimensional configuration of the preserved tissue. Cancerous tumors are generally heterogeneous as to their genomic structure. Tumors are often characterized by separate mutations relating to DNA repair defects, cell death suppression, tumor growth, and metastasis. Tumors generally involve multiple cell sub-populations having various combinations of mutations and having various degrees of health risk. Often, these risks are correlated with local morphology. Tumor cell populations range from quiescent, to benign locally replicating cell populations, to metastasizing cell populations representing relatively high health risks. Thus, identifying not only the presence of a given genome architecture generally in a tumor but the local genome architecture of spatially separated subpopulations within a tumor sample is of value to researchers and practitioners trying to assess the relative efficacy of a prior drug treatment or trying to select an appropriate drug for a patient presenting a tumor of unknown risk. In particular, correlating a genome architecture with a position in a tumor and with a known cell morphology within the tumor is valuable for determining which genome architectures correspond most closely to tumor positions and local cell morphologies of highest risk.

It is thought that DNA extracted from preserved samples, such as FFPE samples, using approaches in the art are often less than 300 base pairs in length. Some nicking and damage may occur during the preservation (e.g., FFPE) process and subsequent dehydration and long-term storage. A significant amount of fragmentation can also occur during the extraction process, which typically involves overnight proteinase K treatment followed by boiling in order to reverse cross-linking and release the DNA. Nonetheless, through the approaches herein, such nucleic acid molecules, in combination with structural information preserved in DNA protein complexes excised without destruction or disruption of DNA protein complexes, yield information informative as to genome structural rearrangements.

Native and Reconstituted Chromatin

Preserved samples often comprise native or reconstituted chromatin, or otherwise have nucleic acids bound at multiple points to a protein or non-protein scaffold such that a first segment and a second segment are held together independent of their common phosphodiester backbone immediately prior to contacting a crosslinking agent. In eukaryotes, genomic DNA is packed into chromatin as chromosomes within the nucleus. The basic structural unit of eukaryotic native chromatin is the nucleosome, which consists of 146 base pairs (bp) of DNA wrapped around a histone octamer. The histone octamer consists of two copies each of the core histone H2A-H2B dimers and H3-H4 dimers. Nucleosomes are regularly spaced along the DNA in what is commonly referred to as "beads on a string".

The assembly of core histones and DNA into nucleosomes is mediated by chaperone proteins and associated assembly factors. Nearly all of these factors are core histone-binding proteins. Some of the histone chaperones, such as nucleosome assembly protein-1 (NAP-1), exhibit a preference for binding to histones H3 and H4. It has also been observed that newly synthesized histones are acetylated and then subsequently deacetylated after assembly into chromatin. The factors that mediate histone acetylation or deacetylation therefore play an important role in the chromatin assembly process.

In general, two in vitro methods have been developed for reconstituting or assembling chromatin. One method is ATP-independent, while the second is ATP-dependent. The ATP-independent method for reconstituting chromatin involves the DNA and core histones plus either a protein like NAP-1 or salt to act as a histone chaperone. This method results in a random arrangement of histones on the DNA that does not accurately mimic the native core nucleosome particle in the cell. These particles are often referred to as mononucleosomes because they are not regularly ordered, extended nucleosome arrays and the DNA sequence used is usually not longer than 250 bp (Kundu, T. K. et al., Mol. Cell 6: 551-561, 2000). To generate an extended array of ordered nucleosomes on a greater length of DNA sequence, the chromatin must be assembled through an ATP-dependent process.

The ATP-dependent assembly of periodic nucleosome arrays, which are similar to those seen in native chromatin, requires the DNA sequence, core histone particles, a chaperone protein and ATP-utilizing chromatin assembly factors. ACF (ATP-utilizing chromatin assembly and remodeling factor) or RSF (remodeling and spacing factor) are two widely researched assembly factors that are used to generate extended ordered arrays of nucleosomes into chromatin in vitro (Fyodorov, D. V., and Kadonaga, J. T. Method Enzymol. 371: 499-515, 2003; Kundu, T. K. et al. Mol. Cell 6: 551-561, 2000).

In particular embodiments, the methods of the disclosure can be easily applied to any type of fragmented double stranded DNA including but not limited to, for example, free DNA isolated from plasma, serum, and/or urine; apoptotic DNA from cells and/or tissues; DNA fragmented enzymatically in vitro (for example, by DNase I, transposase, and/or restriction endonuclease); and/or DNA fragmented by mechanical forces (hydro-shear, sonication, nebulization, etc.).

Reconstituted chromatin need not comprise nucleosomes or even proteins. Rather, reconstituted chromatin broadly defined comprises at least one nucleic acid bound such that a first segment and a second segment are held together independent of their phosphodiester backbones. A number of nucleic acid binding moieties are suitable for chromatin reconstitution. Examples include nuclear proteins such as histones individually or assembled into nucleosomes, as well as other nucleic acid binding proteins such as transcription factors, transposons, or any other protein having nucleic acid binding activity. Non-nuclear proteins are also contemplated, such as organellar nucleic acid binding proteins. Non-protein moieties are also contemplated, such as nanoparticles or nucleic acid binding surfaces.

Preserving DNA Connectivity Information in Preserved Extracted Nucleic Acids

Preserved samples, such as formalin-fixed, paraffin embedded samples, often comprise nucleic acids having damage, such as damage caused by fixative and/or embedding materials. A relevant component in making use of DNA is preserving the integrity of DNA physical linkage information of isolated DNA subject to a DNA damaging agent. Although DNA is a relatively stable molecule, the integrity of DNA is subject to environmental factors and particularly time. The presence of nuclease contamination, hydrolysis, oxidation, chemical, physical and mechanical damages represent some of the major threats to DNA preservation. The mechanical, environmental and physical factors encountered by DNA during transportation frequently leave them in fragments and potentially lose long-range information, which are critical for genomic analysis. Existing methods for preserving DNA information mostly delay the decay of DNA but provide little protection to DNA damage over time, especially when fragmentation occurs. In many cases, such DNA damage can be mitigated by fixing and embedding samples intended for long term storage. For example, FFPE (formalin-fixation, paraffin embedded) samples can be preserved for a long time. However, the preservation process can result in DNA damage. Additionally, later DNA extraction methods are often harsh and lead to further DNA damage and fragmentation.

Disclosed herein are methods, compositions, and kits related to recovering long-distance genomic information from preserved and/or stored nucleic acid molecules, such as nucleic acid molecules in DNA complexes or chromatin aggregates, such as crosslinked chromatin stored in preserved (e.g., FFPE) samples (including tissue-based preserved samples and cell culture-based preserved samples). In particular, methods, compositions, systems and kits relate to recovery of nucleic acid samples from these preserved samples such that nucleic acid physical linkage information is preserved. Physical linkage information is preserved either by preservation of the nucleic acids themselves in the FFPE extraction process, or by preserving nucleic acid complexes such that physical linkage information is preserved independent of any damage that may occur to the nucleic acids themselves in the extraction process.

Often, double strand breaks occur during DNA storage or during extraction of DNA from a preserved sample such as an FFPE sample, causing loss of physical linkage information. Loss of physical linkage information is particularly detrimental, because it precludes a sequence assembler from determining whether, in a diploid organism sample, mutations that map to a common locus are in fact in the same allele or are present on two separate homologous alleles positioned on different strands of the diploid genome. As genome information is used for personalized medicine or for more medicinal or therapeutic purposes, assigning physical linkage information to assembled contig sequence is of increasing importance.

These challenges to the integrity of DNA are problematic as genomics technologies improve along with expansion of programs for worldwide, prolonged, historical, or large-scale studies of genomes. Such studies are imperative to understand the genomes of current human populations and individuals and their impacts on human health, as well as to preserve present genomes for future studies with ever more powerful techniques. The latter concern also overlaps with forensic interests, which seek to bank DNA samples indefinitely for later analysis and identification.

Preserving Physical Linkage

Preserved samples, such as formalin-fixed, paraffin embedded samples, often pose challenges in determining physical linkage information of nucleic acids from the preserved sample. A number of downstream analyses can be used to obtain physical linkage information from a sample, and are thus harmed or complicated by loss of such information during FFPE-sample DNA extraction. Nucleic acid samples are often intended as templates for amplification of large fragments, for example via polymerase chain reaction ("PCR") using primers known to anneal adjacent to a region of interest. PCR relies upon the presence of a template from which one generates multiple amplicon nucleic acid molecules. Amplification relies upon two annealing sites (or an annealing site and the reverse complement of a second annealing site) being physically linked to one another on a single molecule. Accordingly, loss of physical linkage between primer annealing sites complicates analyses comprising PCR amplification.

Similarly, cloning a fragment into a cellular host so that it may be replicated, amplified, expressed or manipulated transgenically, is greatly facilitated by having a single molecule as a starting material. Loss of physical linkage for a fragment (that is, cleavage of that fragment) complicates cloning and necessitates multiple additional steps in fragment assembly.

Alternately, some analysis approaches require the preservation of physical proximity but do not require that a first segment and a second segment of a nucleic acid remain physically linked by their phosphodiester backbone. For example, one may assay for co-localization of probes to a first nucleic acid segment and a second nucleic acid segment so as to determine whether they exist on a common molecule in an un-degraded sample. Preservation of physical linkage facilitates this analysis, but is not necessary for such analysis. Assembling the molecule into a reconstituted chromatin complex such that the first segment and the segment are bound independent of their common phosphodiester backbone, for example similarly facilitates such an analysis. Even in the event of cleavage of their common phosphodiester backbone, physical proximity information for the first segment and the second segment is preserved such that probing the complex with a first and a second probe will indicate whether the first fragment and the second fragment exist on a common molecule in the original sample.

Sequencing is another analysis that benefits from preservation of physical linkage information but does not require preservation of physical linkage, or even of physical proximity. Preservation of physical linkage facilitates sequencing, but so do other methods disclosed herein and known to one of skill in the art. Preservation of physical proximity, for example, facilitates sequencing because fragments held in proximity are readily end labeled so as to convey physical linkage information. Exposed internal ends are labeled using oligonucleotide tags that allow adjacent fragment sequence to be mapped to a common molecule. Alternately or in combination, exposed ends are ligated to one another at random, so as to generate read pairs wherein sequence on either side of a marked ligation event is mapped to a common molecule. Even in the absence of physical proximity, sequence analysis is facilitated if a nucleic acid sample is treated so as to add physical proximity markers prior to loss of the physical proximity information. That is, assembly of reconstituted chromatin on a nucleic acid molecule, exposure of internal double-strand ends and labeling of these exposed ends via cross-ligation or via tagging using common oligonucleotides, if performed prior to subjecting the sample to degradation that may jeopardize or cause loss of physical linkage among segments of a molecule.

It is for all of these reasons that simple, affordable technologies for extracting physical linkage information encoded by DNA from preserved (e.g., FFPE) samples has become a critical necessity for the field. The methods disclosed herein are useful in many fields including, by way of non-limiting example, forensics, agriculture, environmental studies, renewable energy, epidemiology or disease outbreak response, and species preservation. Techniques of the present disclosure are used for mapping heterogeneity of a tissue sample, such as a tumor sample. For example, a tissue block can be sampled throughout its volume, and techniques of the present disclosure can be used to analyze the samples, allowing for comparison of variation throughout the tissue volume. Infections can also be analyzed throughout a tissue volume, Techniques of the present disclosure can be used for phasing of clinically important regions, analysis of structural variants, analysis of copy number variants, resolution of pseudogenes (e.g., STRC), targeted panels for drugable structural variants in cancer, and other applications.

In some embodiments of the methods disclosed herein, loss of physical linkage information and/or physical linkage information during sample extraction (e.g., extraction from an FFPE sample) is avoided or reduced by physically preventing or reducing nucleic acid breakage. Loss of phase information and/or physical linkage information is avoided or reduced by holding a first segment and a second segment in physical proximity independent of their phosphodiester backbone. Alternately or in combination, loss of phase information and/or physical linkage information is avoided or reduced by labeling a first segment and a second segment using a common or reciprocally complementary tag such that, upon loss of physical proximity information and loss of a common phosphodiester backbone tether, sequencing tag information that is affixed to a first segment and a second segment is sufficient to identify the two segments as sharing a common phase or common molecule in the original, un-degraded sample. Additionally, or alternatively, labeling is achieved by ligation of a first segment to a second segment, wherein the second segment is non-adjacent to the first segment, though they are physically linked on the same original DNA molecule.

Nucleic acid degradation arises from a number of diverse sources. Contemplated herein is protection from DNA degradation of a number of types, in particular DNA degradation that results in the introduction of double-strand breaks such as those that result in loss of physical linkage between a first segment and a second segment on an original common molecule in a nucleic acid sample. Of particular significance is nonenzymatic DNA degradation, such as that which occurs over time to stored nucleic acid samples, or that occurs to samples stored at room temperature. Nonenzymatic nucleic acid degradation includes boiling, proteinase treatment, UV radiation, oxidation, hydrolysis, physical stress such as shearing or tangling, or nucleophilic attach by a free 3' hydroxyl group onto an internal bond of a nucleic acid molecule such that the molecule is cleaved or a lariat formed. Also contemplated herein is nucleic acid damage resulting from enzymatic activity, such as nonspecific endonuclease activity, topoisomerase activity involving single strand nicking or double-strand breakage, restriction endonuclease activity, transposase activity, DNA mismatch repair or base excision, or other enzymatic activity that results in nucleic acid damage such as loss of phase information and/or loss of physical linkage information. Enzymatic degradation is exogenous in some cases, such as that which results from incomplete nucleic acid isolation, or initial isolation in a nonsterile environment such as that which may be encountered during collection 'in the field' such as a remote location or a location which, due for example to an epidemic or other burden on scientific resources, where sterile conditions are not easily or regularly obtained.

Some embodiments herein relate to assembling chromatin in vitro onto partially or totally isolated nucleic acids, such as nucleic acids extracted from preserved (e.g., FFPE) samples, such that physical linkage information relating a first segment of a nucleic acid molecule to a second segment of the nucleic acid molecule is not lost in the event that a double strand break occurs between the first nucleic acid molecule and the second nucleic acid molecule. The reassembled chromatin comprises in some cases nucleic acid binding proteins provided from another source. Alternately, in some cases an incompletely isolated nucleic acid sample, such as a nucleic acid sample treated so as to destroy or disrupt its native chromatin configuration, to inactivate native nuclease activity, or to destroy or disrupt native chromatin and to inactivate native nuclease activity, is contacted to a crosslinking agent so as to stabilize nucleic acids in the sample. In other cases, nucleic acids from preserved samples are analyzed using the native chromatin structures preserved in the sample.

Double strand breaks often occur during DNA storage over time. As a result, phasing information of DNA molecule is often difficult to obtain since variants cannot be confidently associated with haplotypes over long-distances. Further, nucleic acid segments separated by long repetitive regions cannot be linked or assembled into a common scaffold. These challenges are only amplified by double strand break introduction resulting from FFPE-extraction methods, boiling, proteinase treatments, long term storage, room temperature storage, enzymatic or nonenzymatic degradation, or contamination during or after isolation with a composition having a nuclease activity.

Sample degradation significantly affects de novo assembly. The disclosure addresses these problems simultaneously in some embodiments by preventing DNA damage through double strand breaks over time and optionally additionally by reducing the impact on phase determination of double-strand breakage. The preserved high DNA integrity enables methods for generating extremely long-range read pair data (XLRPs) that span genomic distances on the order of hundreds of kilobases, and up to megabases with the appropriate input DNA.

Such data is invaluable for overcoming the substantial barriers presented by loss of physical linkage information by the loss of physical linkage information due to double strand breaks, DNA fragmentation, and large repetitive regions in genomes, including centromeres; enabling cost-effective de novo assembly; and producing re-sequencing data of sufficient integrity and accuracy for genomic analysis and personalized medicine.

The disclosure herein addresses these problems by preventing the loss of phase and/or physical linkage information that usually occurs to common extraction (e.g., FFPE extraction) methods, or alternately by preserving phase and/or physical linkage information independent of double strand breakage, such that physical linkage information is preserved even upon downstream processing, such as boiling of proteinase treatment. Physical linkage information can be preserved physically, through binding a first segment and a second segment of a nucleic acid molecule such that they are held together independent of their common phosphodiester backbone. Alternately or in combination, physical linkage information can be preserved through the tagging or reciprocal labelling of a first segment and a second segment of a common nucleic acid molecule such that, in the event of introduction of a double strand break between the segments, tag or other label information obtained through sequencing the first segment and adjacent sequence and the second segment and adjacent sequence is sufficient to map the first segment and the second segment to a common phase of a common nucleic acid molecule. Tagging can be alternatively achieved through ligating a first segment to a second segment, wherein the second segment is non-adjacent to the first segment, though they are physically linked on the same original DNA molecule. For example, a first segment and a second segment can be non-adjacent along the DNA molecule sequence, but in close physical proximity to each other or at least constituent in a common complex due to folding in a structure such as chromatin. Exposed ends of such segments can be ligated together. In another example, tagging is achieved by ligating barcodes (e.g., oligonucleotide barcodes) or other tags to both the first and second segments such that the first segment and the second segment are recognizably mapped to a common complex or a common molecule. Methods of preserving physical linkage information though chromatin reassembly or nucleic acid labeling or tagging have been previously described (PCT patent application number PCT/US2016/024225, incorporated herein in its entirety).

Of significant importance of some embodiments herein is the preservation of long nucleic acids from preserved samples such as FFPE embedded samples, such that chromatin may be reconstituted using protein or nonprotein nucleic acid binding moieties. Use of reconstituted chromatin is advantageous in forming associations among very distant, but molecularly-linked, segments of DNA. The disclosure enables distant segments to be brought together and physically bound to one another independent of their common phosphodiester backbone, thereby physically connecting previously distant portions of a common DNA molecule. As a consequence, breakage of double-strand linkages between these disparate nucleic acid segments does not result in loss of phase and/or physical linkage information. Preferably, care is taken such that chromatin reconstitution occurs under conditions that minimize or prevent the inclusion of more than one nucleic acid molecule per individual reconstituted chromatin unit. Subsequent processing allows for the sequence of the associated segments to be ascertained, yielding read pairs whose separation on the genome extends up to the full length of the input DNA molecules.

Samples

Samples herein are preserved, for example as formalin fixed paraffin embedded samples, and in some cases stored for a substantial period of time prior to analysis. Samples may be obtained pursuant to a drug trial, and examined years later in an effort to identify genomic structural rearrangements relevant to or predictive of a positive drug treatment outcome. Such samples can be used in determining long distance sequence information, such as genomic structural information. Long-range information generated by methods disclosed herein can be used for detecting structural variations, such as inversions, deletions, and duplications. Structural variation detection can also be used for identifying when active enhancers are brought into proximity to oncogenes or when repressive cis-acting elements are brought into proximity to tumor suppressors. Identification of such driver events are applicable to cancer studies, in particular to studies wherein tumor tissue is preserved long after a study is completed, and wherein various cell subpopulations of a tumor harbor differing genomic restructuring events. For example, novel structural variants can be detected and determined to be the causative agent of a cancer type.

Methods herein are used to obtain genomic structural information from preserved samples, such as samples obtained from a patient, a research animal, or an environmental sample. Some such samples include biopsy samples, surgical samples, tumor samples, whole organs, and other samples. These are preserved, often in a fixative such as a formaldehyde, a formalin, UV light, mitomycin C, nitrogen mustard, melphalan, 1,3-butadiene diepoxide, cis diaminedichloroplatinum(II), or cyclophosphamide. Preserved samples are fixed directly and without homogenization, in some cases, by dropping the sample into a fixative solution. Once preserved, these samples can be stored for months or several years. In addition, the intact nature of the sample preserves positional information of the sample allowing an analysis of genomic structural information spatially throughout the sample. For example, the genomic structural information of the edge of a biopsy sample can be compared to the genomic structural information of the center of a biopsy sample.

Structural variation detection based on the methods disclosed herein can also be used to determine the DNA structure of gene fusions. Commonly used FISH methods or RNA-seq can determine that a DNA rearrangement has occurred, but the actual sequence of the rearrangement is not provided by these approaches. On the other hand, methods are provided herein for determining the structural variant that created a gene fusion of interest.

Provided herein are methods for determining three-dimensional DNA structural information. In some cases, the open or closed state of chromatin is detected by these methods. Structural information gathered by the methods disclosed herein can also be used to determine the presence or absence of insulators or loops, or for detecting novel loops or other new intra or inter chromosomal associations.

Provided herein are methods for tissue mapping. Tissue mapping is a process by which punch biopsies from different areas of a tissue, such as a tumor, and structural or phasing information is determined from each biopsy in order to determine the genomic heterogeneity in different regions.

Methods disclosed herein can be used for generating read-pair libraries comprising long range information from preserved (e.g., FFPE) samples. These libraries can be recovered from samples preserved for an indefinite period of time, for example in FFPE tissues.

Provided herein are methods for determining the structural and phase information of lymphocytes. In some cases, these methods are used to distinguish between different cell or receptor subtypes.

Methods provided herein are used in some embodiments for the detection of structural variants or genome rearrangements using long range data and phase information containing data. The starting material for these methods are samples which have been fixed in formalin and embedded in paraffin, as is common for most clinical sample preservation. Using the methods provided herein, structural and long range information is obtained from samples; such information is not obtainable using current methods due to high levels of DNA fragmentation. Therefore, use of the methods provided herein provides the opportunity to use this new data in many areas of clinical research and drug discovery.

Clinical research applications of the methods provided herein include tracking a therapy response or resistance using patient samples. To mitigate library preparation or sequencing variations, it is beneficial to process samples at the same time. This requires early time-point samples to be preserved, such as by FFPE. The methods provided herein provide a way to efficiently extract usable genomic material from these preserved samples, such that samples from multiple time points can be processed and analyzed at the same time.

In an example, a sample (e.g., a biopsy) is taken from a patient and placed in a fixative (e.g., formalin) during a medical procedure. This fixed sample is subsequently analyzed using the techniques of the present disclosure. For example, genomic features such as rearrangements relevant to cancer can be identified. Tumor/non-tumor phasing can be analyzed to differentiate cancer genomic information from somatic genomic information.

Furthermore, using the methods provided herein, useful long range genomic information can also be obtained from older samples that were preserved before the invention of such extraction methods. For example, tumor sample banks can be processed using the methods provided herein and the correlated to the known outcomes of the patients in order to mine this information for clinically relevant information. In this way, methods provided herein allow for prognosis and diagnosis correlations.

Methods and compositions provided herein can be used to determine structural variation profiles of preserved tissues. These structural variation profiles can be used in conjunction with other data sets, for example gene expression profiles, mutation profiles, methylation profiles, etc., to define distinct subtypes or other clusters.

Structural variation profiles determined by methods provided herein are also used to determine the structural evolution of mutations over time. For example, one may in some cases monitor the evolution of structural variants in tumor genome structure from inception, through progression or regression. In this way, tumor malignancies and metastasis can be better understood. Monitoring is available to be done both spatially, by examining various subpopulations in a three-dimensional sample, and temporally, by examining a time course of preserved samples, depending upon sample availability.

Methods provided herein can also be performed on banked, archived, or otherwise long-termed stored genetic samples. For example, archives of preserved tissue samples from now deceased patients who suffered from rare or unknown diseases can be analyzed by the methods provided herein, therefore providing insight not obtainable using standard methods.

Samples analyzed by the techniques disclosed herein can be degraded or have been subjected to various conditions, including conditions that are detrimental to the preservation of DNA or of long-range DNA information, including structural information. In some cases, samples have been subjected to acid treatment. In some cases, samples have been subjected to crosslinking agents, such as formaldehyde or formalin. In some cases, samples have been subjected to embedding, such as paraffin embedding. In some cases, samples have not been subjected to embedding, such as paraffin embedding. In some cases, samples have been subjected to heat treatment (e.g., to melt an embedding material). In some cases, samples have been subjected to a solvent, such as xylene (e.g., to dissolve an adhesive).

Fixed samples can have been subjected to various conditions after fixation but prior to subsequent processing or analysis. For example, after fixation, a time can elapse of at least about 10 minutes, 20 minutes, 30 minutes, 40 minutes, 50 minutes, 1 hour, 1.5 hours, 2 hours, 3 hours, 4 hours, 5 hours, 6 hours, 7 hours, 8 hours, 9 hours, 10 hours, 11 hours, 12 hours, 18 hours, 1 day, 2 days, 3 days, 4 days, 5 days, 6 days, 1 week, 2 weeks, 3 weeks, 4 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 15 years, 20 years, 25 years, 30 years, 35 years, 40 years, 45 years, 50 years, 55 years, 60 years, 65 years, 70 years, 75 years, 80 years, 85 years, 90 years, 95 years, 100 years, or more. After fixation, a sample can be subjected to a temperature increase of at least about 5° C., 10° C., 15° C., 20° C., 25° C. 30° C., 35° C., 40° C., 45° C., 50° C., 55° C., 60° C., 65° C., 70° C., 75° C., 80° C., 85° C., 90° C., 95° C., 100° C., or more. After fixation, a sample can be subjected to a temperature decrease of at least about 5° C., 10° C., 15° C., 20° C., 25° C., 30° C. 35° C., 40° C., 45° C., 50° C., 55° C., 60° C., 65° C. 70° C., 75° C., 80° C., 85° C., 90° C., 95° C., 100° C., or more. After fixation, a sample can be subjected to a pressure (e.g., ambient pressure) decrease of at least about 10 Pascal (Pa), 20 Pa, 30 Pa, 40 Pa, 50 Pa, 60 Pa, 70 Pa, 80 Pa, 90 Pa, 100 Pa, 110 Pa, 120 Pa, 130 Pa, 140 Pa, 150 Pa, 160 Pa, 170 Pa, 180 Pa, 190 Pa, 200 Pa, 210 Pa, 220 Pa, 230 Pa, 240 Pa, 250 Pa, 260 Pa, 270 Pa, 280 Pa, 290 Pa, 300 Pa, 310 Pa, 320 Pa, 330 Pa, 340 Pa, 350 Pa, 360 Pa, 370 Pa, 380 Pa, 390 Pa, 400 Pa, 410 Pa, 420 Pa, 430 Pa, 440 Pa, 450 Pa, 460 Pa, 470 Pa, 480 Pa, 490 Pa, 500 Pa, 550 Pa, 600 Pa, 650 Pa, 700 Pa, 750 Pa, 800 Pa, 850 Pa, 900 Pa, 950 Pa, 1000 Pa, 2000 Pa, 3000 Pa, 4000 Pa, 5000 Pa, 6000 Pa, 7000 Pa, 8000 Pa, 9000 Pa, 10000 Pa, 20000 Pa, 30000 Pa, 40000 Pa, 50000 Pa, 60000 Pa, 70000 Pa, 80000 Pa, 90000 Pa, 100000 Pa, 101325 Pa. or more. After fixation, a sample can be subjected to a pressure (e.g., ambient pressure) increase of at least about 10 Pascal (Pa), 20 Pa, 30 Pa, 40 Pa, 50 Pa, 60 Pa, 70 Pa, 80 Pa, 90 Pa, 100 Pa, 110 Pa, 120 Pa, 130 Pa, 140 Pa, 150 Pa, 160 Pa, 170 Pa, 180 Pa, 190 Pa, 200 Pa, 210 Pa, 220 Pa, 230 Pa, 240 Pa, 250 Pa, 260 Pa, 270 Pa, 280 Pa, 290 Pa, 300 Pa, 310 Pa, 320 Pa, 330 Pa, 340 Pa, 350 Pa, 360 Pa, 370 Pa, 380 Pa, 390 Pa, 400 Pa, 410 Pa, 420

Pa, 430 Pa, 440 Pa, 450 Pa, 460 Pa, 470 Pa, 480 Pa, 490 Pa, 500 Pa, 550 Pa, 600 Pa, 650 Pa, 700 Pa, 750 Pa, 800 Pa, 850 Pa, 900 Pa, 950 Pa, 1000 Pa, 2000 Pa, 3000 Pa, 4000 Pa, 5000 Pa, 6000 Pa, 7000 Pa, 8000 Pa, 9000 Pa, 10000 Pa, 20000 Pa, 30000 Pa, 40000 Pa, 50000 Pa, 60000 Pa, 70000 Pa, 80000 Pa, 90000 Pa, 100000 Pa, 101325 Pa, or more. After fixation, a sample can be subjected to an altitude change of at least about 0.1 meters (m), 0.2 m, 0.3 m, 0.4 m, 0.5 m, 0.6 m, 0.7 m, 0.8 m, 0.9 m, 1 m, 2 m, 3 m, 4 m, 5 m, 6 m, 7 m, 8 m, 9 m, 10 m, 11 m, 12 m, 13 m, 14 m, 15 m, 16 m, 17 m, 18 m, 19 m, 20 m, or more.

Fixed samples can be fixed in a fixation reaction that lasts at least about 10 minutes, 20 minutes, 30 minutes, 40 minutes, 50 minutes, 1 hour, 1.5 hours, 2 hours, 3 hours, 4 hours, 5 hours, 6 hours, 7 hours, 8 hours, 9 hours, 10 hours, 11 hours, 12 hours, 18 hours, 24 hours, or more. In some cases, fixed samples are fixed in a fixation reaction that lasts at least about 30 minutes. In some cases, the fixation reaction time can be the time elapsed before the fixation reaction is quenched. In some cases, fixed samples are fixed in a fixation reaction that is not quenched.

The methods disclosed herein can be used in the analysis of genetic information of selective genomic regions of interest as well as genomic regions which may interact with the selective region of interest. Amplification methods as disclosed herein can be used in the devices, kits, and methods known to the art for genetic analysis, such as, but not limited to those found in U.S. Pat. Nos. 6,449,562, 6,287,766, 7,361,468, 7,414,117, 6,225,109, and 6,110,709. In some cases, amplification methods of the present disclosure can be used to amplify target nucleic acid for DNA hybridization studies to determine the presence or absence of polymorphisms. The polymorphisms, or alleles, can be associated with diseases or conditions such as genetic disease. In other cases, the polymorphisms can be associated with susceptibility to diseases or conditions, for example, polymorphisms associated with addiction, degenerative and age related conditions, cancer, and the like. In other cases, the polymorphisms can be associated with beneficial traits such as increased coronary health, or resistance to diseases such as HIV or malaria, or resistance to degenerative diseases such as osteoporosis, Alzheimer's or dementia.

The compositions and methods of the disclosure can be used for diagnostic, prognostic, therapeutic, patient stratification, drug development, treatment selection, and screening purposes. The present disclosure provides the advantage that many different target molecules can be analyzed at one time from a single biomolecular sample using the methods of the disclosure. This allows, for example, for several diagnostic tests to be performed on one sample.

The composition and methods of the disclosure can be used in genomics. The methods described herein can provide an answer rapidly which is very desirable for this application. The methods and composition described herein can be used in the process of finding biomarkers that may be used for diagnostics or prognostics and as indicators of health and disease. The methods and composition described herein can be used to screen for drugs, e.g., drug development, selection of treatment, determination of treatment efficacy and/or identify targets for pharmaceutical development. The ability to test gene expression on screening assays involving drugs is very important because proteins are the final gene product in the body. In some embodiments, the methods and compositions described herein will measure both protein and gene expression simultaneously which will provide the most information regarding the particular screening being performed.

The composition and methods of the disclosure can be used in gene expression analysis. The methods described herein discriminate between nucleotide sequences. The difference between the target nucleotide sequences can be, for example, a single nucleic acid base difference, a nucleic acid deletion, a nucleic acid insertion, or rearrangement. Such sequence differences involving more than one base can also be detected. The process of the present disclosure is able to detect infectious diseases, genetic diseases, and cancer.

The present methods can be applied to the analysis of biomolecular samples obtained or derived from a patient so as to determine whether a diseased cell type is present in the sample, the stage of the disease, the prognosis for the patient, the ability to the patient to respond to a particular treatment, or the best treatment for the patient. The present methods can also be applied to identify biomarkers for a particular disease.

In some embodiments, the methods described herein are used in the diagnosis of a condition. As used herein the term "diagnose" or "diagnosis" of a condition may include predicting or diagnosing the condition, determining predisposition to the condition, monitoring treatment of the condition, diagnosing a therapeutic response of the disease, or prognosis of the condition, condition progression, or response to particular treatment of the condition. For example, preserved (e.g., FFPE) clinical samples can be assayed according to any of the methods described herein to determine the presence and/or quantity of markers of a disease or malignant cell type in the sample, thereby diagnosing or staging a disease or a cancer.

In some embodiments, the methods and composition described herein are used for the diagnosis and prognosis of a condition. Numerous immunologic, proliferative and malignant diseases and disorders are especially amenable to the methods described herein. Immunologic diseases and disorders include allergic diseases and disorders, disorders of immune function, and autoimmune diseases and conditions. Allergic diseases and disorders include but are not limited to allergic rhinitis, allergic conjunctivitis, allergic asthma, atopic eczema, atopic dermatitis, and food allergy. Immunodeficiencies include but are not limited to severe combined immunodeficiency (SCID), hypereosinophilic syndrome, chronic granulomatous disease, leukocyte adhesion deficiency I and II, hyper IgE syndrome, Chediak Higashi, neutrophilias, neutropenias, aplasias, Agammaglobulinemia, hyper-IgM syndromes, DiGeorge/Velocardial-facial syndromes and Interferon gamma-TH1 pathway defects. Autoimmune and immune dysregulation disorders include but are not limited to rheumatoid arthritis, diabetes, systemic lupus erythematosus, Graves' disease, Graves ophthalmopathy, Crohn's disease, multiple sclerosis, psoriasis, systemic sclerosis, goiter and struma lymphomatosa (Hashimoto's thyroiditis, lymphadenoid goiter), alopecia aerata, autoimmune myocarditis, lichen sclerosis, autoimmune uveitis, Addison's disease, atrophic gastritis, myasthenia gravis, idiopathic thrombocytopenic purpura, hemolytic anemia, primary biliary cirrhosis, Wegener's granulomatosis, polyarteritis nodosa, and inflammatory bowel disease, allograft rejection and tissue destructive from allergic reactions to infectious microorganisms or to environmental antigens.

Proliferative diseases and disorders that may be evaluated by the methods of the disclosure include, but are not limited to, hemangiomatosis in newborns; secondary progressive multiple sclerosis; chronic progressive myelodegenerative disease; neurofibromatosis; ganglioneuromatosis; keloid formation; Paget's Disease of the bone; fibrocystic disease (e.g., of the breast or uterus); sarcoidosis; Peronies and Duputren's fibrosis, cirrhosis, atherosclerosis and vascular restenosis.

Malignant diseases and disorders that may be evaluated by the methods of the disclosure include both hematologic malignancies and solid tumors.

Hematologic malignancies are especially amenable to the methods of the disclosure when the sample is a blood sample, because such malignancies involve changes in blood-borne cells. Such malignancies include non-Hodgkin's lymphoma. Hodgkin's lymphoma, non-B cell lymphomas, and other lymphomas, acute or chronic leukemias, polycythemias, thrombocythemias, multiple myeloma, myelodysplastic disorders, myeloproliferative disorders, myelofibroses, atypical immune lymphoproliferations and plasma cell disorders.

Plasma cell disorders that may be evaluated by the methods of the disclosure include multiple myeloma, amyloidosis and Waldenstrom's macroglobulinemia.

Example of solid tumors include, but are not limited to, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

Genetic diseases can also be detected by the process of the present disclosure. This can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

The methods described herein can be used to diagnose pathogen infections, for example infections by intracellular bacteria and viruses, by determining the presence and/or quantity of markers of bacterium or virus, respectively, in the sample.

A wide variety of infectious diseases can be detected by the process of the present disclosure. The infectious diseases can be caused by bacterial, viral, parasite, and fungal infectious agents. The resistance of various infectious agents to drugs can also be determined using the present disclosure.

Bacterial infectious agents which can be detected by the present disclosure include *Escherichia coli, Salmonella, Shigella, Klesbiella, Pseudomonas, Listeria monocytogenes, Mycobacterium tuberculosis, Mycobacterium aviumintracellulare, Yersinia, Francisella, Pasteurella, Brucella, Clostridia, Bordetella pertussis, Bacteroides, Staphylococcus aureus, Streptococcus pneumonia, B-Hemolytic* strep., *Corynebacteria, Legionella, Mycoplasma, Ureaplasma, Chlamydia, Neisseria gonorrhea. Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia*, and *Acitnomycetes*.

Fungal infectious agents which can be detected by the present disclosure include *Cryptococcus neoformans, Blastomyces dermatitidis, Histoplasma capsulatum, Coccidioides immitis, Paracoccidioides brasiliensis, Candida albicans, Aspergillus fumigautus, Phycomycetes (Rhizopus), Sporothrix schenckii, Chromomycosis*, and *Maduromycosis*.

Viral infectious agents which can be detected by the present disclosure include human immunodeficiency virus, human T-cell lymphocytotrophic virus, hepatitis viruses (e.g., Hepatitis B Virus and Hepatitis C Virus), Epstein—Barr virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present disclosure include *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidium, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis, trematodes, Diphyllobothrium latum, Taenia* spp., *Pnemocystis carinii*, and *Necator americanis*.

The present disclosure is also useful for detection of drug resistance by infectious agents. For example, vancomycin-resistant *Enterococcus/faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus can all be identified with the present disclosure Thus, the target molecules detected using the compositions and methods of the disclosure can be either patient markers (such as a cancer marker) or markers of infection with a foreign agent, such as bacterial or viral markers.

The compositions and methods of the disclosure can be used to identify and/or quantify a target molecule whose abundance is indicative of a biological state or disease condition, for example, blood markers that are upregulated or downregulated as a result of a disease state.

In some embodiments, the methods and compositions of the present disclosure can be used for cytokine expression. The low sensitivity of the methods described herein would be helpful for early detection of cytokines, e.g., as biomarkers of a condition, diagnosis or prognosis of a disease such as cancer, and the identification of subclinical conditions.

The different samples from which the target polynucleotides are derived can comprise multiple samples from the same individual, samples from different individuals, or combinations thereof. In some embodiments, a sample comprises a plurality of polynucleotides from a single individual. In some embodiments, a sample comprises a plurality of polynucleotides from two or more individuals. An individual is any organism or portion thereof from which target polynucleotides can be derived, non-limiting examples of which include plants, animals, fungi, protists, monerans, viruses, mitochondria, and chloroplasts. Sample polynucleotides can be isolated from a subject, such as a preserved (e.g., FFPE) cell sample, preserved (e.g., FFPE) tissue sample, or organ sample derived therefrom, including, for example, tissue or tumor biopsy. The subject may be an animal, including but not limited to, an animal such as a cow, a pig, a mouse, a rat, a chicken, a cat, a dog, etc., and is in some cases a mammal, such as a human. Samples can also be artificially derived, such as by chemical synthesis. In some embodiments, the samples comprise DNA. In some embodiments, the samples comprise genomic DNA. In some embodiments, the samples comprise mitochondrial DNA, chloroplast DNA, plasmid DNA, bacterial artificial chromosomes, yeast artificial chromosomes, oligonucleotide tags, or combinations thereof. In some embodiments, the samples comprise DNA generated by primer extension reactions using any suitable combination of primers and a DNA polymerase, including but not limited to polymerase chain reaction (PCR), reverse transcription, and combinations thereof. Where the template for the primer extension reaction is RNA, the product of reverse transcription is referred to as complementary DNA (cDNA). Primers useful in primer extension reactions can comprise sequences specific to one or more targets, random sequences, partially random sequences, and combinations thereof. Reaction conditions suitable for primer extension reactions are known in the art. In general, sample polynucleotides comprise any polynucleotide present in a sample, which may or may not include target polynucleotides.

Methods for the extraction and purification of nucleic acids are well known in the art. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, California); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). In some embodiments, the above isolation methods may be preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic isolation step, purification of nucleic acids can be performed after any step in the methods of the disclosure, such as to remove excess or unwanted reagents, reactants, or products. Nucleic acid template molecules can be obtained as described in U.S. Patent Application Publication Number US2002/0190663 A1, published Oct. 9, 2003. Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). In some cases, the nucleic acids can be first extract from the biological samples and then crosslinked in vitro. In some cases, native association proteins (e.g. histones) can be further removed from the nucleic acids.

Extraction and Recovery of Native Chromatin

Provided herein are methods for extracting long fragment lengths and/or phase information-containing fragments from preserved samples (e.g., FFPE samples). In some cases, these methods involve treating the nuclei of preserved cells (e.g., FFPE cells) gently in order to preserve the chromatin structures already present in the preserved sample (e.g., FFPE sample).

Disclosed herein are methods for performing extraction and in situ library preparation for the preservation of long range DNA fragments and/or phase information containing fragments. The released DNA can then further processed for analysis, such as being used to generate read-pair libraries.

A preserved sample (such as an FFPE sample) can be treated with a dissolving agent to dissolve embedding material (e.g., paraffin). In some cases, the dissolving agent is a solvent, such as xylene. Other examples of suitable solvent agents include but are not limited to organic solvents such as xylene, toluene, and benzene, as well as suitable isomers of each. The composition can be mixed such that the embedding material is dissolved in the dissolving agent. In some cases, mixing involves vortexing or high speed shaking or agitating. Alternately, gentle agitation is used in some cases. The sample is treated to separate the sample from the solvent and dissolved embedding material, such as through centrifugation with sufficient speed as to pellet the sample. Sufficient speeds include, but are not limited to, maximum speed of a table top centrifuge, such at 14,000 revolutions per minute. The dissolving agent, comprising the dissolved embedding material, then can be removed, often gently so as not to disturb the pellet. Excess dissolving agent then can be removed with a washing reagent. In some examples, the washing agent is ethanol, for example 100% ethanol. The sample is mixed, vortexed, or agitated to dislodge the sample pellet from the inner wall of the holding vessel. The sample can optionally be re-centrifuged to re-pellet. Any remaining liquid is then removed from the holding vessel and the sample is dried. Representative drying techniques include air drying, vacuum drying, or other drying techniques well known in the art. After drying, a buffer, such as a lysis buffer is added to the sample. Lysis buffer can comprise buffering agents such as tris, salts such as sodium chloride, one or more detergents, such as sodium dodecyl sulfate (SDS), triton, a chelating agent, such as EDTA, and any combination thereof. A representative lysis buffer comprises 50 mM Tris pH 8, 50 mM NaCl, 1% SDS, 0.15% Triton, 1 mM EDTA, though one of skill in the art understands that variants on this composition may be readily generated. Suitable protocols can be employed to remove other embedding agents.

The sample can be allowed to rehydrate, such as by incubating (e.g., at 37° C.) for a sufficient amount of time, optionally while shaking or gently agitating. The sample then can be agitated, pipetted, or otherwise mixed in order to break up and re-suspend the pellet in the lysis buffer. Remaining non-soluble debris then can be separated from the lysis buffer, such as by centrifugation at a sufficient speed. DNA-protein complexes can be recovered and evaluated using downstream techniques, such as techniques to tag nucleic acid fragments.

Native DNA:protein complexes (e.g., chromatin) can be isolated from preserved samples (e.g., FFPE samples) such that the complexes rather than the nucleic acids are preserved intact. In these approaches, nucleic acid physical linkage information can be preserved not necessarily by preserving the nucleic acid phosphodiester backbones, but by preserving the linkage information independent of phosphodiester backbone status, such that commonly tagged fragments of a complex can be inferred to have a structural or physical linkage arrangement in the original sample.

Solubilization of chromatin can be an important step in isolating native DNA:protein complexes and extracting long-range linkage information from preserved samples such as FFPE samples. Chromatin complexes can be solubilized through a variety of methods, including but not limited to proteinase digestion and sonication. Such solubilization methods can disrupt tissue and chromatin to release soluble chromatin.

Solubilization via proteinase digestion can employ a variety of proteinase enzymes (also known as peptidase or protease enzymes), including but not limited to one or more of proteinase K, endoproteinase trypsin, chymotrypsin, endoproteinase Asp-N, endoproteinase Arg-C, endoproteinase Glu-C, endoproteinase Lys-C, thermolysin, papain, subtilisin, clostripain, carboxypeptidase B, carboxypeptidase P, carboxypeptidase Y, cathepsin C, acylamino-acid-releasing enzyme, and pyroglutamate aminopeptidase. Proteinase enzymes can be serine proteases, cysteine proteases, threonine proteases, aspartic proteases, glutamic proteases, metalloproteases, or asparagine peptide lyases.

An exemplary protocol for solubilization via proteinase digestion can include removal of embedding material (e.g., paraffin), proteinase digestion, recovery of solubilized chromatin (e.g., with carboxylated beads such as SPRI beads), and sequencing library preparation. For example, first, tissue material can be put into a tube (e.g., 1.5 mL Eppendorf tube). Then, embedding material (e.g., paraffin) can be dissolved using a solvent such as xylene, Hemo-De, or limonene. Ethanol (e.g., 100% EtOH) can be used to remove the solvent, and the sample can be dried to remove the ethanol. The sample can then be digested with a proteinase enzyme (e.g., proteinase K). This can result in most or all of the tissue sample being solubilized. Without being limited by theory, proteinase treatment can be effective because protein-DNA methylene crosslink reversal can be very minor during the conditions of a proteinase treatment (e.g., 1 hour at 37° C.).

An exemplary protocol for solubilization via sonication can include removal of embedding material (e.g., paraffin), lysis, homogenization, sonication, recovery of solubilized chromatin (e.g., with carboxylated beads such as SPRI beads), and sequencing library preparation. For example, first, embedding material (e.g., paraffin) can be dissolved using a solvent such as xylene. Hemo-De, or limonene. The tissue specimen can then be rehydrated, for example in successive washes of different ethanol concentrations from 100% ethanol to pure water. The tissue material can then be put into a tube and incubated in a lysis buffer (e.g., for one hour). Tissue can then be re-suspended in a buffer, such as a digestion buffer (e.g., MNase digestion buffer). The sample can then be homogenized, by methods including but not limited to Dounce homogenization. The sample can then be sonicated and re-suspended in a sonication buffer. Sonication cycles (e.g., 30 seconds at highest power) can then be repeated for as many cycles as needed to obtain sufficient solubilized chromatin (e.g., 10 cycles, 20 cycles, 30 cycles, 40 cycles). The soluble fraction can then be recovered.

Following solubilization, the sample can then be further processed according to methods discussed herein, such as recovery of solubilized chromatin (e.g., by binding to solid phase reversible immobilization (SPRI) beads), preparation of a sequencing library, such as a Chicago library as described herein (e.g., cleaving, tagging, and ligating of nucleic acids), sequencing (e.g., including long-range information), and sequence assembly.

Size Selection

Nucleic acid obtained from preserved (e.g., FFPE) biological samples can be fragmented to produce suitable fragments for analysis. Template nucleic acids may be fragmented or sheared to desired length, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In some embodiments, nucleic acid from a biological sample is fragmented by sonication. In other embodiments, nucleic acid is fragmented by a hydroshear instrument. Generally, individual nucleic acid template molecules can be from about 2 kb bases to about 40 kb. In various embodiments, nucleic acids can be about 6 kb-10 kb fragments. Nucleic acid molecules may be single-stranded, double-stranded, or double-stranded with single-stranded regions (for example, stem- and loop-structures).

In some embodiments, crosslinked DNA molecules may be subjected to a size selection step. Size selection of the nucleic acids may be performed to crosslinked DNA molecules below or above a certain size. Size selection may further be affected by the frequency of crosslinks and/or by the fragmentation method, for example by choosing a frequent or rare cutter restriction enzyme. In some embodiments, a composition may be prepared comprising crosslinking a DNA molecule in the range of about 1 kb to 5 Mb, about 5 kb to 5 Mb, about 5 kB to 2 Mb, about 10 kb to 2 Mb, about 10 kb to 1 Mb, about 20 kb to 1 Mb about 20 kb to 500 kb, about 50 kb to 500 kb, about 50 kb to 200 kb, about 60 kb to 200 kb, about 60 kb to 150 kb, about 80 kb to 150 kb, about 80 kb to 120 kb, or about 100 kb to 120 kb, or any range bounded by any of these values (e.g. about 150 kb to 1 Mb).

In some embodiments, sample polynucleotides are fragmented into a population of fragmented DNA molecules of one or more specific size range(s). In some embodiments, fragments can be generated from at least about 1, about 2, about 5, about 10, about 20, about 50, about 100, about 200, about 500, about 1000, about 2000, about 5000, about 10,000, about 20,000, about 50,000, about 100.000, about 200,000, about 500,000, about 1,000,000, about 2,000,000, about 5,000,000, about 10,000,000, or more genome-equivalents of starting DNA. Fragmentation may be accomplished by methods known in the art, including chemical, enzymatic, and mechanical fragmentation. In some embodiments, the fragments have an average length from about 10 to about 10,000, about 20,000, about 30,000, about 40,000, about 50,000, about 60,000, about 70,000, about 80,000, about 90,000, about 100,000, about 150,000, about 200,000, about 300,000, about 400,000, about 500,000, about 600, 000, about 700,000, about 800,000, about 900,000, about 1,000,000, about 2,000,000, about 5,000,000, about 10,000, 000, or more nucleotides. In some embodiments, the fragments have an average length from about 1 kb to about 10 Mb. In some embodiments, the fragments have an average length from about 1 kb to 5 Mb, about 5 kb to 5 Mb, about 5 kB to 2 Mb, about 10 kb to 2 Mb, about 10 kb to 1 Mb, about 20 kb to 1 Mb about 20 kb to 500 kb, about 50 kb to 500 kb, about 50 kb to 200 kb, about 60 kb to 200 kb, about 60 kb to 150 kb, about 80 kb to 150 kb, about 80 kb to 120 kb, or about 100 kb to 120 kb, or any range bounded by any of these values (e.g. about 60 to 120 kb). In some embodiments, the fragments have an average length less than about 10 Mb, less than about 5 Mb, less than about 1 Mb, less than about 500 kb, less than about 200 kb, less than about 100 kb, or less than about 50 kb. In other embodiments, the fragments have an average length more than about 5 kb, more than about 10 kb, more than about 50 kb, more than about 100 kb, more than about 200 kb, more than about 500 kb, more than about 1 Mb, more than about 5 Mb, or more than about 10 Mb. In some embodiments, the fragmentation is accomplished mechanically comprising subjection sample DNA molecules to acoustic sonication. In some embodiments, the fragmentation comprises treating the sample DNA molecules with one or more enzymes under conditions suitable for the one or more enzymes to generate double-stranded nucleic acid breaks. Examples of enzymes useful in the generation of DNA fragments include sequence specific and non-sequence specific nucleases. Non-limiting examples of nucleases include DNase I, Fragmentase, restriction endonucleases, variants thereof, and combinations thereof. For example, digestion with DNase I can induce random double-stranded breaks in DNA in the absence of $Mg^{++}$ and in the presence of $Mn^{++}$. In some embodiments, fragmentation comprises treating the sample DNA molecules with one or more restriction endonucleases. Fragmentation can produce fragments having 5' overhangs, 3' overhangs, blunt ends, or a combination thereof. In some embodiments, such as when fragmentation comprises the use of one or more restriction endonucleases, cleavage of sample DNA molecules leaves overhangs having a predictable sequence. In some embodiments, the method includes the step of size selecting the fragments via standard methods such as column purification or isolation from an agarose gel.

Sequencing Library Preparation

Figure 1B:
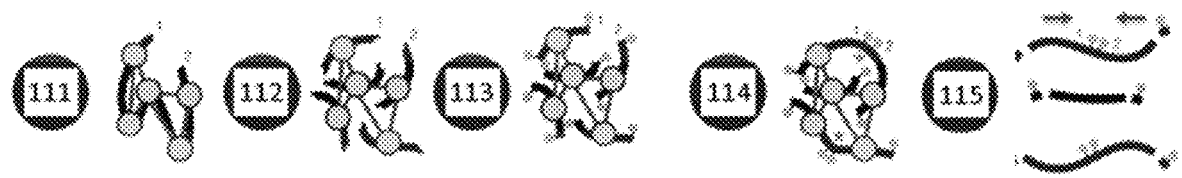
FIG. 1B depicts an exemplary schematic of a protocol for chromatin-based next generation sequencing (NGS) library preparation.

FIG. 1B shows an exemplary schematic of chromatin-based next generation sequencing (NGS) library preparation (e.g., "Chicago"). In a first step 111, chromatin nucleases (blue circles) are crosslinked (red lines) forming chromatin aggregates. In a second step 112, chromatin aggregates are cut with restriction endonuclease. In a third step 113, cut ends are blunt ended, ligated, and marked (e.g., with biotin) (small green circles). In a fourth step 114, blunt ends are randomly ligated forming short, medium, and long-range associations (red asterisks indicate ligation events). In a fifth step (115), crosslinks are reversed, DNA is purified, and informative ligation-containing fragments are selected for with marker pulldown. Then, a conventional sequencing library preparation can be performed. Resulting read pairs can span genomic distances up to the maximum size of the input DNA. Such libraries can be used to construct highly-contiguous genome assemblies with chromosome-scale super-scaffolds.

Figure 1C:
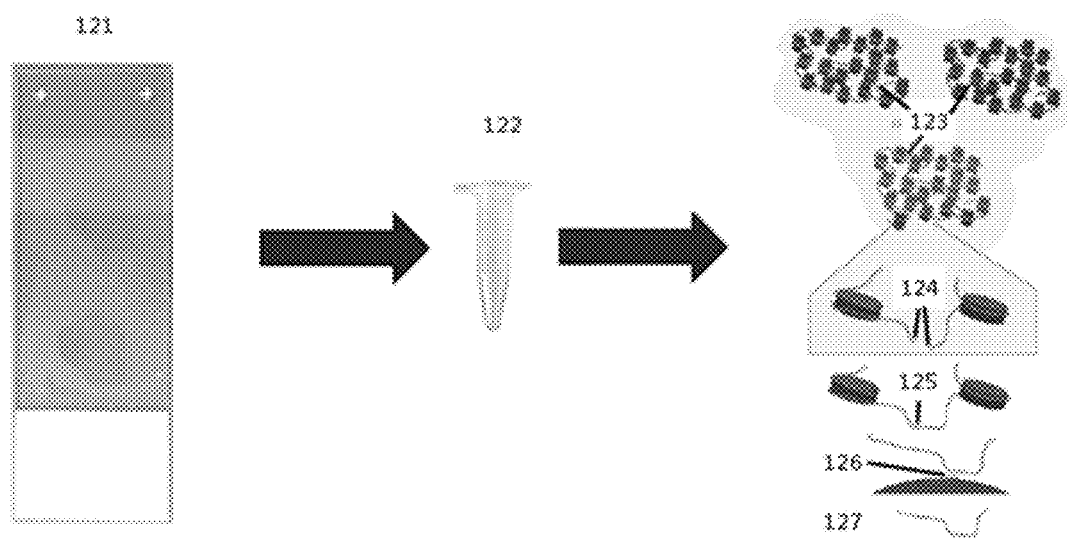
FIG. 1C shows an exemplary schematic of a workflow for chromatin extraction and library preparation (e.g., Chicago library preparation) from a preserved sample (e.g., an FFPE sample).

FIG. 1C shows an exemplary schematic of a workflow for chromatin extraction and library preparation (e.g., Chicago library preparation) from a preserved sample (e.g., an FFPE sample). Preserved samples can be processed to extract fixed chromatin that can then be put through methods for generating and sequencing long range genomic linkage information. For example, a preserved sample 121 can have chromatin extracted 122 and fragmented (e.g., with a restriction enzyme, such as DpnII). The chromatin can comprise crosslinks 123. Overhangs (e.g., 4 bp 5 overhangs) can be filled in with a nucleotide mix including biotinylated nucleotides 124. Blunt ends can then be ligated 125, and markers (e.g., biotin) can be pulled down (e.g., using streptavidin) 126. Non-marked (e.g., non-biotinylated) blunt ends can then be removed, and sequencing adapters (e.g., Illumina sequencing adapters, Pacific Biosciences sequencing adapters, nanopore sequencing adapters) can be attached and a sequencing library 127 can be prepared. The library can be enriched for molecules containing biotinylated ligated junctions, amplified (e.g., by PCR), and sequenced (e.g., using an Illumina sequencer such as a MiSeq or HiSeq, using a Pacific Biosciences long-read sequencer, or using a nanopore sequencer such as Oxford Nanopore or Genia). In some cases, such as when using a long-read sequencer like Pacific Biosciences or nanopore sequencers, multiple molecules can be joined (e.g., ligated) into a longer molecule prior to sequencing.

Enrichment can be performed, alternatively or in addition to enrichment for labeled nucleotides (e.g., biotinylated nucleotides, epigenetically modified nucleotides), for genetic regions of interest. For example, a sample or a library can be enriched for a fusion gene, such as by targeting a known relevant half of a fusion gene. Other genetic and genomic features as discussed herein can also be targeted for enrichment.

In many cases, no fixative agent is added to the previously obtained sample (such as an FFPE sample) as part of the purification process. Rather, crosslinks previously generated pursuant to an original sample preservation process can be relied upon to stabilize the DNA-protein (e.g., chromatin) complexes isolated herein, and the extraction process preserves linked complexes rather than generating substantial amounts of new ones. The fraction of the sample solubilized in the lysis buffer is then processed by any of the methods disclosed herein.

Alternatively, in some embodiments, in vitro proximity ligation (e.g., Chicago in vitro proximity ligation) or other protein-DNA complex tagging methods are used to generate read-pair libraries from reconstituted chromatin generated from high quality nucleic acids extracted from preserved samples (such as FFPE preserved samples) comprising DNA. For example, a preserved sample (e.g., an FFPE sample) can be processed to extract nucleic acids such as DNA so as to minimize DNA damage in the extraction process. In some cases, one or more of vortexing, shearing, boiling, high-temperature incubation or DNase-related enzymatic treatment are excluded from the nucleic acid extraction protocol, so as to decrease the damage to isolated naked DNA. The isolated DNA recovered can be of quality sufficient to preserve physical linkage, phase, or genome structural information. Extracted nucleic acids can be diluted and used to generate reconstituted chromatin (e.g., using methods such as those taught in PCT Publication No. WO2014/121091, published Aug. 7, 2014, which is hereby incorporated by reference in its entirety, or in PCT Publication No. WO2016/019360, published Feb. 4, 2016, which is hereby incorporated by reference in its entirety), such that DNA:protein complexes comprise a single DNA molecule and at least one DNA binding moiety. The reconstituted chromatin can be crosslinked, such as with formaldehyde, in order to preserve proximal information of DNA sequences within the same DNA molecule, independent of their common phosphodiester backbone. Importantly, the crosslinking can be performed on the DNA extracted from the preserved sample (such as an FFPE sample) after isolation from the preserved sample. As discussed above in the context of isolation of DNA-protein complexes, in many cases no crosslinking agent is added during the isolation process. These crosslinked reconstituted complexes can be labeled, such as with biotin, methylation, sulfylation, acetylation, or other base modification, and then isolated, such as with streptavidin beads in the case of biotin labelling. The isolated complexes then can be digested with restriction enzymes in order to generate free sticky ends which are then filled in with labelled nucleotides, such as with biotinylated nucleotides or other nucleotides as mentioned.

Exposed DNA ends in DNA:protein complexes, whether pre-existing (e.g., from degradation of a preserved sample) or a result of a protocol disclosed herein (e.g., enzymatic or physical cleavage), can be ligated to generate paired ends between DNA sequences within the same DNA molecule. These ligated paired ends can often be originally not adjacent to one another on the DNA molecule. Paired ends can be blunt, in some cases as a result of filling in sticky ends.

Alternately or additionally, exposed nucleic acid complex ends can be ligated to one another through a punctuation oligonucleotide as discussed herein, or can be tagged using a population of oligonucleotide tags such that nucleic acid fragments are identifiably mapped to a common DNA protein complex. In some cases, paired end reads are generated not from cleaved ends of a DNA-complex that are directly ligated, but from cleaved ends that are joined to a common punctuation oligonucleotide. A punctuation oligonucleotide includes any oligonucleotide that can be joined to a target polynucleotide, so as to bridge two cleaved internal ends of a sample molecule undergoing phase-preserving rearrangement. Punctuation oligonucleotides can comprise DNA, RNA, nucleotide analogues, non-canonical nucleotides, labeled nucleotides, modified nucleotides, or combinations thereof. In many examples, double-stranded punctuation oligonucleotides comprise two separate oligonucleotides hybridized to one another (also referred to as an "oligonucleotide duplex"), and hybridization may leave one or more blunt ends, one or more 3' overhangs, one or more 5' overhangs, one or more bulges resulting from mismatched and/or unpaired nucleotides, or any combination of these. In some instances, different punctuation oligonucleotides are joined to target polynucleotides in sequential reactions or simultaneously. For example, the first and second punctuation oligonucleotides can be added to the same reaction. Alternately, punctuation oligo populations are uniform in some cases. Punctuation molecule and methods of use in preserving and determining genomic structural and proximity information has been described previously (U.S. provisional application Nos. 62/298,906, 62/298,966, and 62/305,957, all three of which are incorporated herein in their entirety). Some punctuation oligonucleotides comprise a tag or label to facilitate isolation, such as a biotin tag, such that fragments of a library comprising punctuation oligonucleotides are easily isolated. Alternative tags include but are not limited to methylation, acetylation, or other base modification. Generally, punctuation oligonucleotides are ligated to exposed nucleic acid ends, but alternate approaches of incorporating punctuation oligonucleotides into a library are also contemplated.

Nucleotides, such as those used to fill in sticky ends, can be labeled. Labelled nucleotides can biotinylated, sulphated, attached to a fluorophore, dephosphorylated, or any other number of nucleotide modifications. Nucleotide modifications can also include epigenetic modifications, such as methylation (e.g., 5-mC, 5-hmC, 5-fC, 5-caC, 4-mC, 6-mA, 8-oxoG, 8-oxoA). Labels or modifications can be selected from those detectable during sequencing, such as epigenetic modifications detectable by nanopore sequencing; in this way, the locations of ligation junctions can be detected during sequencing. These labels or modifications can also be targeted for binding or enrichment; for example, antibodies targeting methyl-cytosine can be used to capture, target, bind, or label blunt ends filled in with methyl-cytosine. Non-natural nucleotides, non-canonical or modified nucleotides, and nucleic acid analogs can also be used to label the locations of blunt-end fill-in. Non-canonical or modified nucleotides can include pseudouridine ($\Psi$), dihydrouridine (D), inosine (I), 7-methylguanosine (m7G), xanthine, hypoxanthine, purine, 2,6-diaminopurine, and 6,8-diaminopurine. Nucleic acid analogs can include peptide nucleic acid (PNA), Morpholino and locked nucleic acid (LNA), glycol nucleic acid (GNA), and threose nucleic acid (TNA). In some cases, overhangs are filled in with un-labeled dNTPs, such as dNTPs without biotin. In some cases, such as cleavage with a transposon, blunt ends are generated that do not require filling in. These free blunt ends are generated when the transposase inserts two unlinked punctuation oligonucleotides. The punctuation oligonucleotides, however, can be synthesized to have sticky or blunt ends as desired. Proteins associated with sample nucleic acids, such as histones, can also be modified. For example, histones can be acetylated (e.g., at lysine residues) and/or methylated (e.g., at lysine and arginine residues).

In some embodiments, Hi-C or other ligation or tagging-mediated methods can be used to generate read-pair libraries from naturally occurring chromatin that is crosslinked, for example chromatin that is crosslinked pursuant to sample preservation. The DNA can be crosslinked, such as with formaldehyde, to preserve native chromatin structures during the preservation process. Extraction can be performed as above to separate these DNA-protein structures from any sample preservative or fixative such as paraffin, without disrupting the crosslinked DNA-protein structures, thereby preserving proximal information between DNA molecules independent of a phosphodiester backbone. These crosslinked structures can be digested with a restriction enzyme to generate free sticky ends which are subsequently filled in with tagged nucleotides, such as biotin labelled nucleotides. The resulting blunt ends can be ligated together to generate paired ends of DNA fragments. These paired ends represent DNA molecules that are in proximity to each other in the chromatin structure. Hi-C methods and variations are known in the art (Liberman-Aiden et al., 2009, Science 326, 289, incorporated herein in its entirety; US2013009009, incorporated herein in its entirety).

The paired ends can be released from the chromatin protein, such as by enzymatic digestion (e.g., with a proteinase such as proteinase K). Released paired ends can be treated with an exonuclease to remove labelled nucleotides from remaining free ends, such that the only labelled nucleotides reside between the ligated paired ends. These paired ends then can be purified, such as with streptavidin beads in the case of biotin labels. Purification can also be conducted by other means, such as with SPRI beads (e.g., carboxylated beads) or via electrophoresis (e.g., gel electrophoresis, capillary electrophoresis). Paired ends then can be prepared for sequencing. For example, the paired ends can be attached to sequencing adapters and then sequenced to generate read pair libraries. Chicago in vitro proximity ligation methods have been described previously (see, e.g., U.S. Pat. Pub. No. 20140220587, incorporated herein by reference in its entirety; U.S. Pat. Pub. No. 20150363550, incorporated herein by reference in its entirety).

In an exemplary embodiment, a library is created from cells previously embedded in FFPE, in sections 15-20 microns thick having about $3 \times 10^5$ cells per section. Alternatively, cells embedded in FFPE are provided in sections 1-5, 5-10, 10-15, 15-20, 25-30, 35-40, or 45-50 thick having about 103, 104, $10^5$, 10, or $10^7$ cells per section. In some cases, the samples are AJ GIAB ('Genome In A Bottle') samples GM24149 (father) and GM24385 (son). The sections are washed with a solvent to remove the embedding material, for example xylene, toluene, or benzene. The solvent is removed by washing the sections with an ethanol solutions, in some cases 100% ethanol is used to wash the sections. The paraffin-free tissue samples are then solubilized in a buffer, for example in a detergent buffer. Nucleic acids in the samples are then digested with an endonuclease, for example a restriction enzyme such as Mbo1. Blunt ends are created in the digested nucleic acids by filling in the overhangs resulting from the restriction enzyme digest using a DNA polymerase and nucleotides, such as biotinylated dNTPs. The blunt ends are ligated together using a DNA ligase, for example T4 DNA ligase in a reaction favoring blunt end ligation, resulting in biotinylated fragments of DNA. These fragments are prepared for use in a sequencing reaction.

Sequencing

Also disclosed herein are methods and compositions for generating nucleic acid sequencing libraries that harbor genomic structural information such as physical linkage information. DNA complexes are generated from preserved samples such as FFPE derived nucleic acid samples. Paired ends, ligation junctions, punctuation ends or commonly tagged ends are generated through the isolation of nucleic acid complexes bound such that a first segment and a second segment are held together independently of any phosphodiester backbone bond, exposed ends are tagged, and tag junctions are isolated. Tagging variously comprises tagging one exposed end using a second exposed end directly, such that the junction is identifiable from the fact that sequences on either side of the junction map to contigs that correspond to distal positions on a genome scaffold, are unscaffolded, or map to different chromosomes in an unrearranged genome. Alternately, tagging involves joining exposed ends using a punctuation oligo, or adding a common oligo tag to exposed ends of a complex such that sequence adjacent to tagged ends is confidently mapped to a common DNA complex and therefore a common phase of a source nucleic acid from which the DNA complex was generated.

Paired ends, concatamerized paired ends, or punctuated molecules are sequenced using an appropriate short read or long read sequencing technology platform, and the sequence reads are then analyzed.

In some cases, a plurality of paired end molecules is generated as described herein, and subsequently sequenced using short read sequencing technology. In these cases, either short sequence reads across the paired end ligation junction are generated, or short reads from each end of the paired end fragment are generated to make a read pair. If sequences from the first and second nucleic acid segments are detected in a single sequence read or read pair, it is determined that the first and second nucleic acid segments are in phase on the same DNA molecule in the input DNA sample. In such cases, the generated sequence libraries yield phase and structural information for DNA segments.

For a given punctuated molecule sequence read or read pair, sequence segments are observed that are locally uninterrupted by punctuation elements. Sequence in these segments is presumed to be in phase, and locally correctly ordered and oriented. Segments are observed to be separated by punctuation oligos. Segments on either side of a punctuation oligo are inferred to be in phase with one another on a common sample nucleic acid molecule but not to be correctly ordered and oriented relative to one another on the punctuation molecule. A benefit of the rearrangement is that segments positioned far removed from one another are sometimes brought into proximity, such that they are read in a common read and confidently assigned to a common phase even if in the sample molecule they are separated by large distances of identical, difficult to phase sequence. Another benefit is that the segment sequences themselves comprise most, substantially all or all of the original sample sequence, such that in addition to phase information, in some cases contig information is determined sufficient to perform de novo sequence assembly in some cases. This de novo sequence is optionally used to generate a novel scaffold or contig set, or to augment a previously or independently generated contig or scaffold sequence set.

In some cases, a plurality of punctuated DNA molecules is generated as disclosed herein, concatamerized into a single long nucleic acid molecule or preserved without shearing or cleavage as a single, rearranged long molecule, and subsequently sequenced using long-read sequencing technology. Each punctuated molecule is sequenced, and the sequence reads are analyzed. In preferred examples, sequence reads average 10 kb for the sequence reaction. In other examples, sequence reads average about 5 kb, 6 kb, 7 kb, 8 kb, 9 kb, 10 kb, 11 kb, 12 kb, 13 kb, 14 kb, 15 kb, 16 kb, 17 kb, 18 kb, 19 kb, 20 kb, 21 kb, 22 kb, 25 kb, 30 kb, 35 kb, 40 kb, or greater. In favored examples, sequence reads are identified that comprise at least 500 bases of a first segment and 500 bases of a second segment, joined by a punctuation oligo sequence. In other examples, the sequence reads comprise at least about 100 bases, 200 bases, 300 bases, 400 bases, 500 bases, 600 bases, 700 bases, 800 bases, 900 bases, 1000 bases, or greater of a first DNA segment and at least about 100 bases, 200 bases, 300 bases, 400 bases, 500 bases, 600 bases, 700 bases, 800 bases, 900 bases, 1000 bases, or greater of a second DNA segment. In some examples, the first and second segment sequences are mapped to a scaffold genome and are found to map to contigs that are separated by at least 100 kb. In other examples, the separation distance is 8 kb, 9 kb, 10 kb, 12.5 kb, 15 kb, 17.5 kb, 20 kb, 25 kb, 30 kb, 35 kb, 40 kb, 45 kb, 50 kb, 60 kb, 70 kb, 80 kb, 90 kb, 100 kb, 125 kb, 150 kb, 200 kb, 300 kb, 400 kb, 500 kb, 600 kb, 700 kb, 800 kb, 900 kb, 1 Mb, or greater. In most cases, the first contig and the second contig each comprise a single heterozygous position, the phase of which is not determined in a scaffold. In preferred examples, the heterozygous position of the first contig is spanned by the first segment of the long read, and the heterozygous position of the second contig is spanned by the second segment of the long read. In such cases, the reads each span their contigs' respective heterozygous regions and sequence of the read segments indicates that a first allele of the first contig and a first allele of the second contig are in phase. If sequences from the first and second nucleic acid segments are detected in a single long sequence read, it is determined that the first and second nucleic acid segments are comprised on the same DNA molecule in the input DNA sample. In these embodiments, nucleic acid sequence libraries generated by the methods and compositions disclosed herein provide phase information for contigs that are positioned far apart from one another on a genome scaffold.

Alternatively, a plurality of paired end molecules is generated as described herein, and subsequently sequenced using long read sequencing technology. In some cases, the average read length for the library is determined to be about 1 kb. In other cases, the average read length for the library is about 100 bp, 200 bp, 300 bp, 400 bp, 500 bp, 600 bp, 700 bp, 800 bp, 900 bp, 1 kb, 1.1 kb, 1.2 kb, 1.3 kb, 1.4 kb, 1.5 kb, or greater. In most examples, paired end molecules comprise a first DNA segment and a second DNA segment that, within the input DNA sample, are in phase and separated by a distance greater than 10 kb. In some examples, the separation distance between two such DNA segments is greater than about 5 kb, 6 kb, 7 kb, 8 kb, 9 kb, 10 kb, 11 kb, 12 kb, 13 kb, 14 kb, 15 kb, 20 kb, 23 kb, 25 kb, 30 kb, 32 kb, 35 kb, 40 kb, 50 kb, 60 kb, 75 kb, 100 kb, 200 kb, 300 kb, 400 kb, 500 kb, 750 kb, 1 Mb, or greater. In most cases, sequence reads are generated from paired end molecules, some of which comprise at least 300 bases of sequence from a first nucleic acid segment and at least 300 bases of sequence from a second nucleic acid segment. In other examples, the sequence reads comprise at least about 50 bases, 100 bases, 150 bases, 200 bases, 250 bases, 300 bases, 350 bases, 400 bases, 450 bases, 500 bases, 550 bases, 600 bases, 650 bases, 70) bases, 750 bases, 800 bases, or greater of a first DNA segment and at least about 50 bases, 100 bases, 150 bases, 200 bases, 250 bases, 300 bases, 350 bases, 400 bases, 450 bases, 500 bases, 550 bases, 600 bases, 650 bases, 700 bases, 750 bases, 800 bases, or greater of a second DNA segment. If sequences from the first and second nucleic acid segments are detected in a single sequence read or read pair, it is determined that the first and second nucleic acid segments are in phase on the same DNA molecule in the input DNA sample. In such cases, the generated sequence libraries yield phase information for DNA segments that are separated in the nucleic acid sample by greater than the read length of the sequencing technology used to sequence them.

In various embodiments, suitable sequencing methods described herein or otherwise known in the art are used to obtain sequence information from nucleic acid molecules within a sample. Sequencing can be accomplished through classic Sanger sequencing methods which are well known in the art. Sequence can also be accomplished using high-throughput systems some of which allow detection of a sequenced nucleotide immediately after or upon its incorporation into a growing strand, such as detection of sequence in real time or substantially real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour; where the sequencing reads can be at least about 50, about 60, about 70, about 80, about 90, about 100, about 120, about 150, about 180, about 210, about 240, about 270, about 300, about 350, about 400, about 450, about 500, about 600, about 700, about 800, about 900, or about 1000 bases per read.

In some embodiments, high-throughput sequencing involves the use of technology available by Illumina's Genome Analyzer IIX, MiSeq personal sequencer, or HiSeq systems, such as those using HiSeq 2500, HiSeq 1500, HiSeq 2000, or HiSeq 100 machines. These machines use reversible terminator-based sequencing by synthesis chemistry. These machine can do 200 billion DNA reads or more in eight days. Smaller systems may be utilized for runs within 3, 2, 1 days or less time.

In some embodiments, high-throughput sequencing involves the use of technology available by ABI Solid System. This genetic analysis platform that enables massively parallel sequencing of clonally-amplified DNA fragments linked to beads. The sequencing methodology is based on sequential ligation with dye-labeled oligonucleotides.

The next generation sequencing can comprise ion semiconductor sequencing (e.g., using technology from Life Technologies (Ion Torrent)). Ion semiconductor sequencing can take advantage of the fact that when a nucleotide is incorporated into a strand of DNA, an ion can be released. To perform ion semiconductor sequencing, a high density array of micromachined wells can be formed. Each well can hold a single DNA template. Beneath the well can be an ion sensitive layer, and beneath the ion sensitive layer can be an ion sensor. When a nucleotide is added to a DNA, H+ can be released, which can be measured as a change in pH. The H+ ion can be converted to voltage and recorded by the semiconductor sensor. An array chip can be sequentially flooded with one nucleotide after another. No scanning, light, or cameras can be required. In some cases, an TON-PROTON™ Sequencer is used to sequence nucleic acid. In some cases, an IONPGM™ Sequencer is used. The Ion Torrent Personal Genome Machine (PGM). The PGM can do 10 million reads in two hours.

In some embodiments, high-throughput sequencing involves the use of technology available by Helicos BioSciences Corporation (Cambridge, Massachusetts) such as the Single Molecule Sequencing by Synthesis (SMSS) method. SMSS is unique because it allows for sequencing the entire human genome in up to 24 hours. Finally, SMSS is described in part in US Publication Application Nos. 20060024711; 20060024678; 20060012793; 20060012784; and 20050100932.

In some embodiments, high-throughput sequencing involves the use of technology available by 454 Lifesciences, Inc. (Branford, Connecticut) such as the PicoTiterPlate device which includes a fiber optic plate that transmits chemiluminescent signal generated by the sequencing reaction to be recorded by a CCD camera in the instrument. This use of fiber optics allows for the detection of a minimum of 20 million base pairs in 4.5 hours.

Methods for using bead amplification followed by fiber optics detection are described in Marguiles, M., et al. "Genome sequencing in microfabricated high-density picolitre reactors", Nature, doi:10.1038/nature03959; and well as in US Publication Application Nos. 20020012930; 20030068629; 20030100102; 20030148344; 20040248161; 20050079510, 20050124022; and 20060078909.

In some embodiments, high-throughput sequencing is performed using Clonal Single Molecule Array (Solexa, Inc.) or sequencing-by-synthesis (SBS) utilizing reversible terminator chemistry. These technologies are described in part in U.S. Pat. Nos. 6,969,488; 6,897,023; 6,833,246; 6,787,308; and US Publication Application Nos. 20040106110; 20030064398; 20030022207; and Constans, A., The Scientist 2003, 17(13).36.

The next generation sequencing technique can comprise real-time (SMRT™) technology by Pacific Biosciences. In SMRT, each of four DNA bases can be attached to one of four different fluorescent dyes. These dyes can be phospho linked. A single DNA polymerase can be immobilized with a single molecule of template single stranded DNA at the bottom of a zero-mode waveguide (ZMW). A ZMW can be a confinement structure which enables observation of incorporation of a single nucleotide by DNA polymerase against the background of fluorescent nucleotides that can rapidly diffuse in an out of the ZMW (in microseconds). It can take several milliseconds to incorporate a nucleotide into a growing strand. During this time, the fluorescent label can be excited and produce a fluorescent signal, and the fluorescent tag can be cleaved off. The ZMW can be illuminated from below. Attenuated light from an excitation beam can penetrate the lower 20-30 nm of each ZMW. A microscope with a detection limit of 20 zepto liters (10" liters) can be created. The tiny detection volume can provide 1000-fold improvement in the reduction of background noise. Detection of the corresponding fluorescence of the dye can indicate which base was incorporated. The process can be repeated.

In some cases, the next generation sequencing is nanopore sequencing (See, e.g., Soni G V and Meller A. (2007) Clin Chem 53: 1996-2001). A nanopore can be a small hole, of the order of about one nanometer in diameter. Immersion of a nanopore in a conducting fluid and application of a potential across it can result in a slight electrical current due to conduction of ions through the nanopore. The amount of current which flows can be sensitive to the size of the nanopore. As a DNA molecule passes through a nanopore, each nucleotide on the DNA molecule can obstruct the nanopore to a different degree. Thus, the change in the current passing through the nanopore as the DNA molecule passes through the nanopore can represent a reading of the DNA sequence. The nanopore sequencing technology can be from Oxford Nanopore Technologies; e.g., a GridlON system. A single nanopore can be inserted in a polymer membrane across the top of a microwell. Each microwell can have an electrode for individual sensing. The microwells can be fabricated into an array chip, with 100,000 or more microwells (e.g., more than 200,000, 300.000, 400,000, 500,000, 600,000, 700,000, 800,000, 900,000, or 1,000,000) per chip. An instrument (or node) can be used to analyze the chip. Data can be analyzed in real-time. One or more instruments can be operated at a time. The nanopore can be a protein nanopore, e.g., the protein alpha-hemolysin, a heptameric protein pore. The nanopore can be a solid-state nanopore made, e.g., a nanometer sized hole formed in a synthetic membrane (e.g., $SiN_x$, or $SiO_2$). The nanopore can be a hybrid pore (e.g., an integration of a protein pore into a solid-state membrane). The nanopore can be a nanopore with integrated sensors (e.g., tunneling electrode detectors, capacitive detectors, or graphene based nano-gap or edge state detectors (see e.g., Garaj et al. (2010) Nature vol. 67, doi, 10.1038/nature09379)). A nanopore can be functionalized for analyzing a specific type of molecule (e.g., DNA, RNA, or protein). Nanopore sequencing can comprise "strand sequencing" in which intact DNA polymers can be passed through a protein nanopore with sequencing in real time as the DNA translocates the pore. An enzyme can separate strands of a double stranded DNA and feed a strand through a nanopore. The DNA can have a hairpin at one end, and the system can read both strands. In some cases, nanopore sequencing is "exonuclease sequencing" in which individual nucleotides can be cleaved from a DNA strand by a processive exonuclease, and the nucleotides can be passed through a protein nanopore. The nucleotides can transiently bind to a molecule in the pore (e.g., cyclodextran). A characteristic disruption in current can be used to identify bases.

Nanopore sequencing technology from GENIA can be used. An engineered protein pore can be embedded in a lipid bilayer membrane. "Active Control" technology can be used to enable efficient nanopore-membrane assembly and control of DNA movement through the channel. In some cases, the nanopore sequencing technology is from NABsys. Genomic DNA can be fragmented into strands of average length of about 100 kb. The 100 kb fragments can be made single stranded and subsequently hybridized with a 6-mer probe. The genomic fragments with probes can be driven through a nanopore, which can create a current-versus-time tracing. The current tracing can provide the positions of the probes on each genomic fragment. The genomic fragments can be lined up to create a probe map for the genome. The process can be done in parallel for a library of probes. A genome-length probe map for each probe can be generated. Errors can be fixed with a process termed "moving window Sequencing By Hybridization (mwSBH)." In some cases, the nanopore sequencing technology is from IBM/Roche. An electron beam can be used to make a nanopore sized opening in a microchip. An electrical field can be used to pull or thread DNA through the nanopore. A DNA transistor device in the nanopore can comprise alternating nanometer sized layers of metal and dielectric. Discrete charges in the DNA backbone can get trapped by electrical fields inside the DNA nanopore. Turning off and on gate voltages can allow the DNA sequence to be read.

The next generation sequencing can in some cases comprise DNA nanoball sequencing (as performed, e.g., by Complete Genomics; see e.g., Drmanac et al. (2010) Science 327: 78-81). DNA can be isolated, fragmented, and size selected. For example, DNA can be fragmented (e.g., by sonication) to a mean length of about 500 bp. Adaptors (Adl) can be attached to the ends of the fragments. The adaptors can be used to hybridize to anchors for sequencing reactions. DNA with adaptors bound to each end can be PCR amplified. The adaptor sequences can be modified so that complementary single strand ends bind to each other forming circular DNA. The DNA can be methylated to protect it from cleavage by a type IIS restriction enzyme used in a subsequent step. An adaptor (e.g., the right adaptor) can have a restriction recognition site, and the restriction recognition site can remain non-methylated. The non-methylated restriction recognition site in the adaptor can be recognized by a restriction enzyme (e.g., AcuI), and the DNA can be cleaved by AcuI 13 bp to the right of the right adaptor to form linear double stranded DNA. A second round of right and left adaptors (Ad2) can be ligated onto either end of the linear DNA, and all DNA with both adapters bound can be PCR amplified (e.g., by PCR). Ad2 sequences can be modified to allow them to bind each other and form circular DNA. The DNA can be methylated, but a restriction enzyme recognition site can remain non-methylated on the left Adl adapter. A restriction enzyme (e.g., AcuI) can be applied, and the DNA can be cleaved 13 bp to the left of the Adl to form a linear DNA fragment. A third round of right and left adaptor (Ad3) can be ligated to the right and left flank of the linear DNA, and the resulting fragment can be PCR amplified. The adaptors can be modified so that they can bind to each other and form circular DNA. A type Ill restriction enzyme (e.g., EcoP15) can be added; EcoP15 can cleave the DNA 26 bp to the left of Ad3 and 26 bp to the right of Ad2. This cleavage can remove a large segment of DNA and linearize the DNA once again. A fourth round of right and left adaptors (Ad4) can be ligated to the DNA, the DNA can be amplified (e.g., by PCR), and modified so that they bind each other and form the completed circular DNA template.

Rolling circle replication (e.g., using Phi 29 DNA polymerase) can be used to amplify small fragments of DNA. The four adaptor sequences can contain palindromic sequences that can hybridize and a single strand can fold onto itself to form a DNA nanoball (DNB™) which can be approximately 200-300 nanometers in diameter on average. A DNA nanoball can be attached (e.g., by adsorption) to a microarray (sequencing flow cell). The flow cell can be a silicon wafer coated with silicon dioxide, titanium and hexamehtyldisilazane (HMDS) and a photoresist material. Sequencing can be performed by unchained sequencing by ligating fluorescent probes to the DNA. The color of the fluorescence of an interrogated position can be visualized by a high resolution camera. The identity of nucleotide sequences between adaptor sequences can be determined.

In some embodiments, high-throughput sequencing can take place using AnyDot.chips (Genovoxx, Germany). In particular, the AnyDot.chips allow for 10×-50× enhancement of nucleotide fluorescence signal detection. AnyDot.chips and methods for using them are described in part in International Publication Application Nos. WO 02088382, WO 03020968, WO 03031947, WO 2005044836, PCT/EP 05/05657, PCT/EP 05/05655; and German Patent Application Nos. DE 101 49 786, DE 102 14 395, DE 103 56 837, DE 10 2004 009 704, DE 10 2004 025 696, DE 10 2004 025 746, DE 10 2004 025 694, DE 10 2004 025 695, DE 10 2004 025 744, DE 10 2004 025 745, and DE 10 2005 012 301.

Other high-throughput sequencing systems include those disclosed in Venter, J., et al. Science 16 Feb. 2001; Adams, M. et al. Science 24 Mar. 2000; and M. J. Levene, et al. Science 299:682-686, January 2003; as well as US Publication No. 20030044781 and 2006/0078937. Overall such systems involve sequencing a target nucleic acid molecule having a plurality of bases by the temporal addition of bases via a polymerization reaction that is measured on a molecule of nucleic acid, such as the activity of a nucleic acid polymerizing enzyme on the template nucleic acid molecule to be sequenced is followed in real time. Sequence can then be deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable to move along the target nucleic acid molecule and extend the oligonucleotide primer at an active site. A plurality of labeled types of nucleotide analogs are provided proximate to the active site, with each distinguishable type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The steps of providing labeled nucleotide analogs, polymerizing the growing nucleic acid strand, and identifying the added nucleotide analog are repeated so that the nucleic acid strand is further extended and the sequence of the target nucleic acid is determined.

Prior to sequencing, nucleic acid molecules can be barcoded or otherwise labeled. Barcoding can allow for easier grouping of sequence reads. For example, barcodes can be used to identify sequences originating from the same nucleic acid molecule or DNA protein complex. Barcodes can also be used to uniquely identify individual junctions. For example, each junction can be marked with a unique (e.g., randomly generated) barcode which can uniquely identify the junction. Multiple barcodes can be used together, such as a first barcode to identify sequences originating from the same nucleic acid molecule or DNA protein complex and a second barcode that uniquely identifies individual junctions.

Barcoding can be achieved through a number of techniques. In some cases, barcodes can be included as a sequence within a punctuation oligonucleotide. In other cases, a nucleic acid molecule can be contacted to oligonucleotides comprising at least two segments: one segment contains a barcode and a second segment contains a sequence complementary to a punctuation sequence. After annealing to the punctuation sequences, the barcoded oligonucleotides can be extended with polymerase to yield barcoded molecules from the same punctuated nucleic acid molecule. Since the punctuated nucleic acid molecule is a rearranged version of the input nucleic acid molecule, in which phase information is preserved, the generated barcoded molecules are also from the same input nucleic acid molecule. These barcoded molecules comprise a barcode sequence, the punctuation complementary sequence, and genomic sequence.

For nucleic acid molecules (e.g., nucleic acids part of or recovered from a DNA protein complex) with or without punctuation, molecules can be barcoded by other means. For example, nucleic acid molecules can be contacted with barcoded oligonucleotides which can be extended to incorporate sequence from the nucleic acid molecule. Barcodes can hybridize to punctuation sequences, to restriction enzyme recognition sites, to sites of interest (e.g., genomic regions of interest), or to random sites (e.g., through a random n-mer sequence on the barcode oligonucleotide). Nucleic acid molecules can be contacted to the barcodes using appropriate concentrations and/or separations (e.g., spatial or temporal separation) from other nucleic acid molecules in the sample such that multiple nucleic acid molecules are not given then same barcode sequence. For example, a solution comprising nucleic acid molecules can be diluted to such a concentration that only one nucleic acid molecule or only one DNA protein complex will be contacted to a barcode or group of barcodes with a given barcode sequence. Barcodes can be contacted to nucleic acid molecules in free solution, in fluidic partitions (e.g., droplets or wells), or on an array (e.g., at particular array spots).

Barcoded nucleic acid molecules (e.g., extension products) can be sequenced, for example, on a short-read sequencing machine and sequence information is determined by grouping sequence reads having the same barcode into a common alignment, scaffold, phase, or other group. In this way, synthetic long reads can be achieved via short-read sequencing. Alternatively, prior to sequencing, the barcoded products can be linked together, for example though bulk ligation, to generate long molecules which are sequenced, for example, using long-read sequencing technology. In these cases, the embedded read pairs can be identifiable via the amplification adapters and punctuation sequences. Further information is obtained from the barcode sequence of the read pair.

Alternately, in some cases library molecules generated as described herein are concatenated without punctuation oligo insertion. These molecules are nonetheless suitable for sequencing using long read chemistries commercially available for generating reads of as long as 5 kb, 10 kb, 20 kb or longer. In these cases, concatenation junctions are readily identified through sequence analysis.

Long reads (e.g., synthetic or actual long reads) can be used to obtain information, such as phasing information, that may be otherwise difficult or impossible to determine from short reads. Phasing information includes maternal/paternal phasing as well as tumor/non-tumor phasing information. Tumor/non-tumor phasing can be used to differentiate cancer genomic information from somatic genomic information.

In an example, fragments from a library, such as a library created from an FFPE sample, as described above, are end sequenced. Read pairs are observed which indicate that the contigs where each end mapped are physically linked on a common nucleic acid molecule in the sample. The resulting library is further analyzed by sequencing in order to determine the distance between paired ends of the recovered fragments by comparing the location of the isolated sequences to a genome assembly. The long distance read pair frequencies in the FFPE samples are compared to the long distance read pair frequencies of a non-FFPE sample. In an exemplary library, such as the above library, sequencing reveals that the FFPE-Chicago method results in long distance read pair frequencies comparable to (>200 kbp insert) or greater than (100 kbp-200 kbp inserts) Chicago methods performed on non-FFPE samples. The complexity and raw sequencing coverage of the FFPE-Chicago library are also determined. Complexity of a library refers to the variety of different molecules within the library.

Genetic Information

Figure 2A:
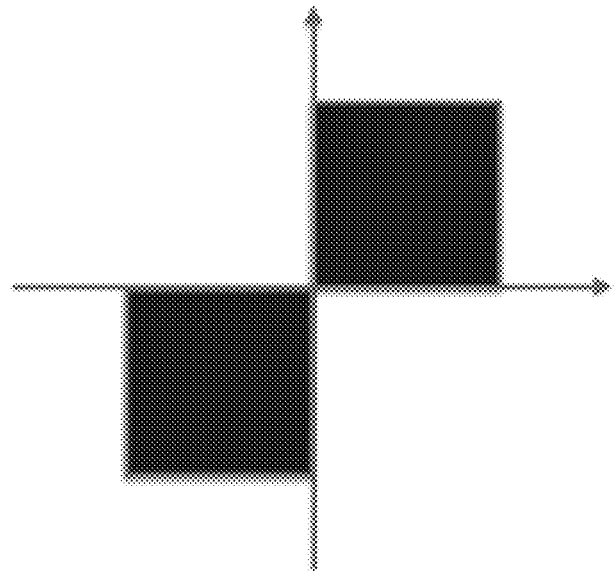
FIG. 2A and FIG. 2B depict exemplary simple kernels that can be used for finding reciprocal translocations.
Figure 2B:
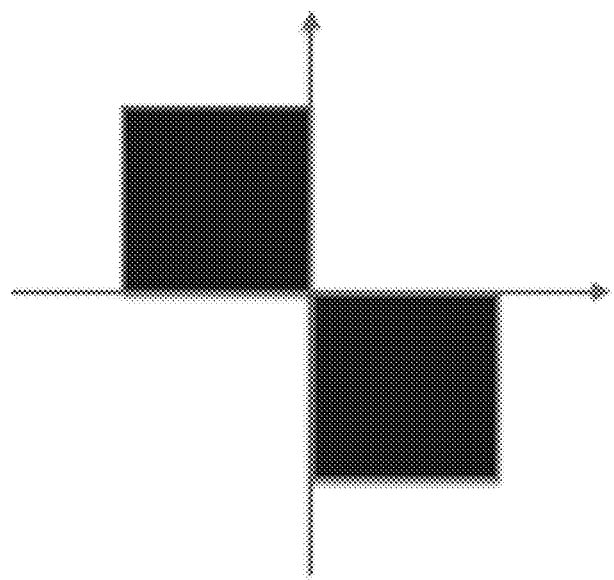
Figure 3:
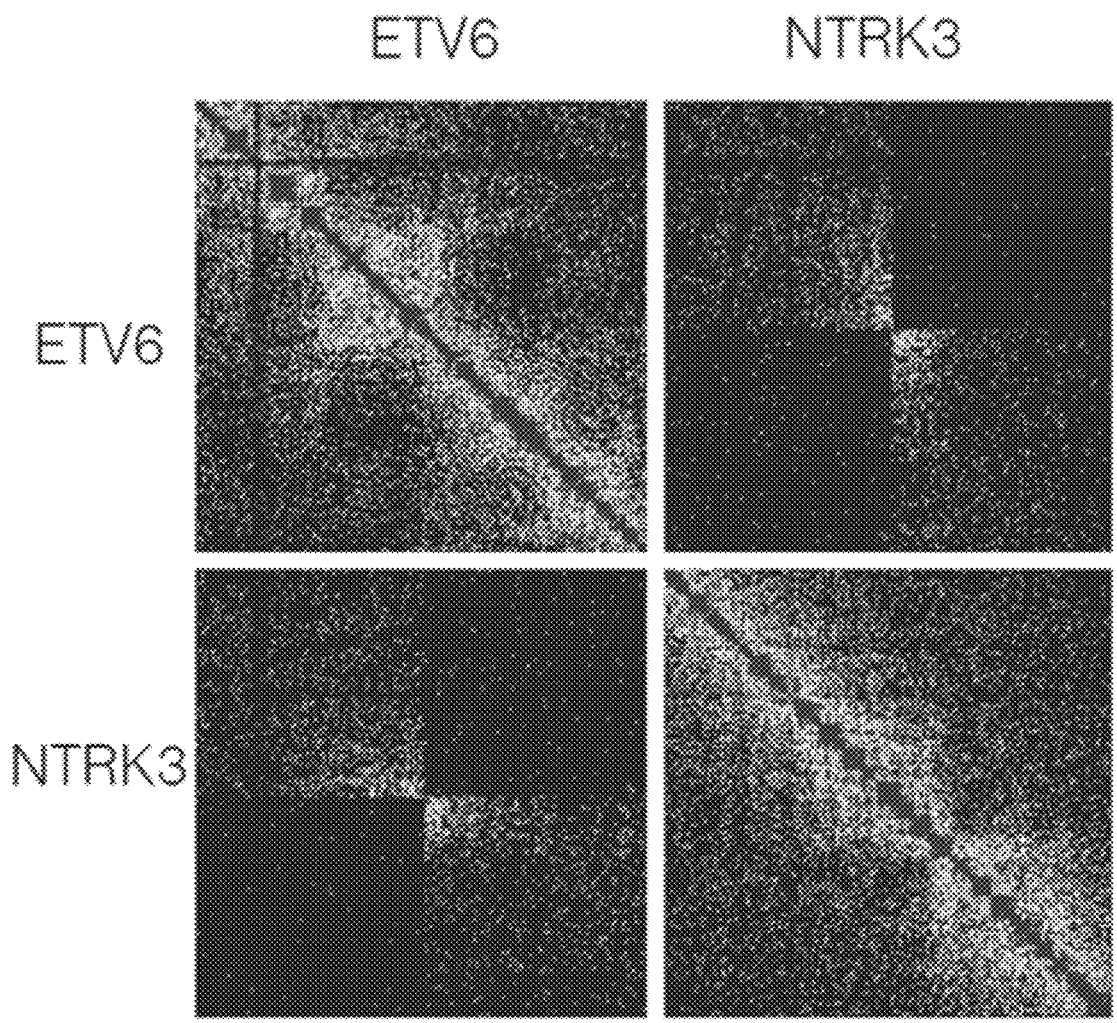
FIG. 3 depicts an image with a signal of a reciprocal translocation between ETV6 and NTRK3.

Phasing information, chromosome conformation, sequence assembly, and genetic features including but not limited to structural variations (SVs), copy number variants (CNVs), loss of heterozygosity (LOH), single nucleotide variants (SNVs), single nucleotide polymorphisms (SNPs), chromosomal translocations, gene fusions, and insertions and deletions (INDELs) can be determined by analysis of sequence read data produced by methods disclosed herein. Other inputs for analysis of genetic features can include a reference genome (e.g., with annotations), genome masking information, and a list of candidate genes, gene pairs, and/or coordinates of interest. Configuration parameters and genome masking information can be customized, or default parameters and genome masking can be used. In an example, read pairs are mapped to a genome, then each pair is represented as a point in the plane with x and y coordinates equal to the mapped position on concatenated reference chromosomes of read 1 and read 2 of the read pair, respectively. The x-y plane can be divided into non-overlapping square bins and the number of read pairs mapping to each bin can be tabulated. The bin counts can be visualized as an image (e.g., a heat map) with bins made to correspond to pixels. A variety of analysis techniques, such as image processing techniques, can be used to identify the signatures of genetic features such as different rearrangements. For example, kernel convolution filtering can be used to find points in the image corresponding to pairs of genomic loci that are fused. FIG. 2A and FIG. 2B show exemplary simple kernels that can be used for finding reciprocal translocations, such as those shown in FIG. 3. FIG. 3 shows an image with a signal of a reciprocal translocation between ETV6 and NTRK3. The "bowtie" shaped feature in the upper right and lower left quadrants is indicative of interaction between these two regions of the genome characteristic of a reciprocal translocation.

Inputs, such as sequence read data, can be formatted in appropriate file formats. For example, sequence read data can be contained in FASTA files, FASTQ files, BAM files, SAM files, or other file formats. Input sequence read data can be unaligned. Input sequence read data can be aligned.

Sequence read data can be prepared for analysis. For example, reads can be trimmed for quality. Reads can also be trimmed to remove sequencing adapters, if necessary.

Sequence read data can be aligned. For example, read pairs can be aligned to a specified reference genome. In some cases, the reference genome is CRCh38. Alignment can be performed with a variety of algorithms or tools, including but not limited to SNAP, Burrows-Wheeler aligners (e.g., bwa-sw, bwa-mem, bwa-aln), Bowtie2, Novoalign, and modifications or variations thereof.

Quality control (QC) reports of the analysis can also be generated. QC reports can be used to identify failed libraries before conducting deeper sequencing. Such quality control reports can include a variety of metrics. QC metrics can include but are not limited to total read pairs, percent of duplicates (e.g., PCR duplicates), percent of unmapped reads, percent of reads with low map quality (e.g., Q<20), percent of read pairs mapped to different chromosomes, percent of read pair inserts (such as distance between mapping positions) between 0 and 1 kbp, percent of read pair inserts between 1 kbp and 100 kbp, percent of read pair inserts between 100 kbp and 1 Mbp, percent of read pair inserts above 1 Mbp, percent of read pairs containing a ligation junction, proximity to restriction fragment ends, a read pair separation plot, and an estimate of library complexity. QC metrics can be used to optimize the analysis, and to identify quality problems in reagents, samples, and users. Sequence alignments can be filtered based on one or more of the QC metrics. Duplicate reads can also be filtered, for example based on comparison of reads at closely corresponding positions.

Sequence read analysis results can include link density results. Link density results can include whole genome, one locus, and two locus views of link density results. Link density results can be output as a data set. Link density results can be presented as a linkage density plot (LDP), such as a heat map of interactions (e.g., contacts) between regions of a chromosome or a genome. Link density results can be associated with a score, such as a quality score. In some cases, link density visualizations are output for results that exceed a score threshold. In an example, visualizations are included for the whole genome, for de novo calls that exceed a score threshold, for single-sided candidate calls that exceed a score threshold and for all double-sided candidates, including those classified as negative. Link density visualization can include a scale (e.g., a color scale), a length scale bar, gene name labels, exon/intron structure glyphs for genes, and highlighting of detected rearrangements.

Figure 4A:
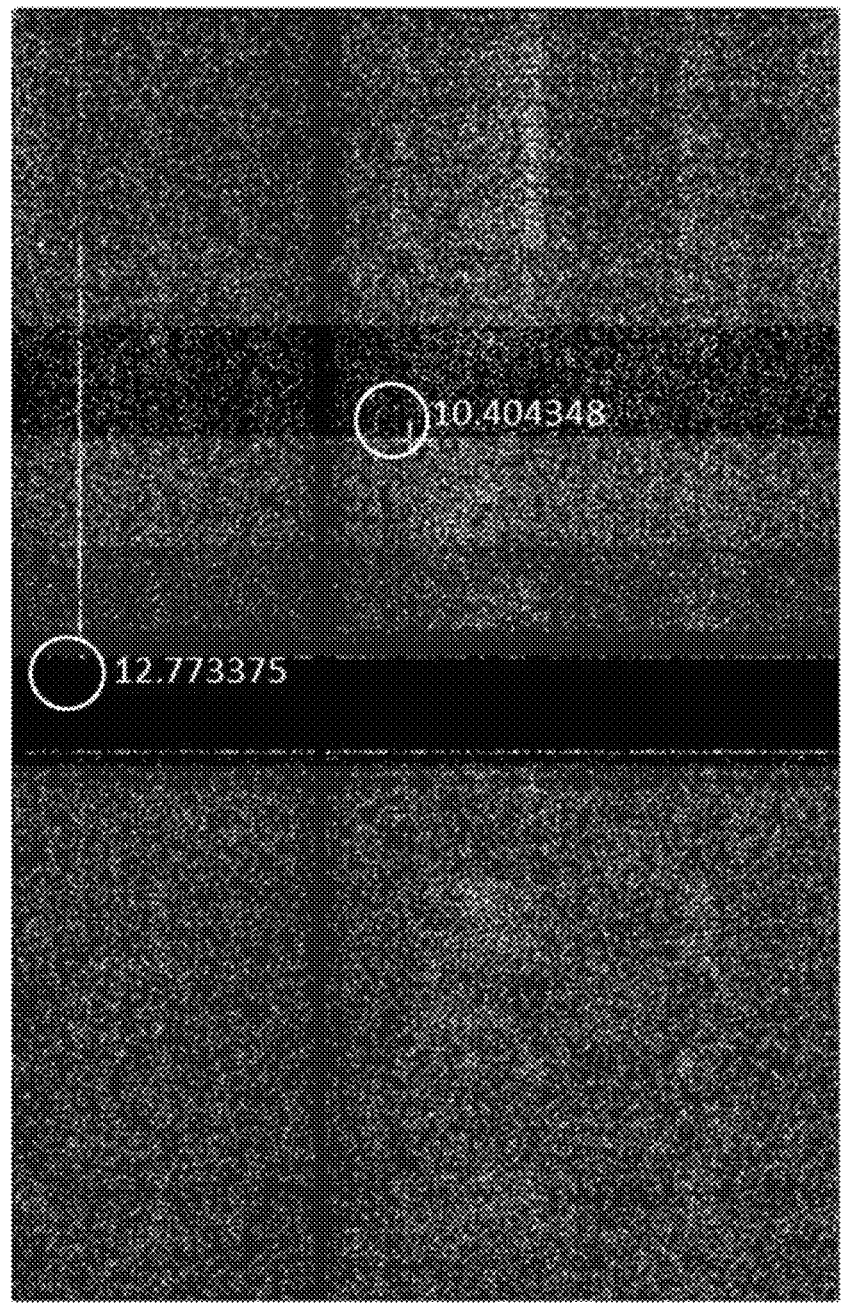
Figure 4B:
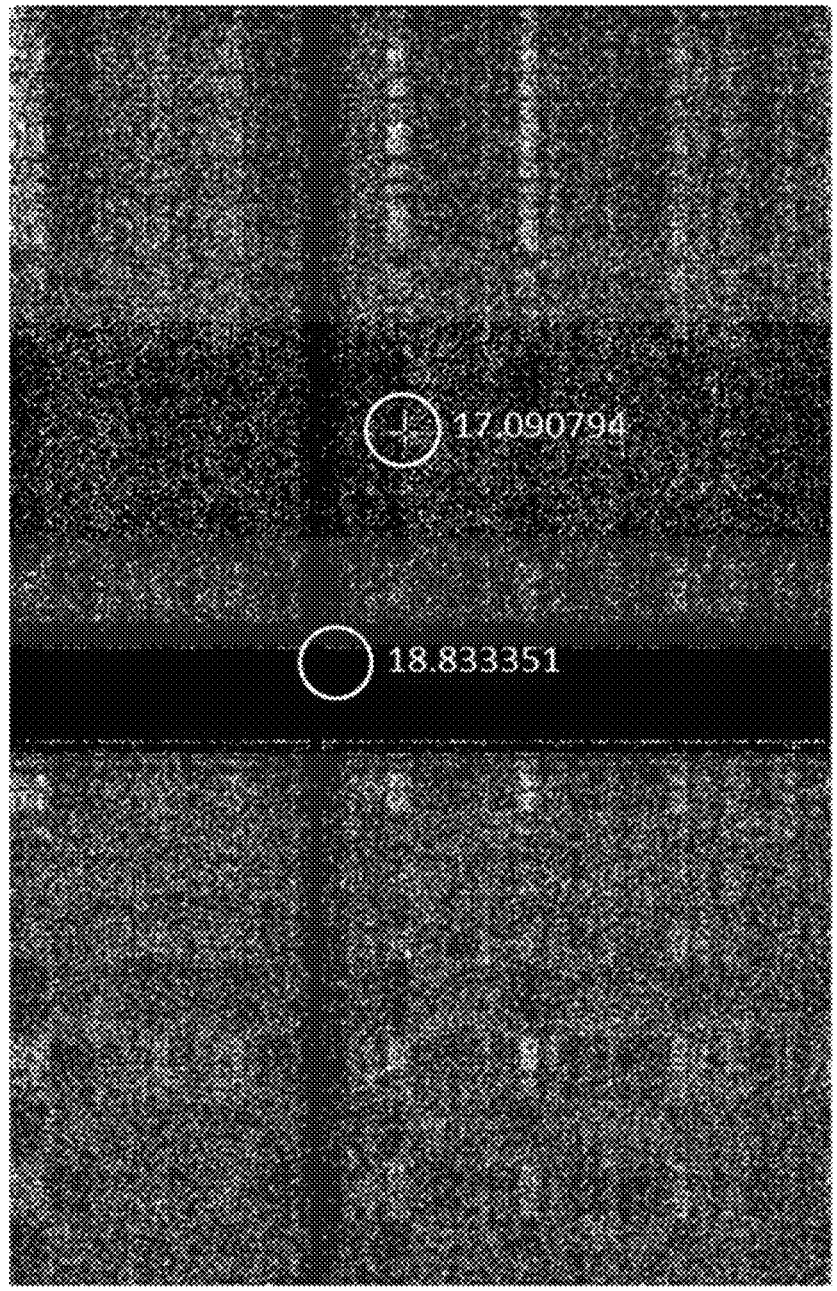
Figure 4C:
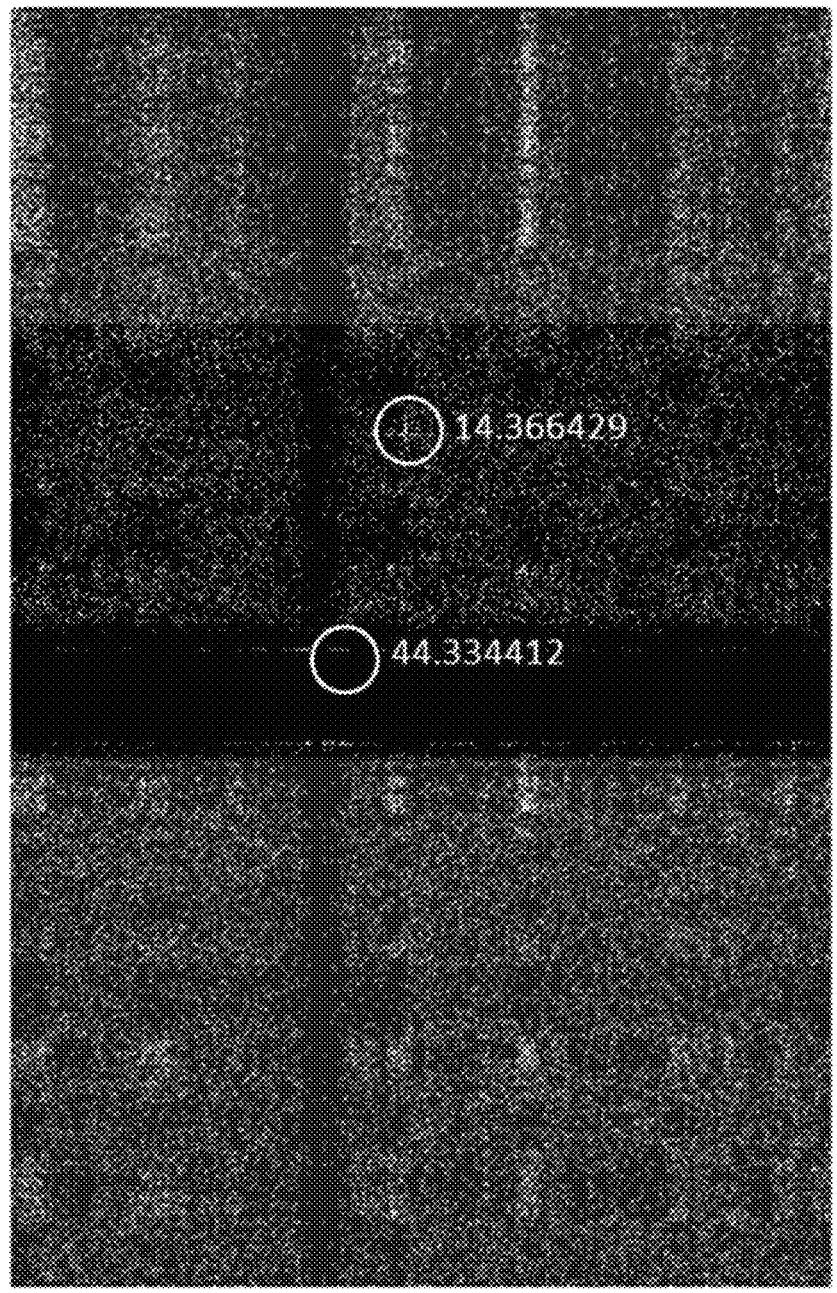
Figure 5A:
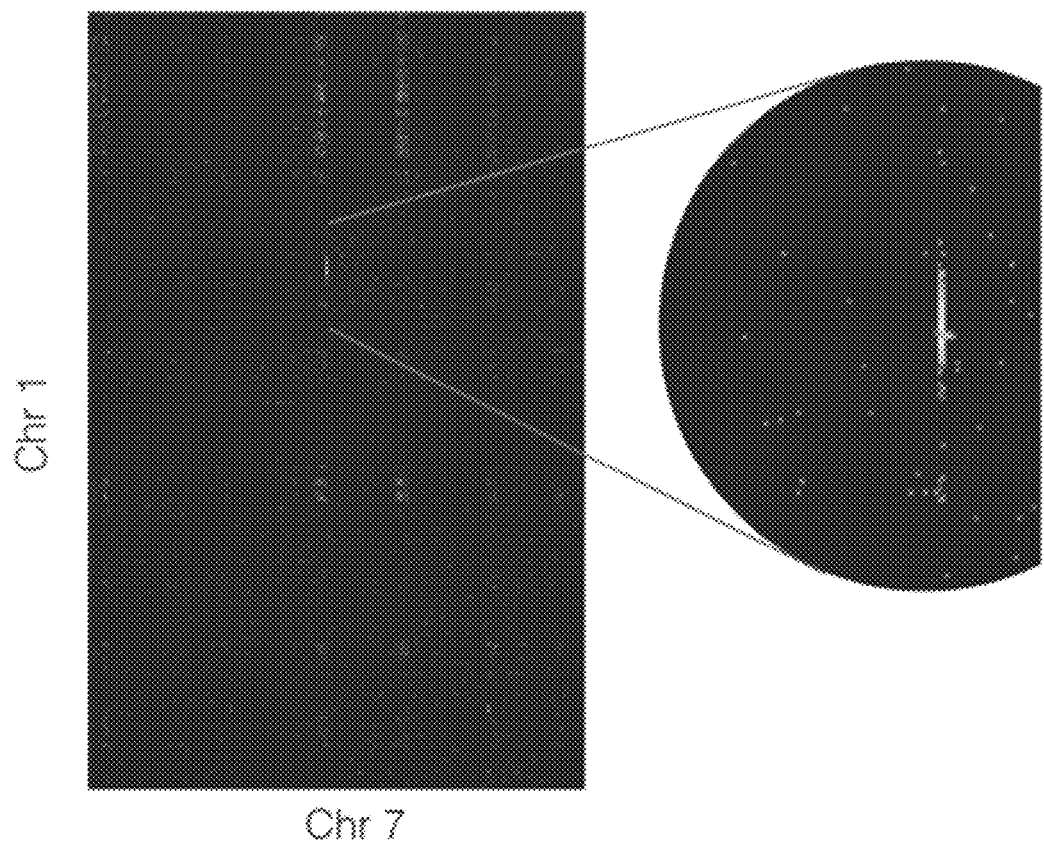
FIG. 5A, FIG. 5B, and FIG. 5C depict median normalized read density (over 10 samples) for chromosome 1 versus chromosome 7 (FIG. 5A), chromosome 2 versus chromosome 5 (FIG. 53), and chromosome 1 versus chromosome 1 (FIG. 5C).
Figure 5B:
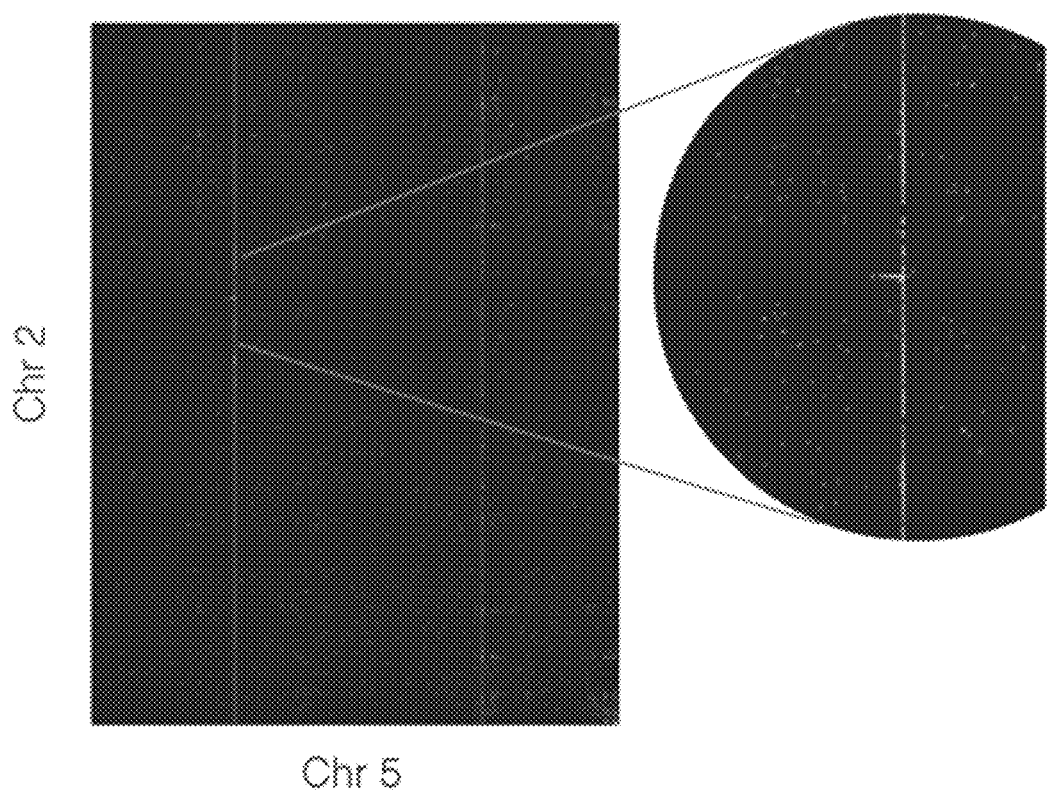
Figure 5C:
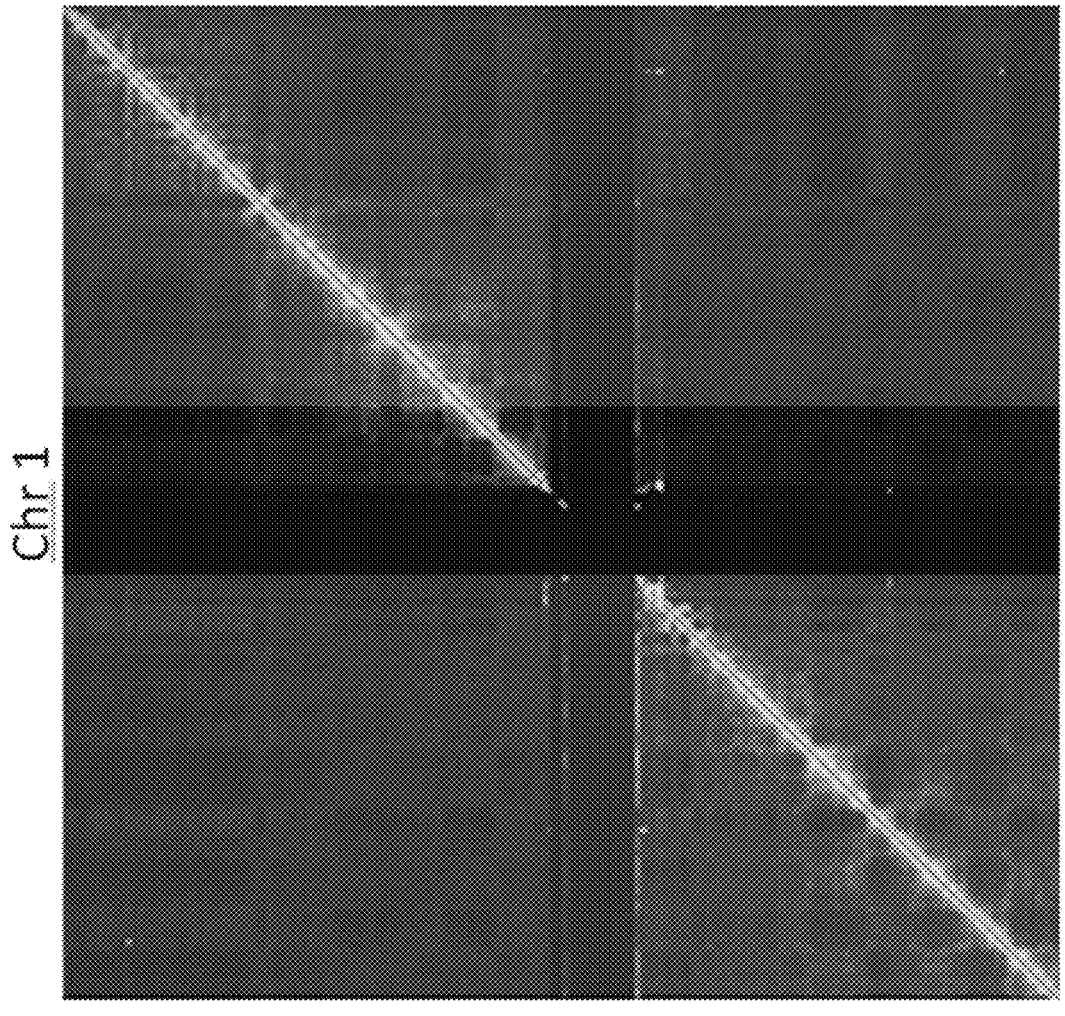
Figure 6A:
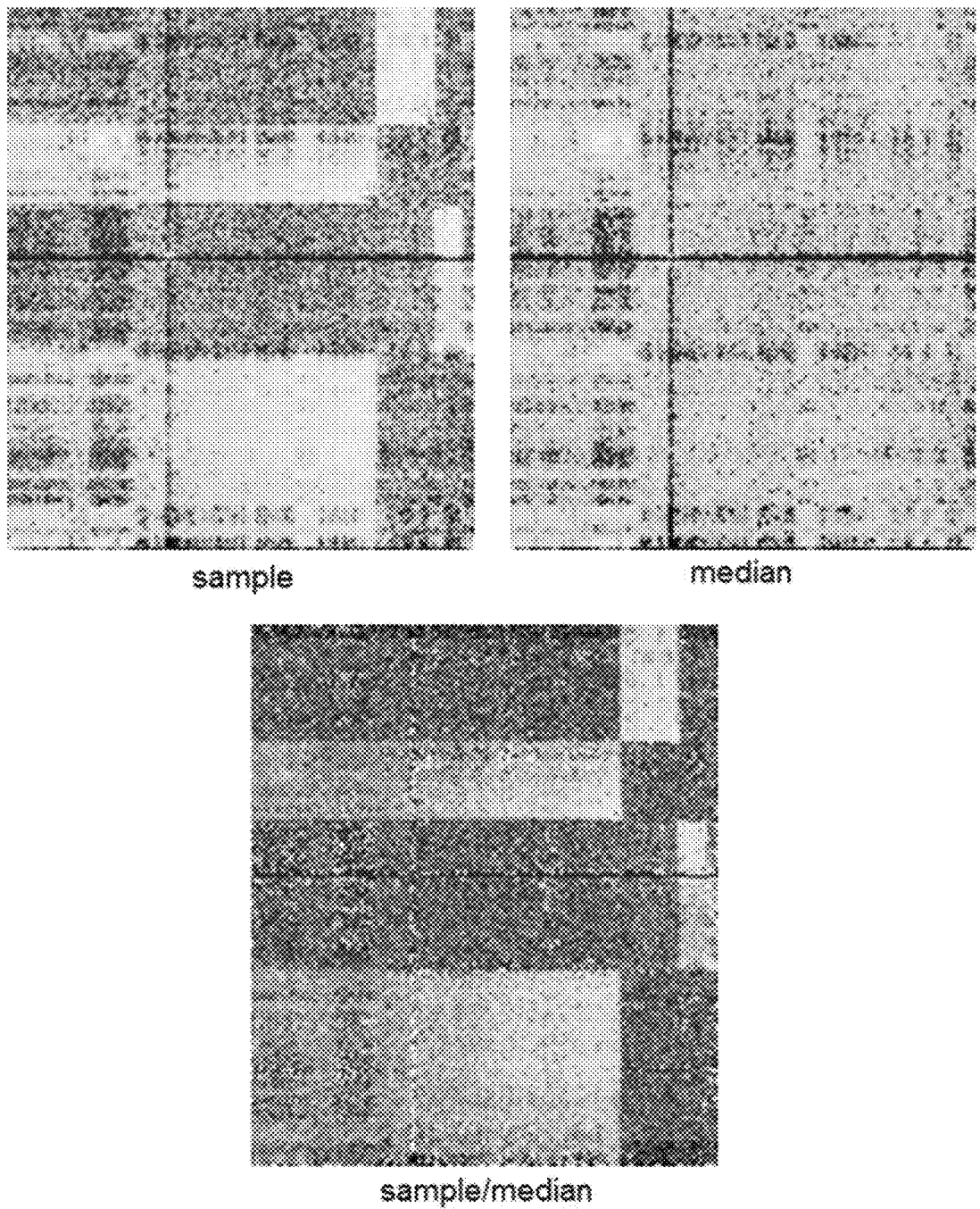
FIG. 6A and FIG. 6B depict various bin handling approaches.
Figure 6B:
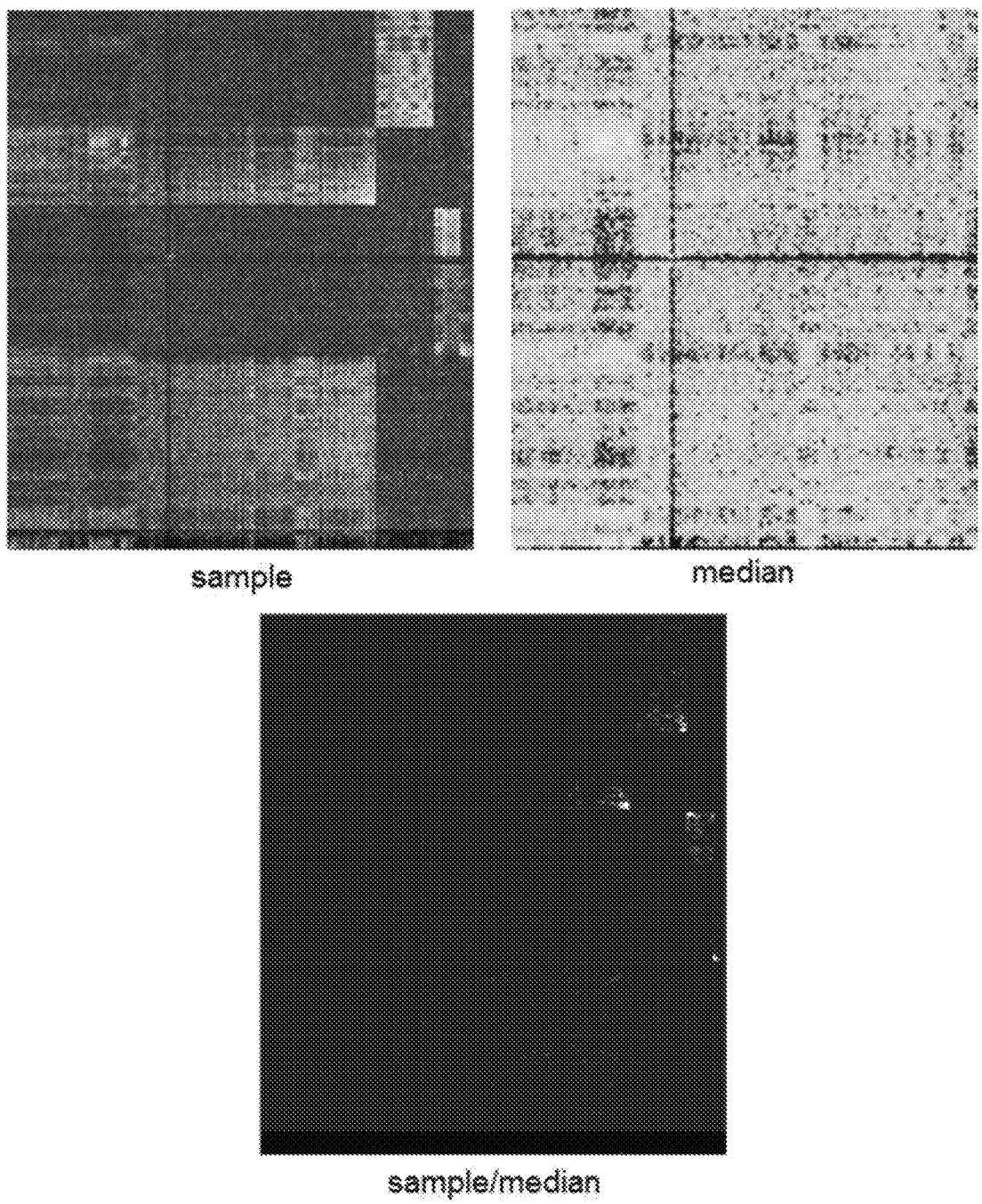

Linkage information can be normalized to control for effects and biases such as coverage, fragment mappability, fragment GC content, and fragment length. Normalization can be conducted by matrix balancing or other factor-agnostic methods. Matrix balancing can employ algorithms such as the Sinkhorn-Knopp algorithm or Knight-Ruiz normalization. Normalization can also be conducted to correct for background signal that may lead to false positives. For example, FIG. 4A, FIG. 4B, and FIG. 4C show image analysis-based results at the same pair of chromosomes compared in three different samples. Several "hits" (circled in the figures) are found in the same position across multiple samples, raising the suspicion that these are false positives. Normalization, such as by the median normalized read density across a pool of samples (e.g., 10 samples), can be used to correct individual sample data, for example by dividing the sample pixels by the median pixels. FIG. 5A, FIG. 5B, and FIG. 5C show median normalized read density (over 10 samples) for chromosome 1 versus chromosome 7 (FIG. 5A), chromosome 2 versus chromosome 5 (FIG. 5B), and chromosome 1 versus chromosome 1 (FIG. 5C). Normalization can be conducted with various bin handling approaches, including equal bin sizes, as shown in FIG. 6A, and with bin interpolation, as shown in FIG. 6B. In some cases, bin interpolation can yield reduced background noise compared to equal bin sizes, and result in more sharply resolved features.

Aligned sequence data can be analyzed for rearrangements, including rearrangements through the whole genome and rearrangements at specific two-locus (or two-sided) candidate genes. Analysis can also include identification of contacts, fusions, and joins. Alignments of sequence read data (e.g., in a BAM file or other suitable format) can be input into the analysis. Genome masking information can be input as well, or default genome masking information can be used in the analysis. Analysis can be conducted across the entire genome. Additionally or alternatively, analysis can be conducted for a list of two-sided candidate fusions. In some cases, the analysis conducted on a list of candidate fusions is more sensitive than the analysis conducted on a whole genome. Analysis of two-sided candidate fusions can detect fusions involving translocations of relatively short segments of DNA that may be missed by a genome-wide scan.

Analysis to identify features such as contacts and rearrangements (including but not limited to deletions, duplications, insertions, inversions or reversals, translocations, joins, fusions, and fissions), and other interactions can be conducted with a variety of techniques. Analysis techniques can include statistical and probability analysis, signal processing including Fourier analysis, computer vision and other image processing, language processing (e.g., natural language processing), and machine learning. For example, interaction plots such as contact matrixes can be analyzed for features indicative of features. In some cases, filters can be applied to plots or other data. Filters can be convolution filters including but not limited to smoothing filters (e.g., kernel smoothing or Savitzky-Golay filter, Gaussian blur).

Some embodiments involve machine learning as a component of genome structure determination, and accordingly some computer systems are configured to comprise a module having a machine learning capacity. Machine learning modules comprise at least one of the following listed modalities, so as to constitute a machine learning functionality.

Modalities that constitute machine learning variously demonstrate a data filtering capacity, so as to be able to perform automated mass spectrometric data spot detection and calling. This modality is in some cases facilitated by the presence of predicted patterns indicative of various genomic structural changes, such as inversions, insertions, deletions, or translocations.

Modalities that constitute machine learning variously demonstrate a data treatment or data processing capacity, so as to render read pair frequencies in a form conducive to downstream analysis. Examples of data treatment include but are not necessarily limited to log transformation, assigning of scaling ratios, or mapping data to crafted features so as to render the data in a form that is conducive to downstream analysis.

Machine learning data analysis components as disclosed herein regularly process a wide range of features in a read pair data set, such as 1 to 10,000 features, or 2 to 300,000 features, or a number of features within either of these ranges or higher than either of these ranges. In some cases, data analysis involves at least 1 k, 2 k, 3 k, 4 k, 5 k, 6 k, 7 k, 8 k, 9 k, 10 k, 20 k, 30 k, 40 k, 50 k, 60 k, 70 k, 80 k, 90 k, 100 k, 120 k, 140 k, 160 k, 180 k, 200 k, 220 k, 2240 k, 260 k, 280 k, 300 k, or more than 300 k features.

Read pair distribution patterns are identified using any number of approaches consistent with the disclosure herein. In some cases, read pair distribution patterns selection comprises elastic net, information gain, random forest imputing or other feature selection approaches consistent with the disclosure herein and familiar to one of skill in the art.

Selected read pair distribution patterns are matched against predicted patterns indicative of a genomic structural change, again using any number of approaches consistent with the disclosure herein. In some cases, read pair pattern detection comprises logistic regression, SVM, random forest, KNN, or other classifier approaches consistent with the disclosure herein and familiar to one of skill in the art.

Applying machine learning, or providing a machine learning module on a computer configured for the analyses disclosed herein, allows for the detection of relevant genomic structural changes for asymptomatic disease detection or early detection as part of an ongoing monitoring procedure, so as to identify a disease or disorder either ahead of symptom development or while intervention is either more easily accomplished or more likely to bring about a successful outcome.

Applying machine learning, or providing a machine learning module on a computer configured for the analyses disclosed herein also allows identification of structural rearrangements in individuals subjected to a drug treatment, for example as part of a drug trial, so that outcome of the trial for the individual or for the population may be concurrently or retrospectively correlated so as to identify particular genomic structural events that correspond positively or negatively with drug efficacy.

Applying machine learning, or providing a machine learning module on a computer configured for the analyses disclosed herein also allows identification of structural rearrangements that correspond with particular regions of genetically heterogeneous samples, such as tumor tissue samples collected without homogenization so as to preserve positional information in the sample. As some tumor regions are known to correspond to cell populations particularly adept at metastasis or tumor spread, identifying genomic rearrangements or other phase information that correlates with such cell populations assists in selecting a treatment regimen to target these particularly dangerous cell populations.

Monitoring is often but not necessarily performed in combination with or in support of a genetic assessment indicating a genetic predisposition for a disorder for which a signature of onset or progression is monitored. Similarly, in some cases machine learning is used to facilitate monitoring of or assessment of treatment efficacy for a treatment regimen, such that the treatment regimen can be modified over time, continued or resolved as indicated by the ongoing proteomics mediated monitoring.

Machine learning approaches and computer systems having modules configured to execute machine learning algorithms facilitate identification of phase information or genomic rearrangement in datasets of varying complexity. In some cases the phase information or genomic rearrangements are identified from an untargeted database comprising a large amount of mass spectrometric data, such as data obtained from a single individual at multiple time points, samples taken from multiple individuals such as multiple individuals of a known status for a condition of interest or known eventual treatment outcome or response, or from multiple time points and multiple individuals.

Alternately, in some cases machine learning facilitates the refinement of a genomic rearrangement or phase information through the analysis of a database targeted to that a genomic rearrangement or phase information, by for example collecting a genomic rearrangement or phase information from a single individual over multiple time points, when a health condition for the individual is known for the time points, or collecting sequence information from multiple individuals of known status for a condition of interest, or collecting sequence information from multiple individuals at multiple time points. As is readily apparent, in some cases collection of sequence information is facilitated through the use of preserved sample such as crosslinked samples collected pursuant to surgery or FFPE samples collected pursuant to a drug trial.

Thus, sequence information is collected either alone or in combination with drug trial outcome or surgical intervention outcome information. Sequence data is subjected to machine learning, for example on a computer system configured as disclosed herein, so as to identify a subset of read pairs indicative of a pattern corresponding to a genomic rearrangement that either alone or in combination with one or more additional markers, account for a health status signal. Thus, machine learning in some cases facilitates identification of sequence, either DNA or RNA sequence, or of a genomic rearrangement that is individually informative of a health status in an individual.

The minimum distance between breakpoints for detectable rearrangements can be less than, about, or a number in a range defined by two numbers selected from the list of nucleic acid lengths comprising 2 bp, 3 bp, 4 bp, 5 bp, 6 bp, 7 bp, 8 bp, 9 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 kb, 2 kb, 3 kb, 4 kb, 5 kb, 6 kb, 7 kb, 8 kb, 9 kb, 10 kb, 20 kb, 30 kb, 40 kb, 50 kb, 60 kb, 70 kb, 80 kb, 90 kb, 100 kb, 200 kb, 300 kb, 400 kb, 500 kb, 600 kb, 700 kb, 800 kb, 900 kb, 1 Mb, 2 Mb, 3 Mb, 4 Mb, 5 Mb, 6 Mb, 7 Mb, 8 Mb, 9 Mb, 10 Mb, 20 Mb, 30 Mb, 40 Mb, 50 Mb, 60 Mb, 70 Mb, 80 Mb, 90 Mb, 100 Mb, 200 Mb, 300 Mb, 400 Mb, 500 Mb, 600 Mb, 700 Mb, 800 Mb, 900 Mb, or 1 Gb.

Rearrangement analysis can produce a list of pairs of breakpoints that are deemed joined in the subject genome. The list of pairs of breakpoint coordinates can also include statistical significance or confidence metrics (e.g., p-value) for the breakpoint coordinate pairs. These pairs of breakpoints can be output in an appropriate format, such as browser extensible data (BED) or BED-PE.

Analysis of chromosome conformation can also be conducted using the techniques disclosed herein. For example, topologically associating domains (TADs) and TAD boundaries can be determined. Other topological domains and boundaries can also be determined, including but not limited to lamina-associated domains (LADs), replication time zones, and large organized chromatin K9-modification (LOCK) domains.

Figure 7:
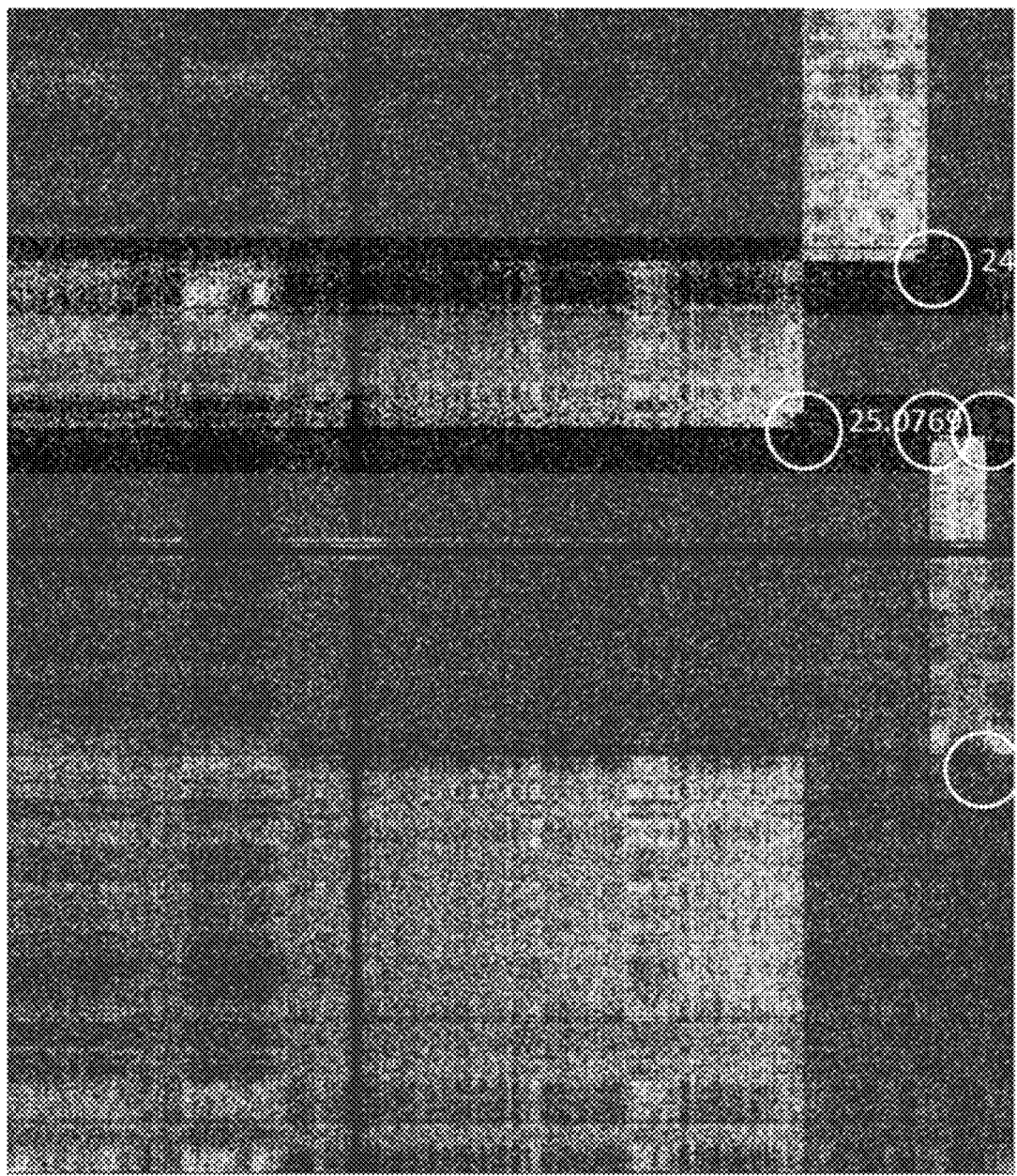
FIG. 7 depicts analysis by a genome-wide scanning analysis pipeline.

FIG. 7 shows analysis by a genome-wide scanning analysis pipeline. Sample calls made by the analytical pipeline are shown circled in white. FIG. 7 shows a plot of chromosome 3 versus chromosome 6, with 250 k bins.

In an exemplary embodiment, sequencing data is used to determine phasing information for polymorphisms known to be in the starting FFPE sample. For example, the sequencing data is used to determine whether certain polymorphisms such as SNPs were present on the same or different DNA molecules. Accuracy of the phasing determined using this method is measured by comparing to a known sequence, such as the sequence of the GIAB sample. For example, in some cases it is found that between 0-10,000, there were 132,796 SNPS found and 99.059% were in the correct phase. A high concordance (>95%) is seen up until about 1.5 MB (with the exception of the 70-80 kb bin, which missed 1 of 13 and the 1.1-1.3 MB bin which missed 2 of 15). In the 1.7-1.9 MB range, 7 of 7 SNP pair phases were properly called. From these data, it is concluded that, despite low levels of spurious linkage, proper long-range information is determined using the FFPE-Chicago method, even up to the megabase range. Importantly, these 'concordance' prediction rates are 95% or greater, significantly higher than the 50% success rate one would expect from random chance).

Structural Phasing Information

Currently, structural and phasing analyses (e.g., for medical purposes) remain challenging. For example, there is astounding heterogeneity among cancers, individuals with the same type of cancer, or even within the same tumor. Teasing out the causative from consequential effects can require very high precision and throughput at a low per-sample cost. In the domain of personalized medicine, one of the gold standards of genomic care is a sequenced genome with all variants thoroughly characterized and phased, including large and small structural rearrangements and novel mutations. To achieve this with previous technologies demands effort akin to that required for a de novo assembly, which is currently too expensive and laborious to be a routine medical procedure.

Phasing information includes maternal/paternal phasing as well as tumor/non-tumor phasing information. Tumor/non-tumor phasing can be used to differentiate cancer genomic information from somatic genomic information.

In some embodiments of the disclosure, a preserved tissue (e.g., an FFPE tissue) from a subject can be provided and the method can return an assembled genome, alignments with called variants (including large structural variants and copy number variants), phased variant calls, or any additional analyses. In other embodiments, the methods disclosed herein can provide long distance read pair libraries directly for the individual.

In various embodiments of the disclosure, the methods disclosed herein can generate long-range read pairs separated by large distances. The upper limit of this distance may be improved by the ability to collect DNA samples of large size. In some cases, the read pairs can span up to 50, 60, 70, 80, 90, 100, 125, 150, 175, 200, 225, 250, 300, 400, 500, 600, 700, 800, 900, 1000, 1500, 2000, 2500, 3000, 4000, 5000 kbp or more in genomic distance. In some examples, the read pairs can span up to 500 kbp in genomic distance. In other examples, the read pairs can span up to 2000 kbp in genomic distance. The methods disclosed herein can integrate and build upon standard techniques in molecular biology, and are further well-suited for increases in efficiency, specificity, and genomic coverage.

In other embodiments, the methods disclosed herein can be used with currently employed sequencing technology. For example, the methods can be used in combination with well-tested and/or widely deployed sequencing instruments. In further embodiments, the methods disclosed herein can be used with technologies and approaches derived from currently employed sequencing technology.

In various embodiments, the disclosure provides for one or more methods disclosed herein that comprise the step of probing the physical layout of chromosomes within preserved (e.g., FFPE) samples or cells. Examples of techniques to probe the physical layout of chromosomes through sequencing include the "C" family of techniques, such as chromosome conformation capture ("3C"), circularized chromosome conformation capture ("4C"), carbon-copy chromosome capture ("5C"), and Hi-C based methods; and ChIP based methods, such as ChIP-loop, ChIP-PET. These techniques utilize the fixation of chromatin in live cells to cement spatial relationships in the nucleus. Subsequent processing and sequencing of the products allows a researcher to recover a matrix of proximate associations among genomic regions. With further analysis these associations can be used to produce a three-dimensional geometric map of the chromosomes as they are physically arranged in the preserved (e.g., FFPE) sample. Such techniques describe the discrete spatial organization of chromosomes, and provide an accurate view of the functional interactions among chromosomal loci.

In some embodiments, the intrachromosomal interactions correlate with chromosomal connectivity. In some cases, the intrachromosomal data can aid genomic assembly. In some cases, the chromatin is reconstructed in vitro. This can be advantageous because chromatin—particularly histones, the major protein component of chromatin—is important for fixation under the most common "C" family of techniques for detecting chromatin conformation and structure through sequencing, 3C, 4C, 5C, and Hi-C. Chromatin is highly non-specific in terms of sequence and will generally assemble uniformly across the genome. In some cases, the genomes of species that do not use chromatin can be assembled on a reconstructed chromatin and thereby extend the horizon for the disclosure to all domains of life.

Figure 8A:
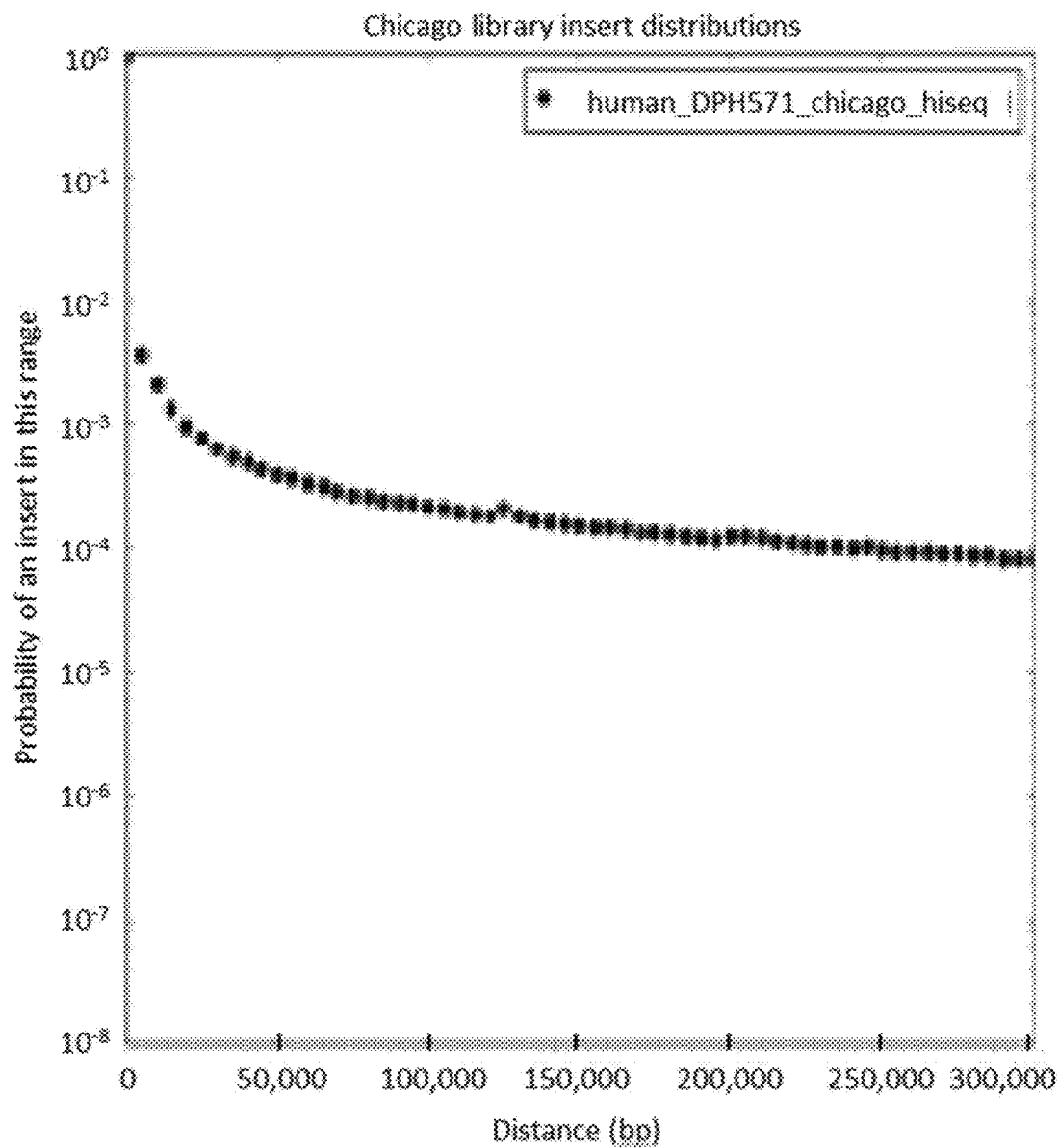
FIG. 8A and FIG. 8B depict read pair distance frequency data derived from FFPE-based 'Chicago' read pair libraries (FIG. 8A) and classic 'Chicago' based read pair libraries (FIG. 8B).
Figure 8B:
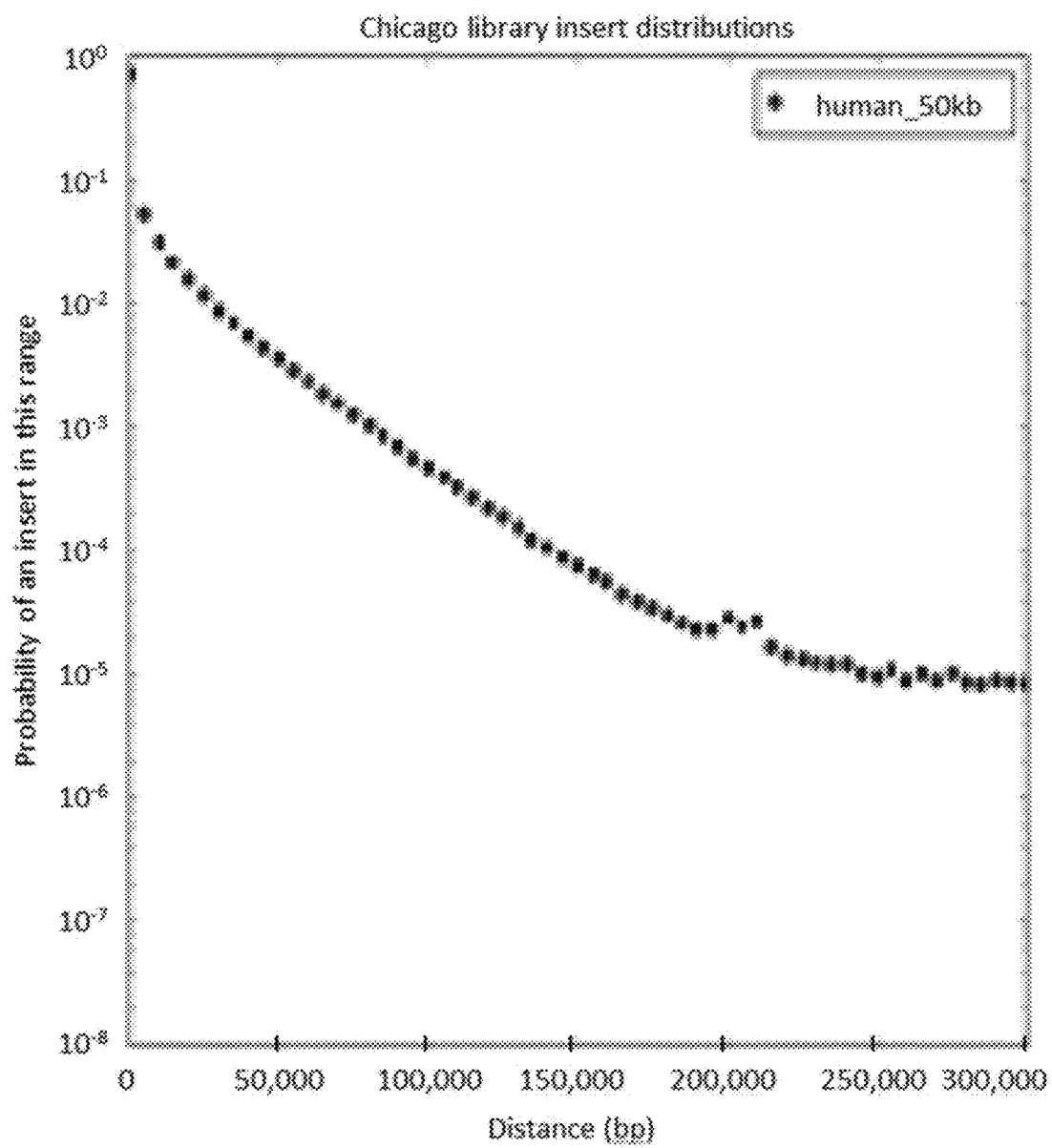

Read pair data can be obtained from a chromatin conformation capture technique. In some examples, ligation or other tagging is accomplished so as to mark genome regions that are in close physical proximity. Crosslinking of the complex such that proteins (such as histones) are stably bound in a complex with the DNA molecule, e.g. genomic DNA, within chromatin can be accomplished according to a suitable method described in further detail elsewhere herein or otherwise known in the art. In some cases, crosslinks arising from sample preservation (e.g., from fixation) are utilized by extracting DNA-protein complexes under conditions such that such complexes are not degraded, such as through the exclusion of proteinase K treatment. For example, nucleotide segments that are not in close proximity along a genome sequence can be in close physical proximity when part of a structure such as chromatin. Such nucleotide segments can be ligated together and subsequently analyzed according to methods of the present disclosure. For example, ligated nucleotide segments can be sequenced and the distance between the sequenced ends of two ligated segments (insert distance) can be analyzed. FIG. 8A shows a graph of the probability of an insert in a particular range as a function of insert distance in base pairs (bp) for a preserved sample (e.g., an FFPE sample) analyzed by techniques of the present disclosure. FIG. 8B shows a similar graph for a sample analyzed using a Chicago method. In both graphs, the x-axis shows the insert distance (bp), from 0 to 300,000, while the y-axis shows the probability of an insert of that distance, from 100 at the top of the axis to $10^{-8}$ at the bottom of the axis (logarithmic).

In some cases, two or more nucleotide sequences can be crosslinked via proteins bound to one or more nucleotide sequences. One approach is to expose the chromatin to ultraviolet irradiation (Gilmour el al., Proc. Nat'l. Acad. Sci. USA 81:4275-4279, 1984). Crosslinking of polynucleotide segments may also be performed utilizing other approaches, such as chemical or physical (e.g. optical) crosslinking. Suitable chemical crosslinking agents include, but are not limited to, formaldehyde and psoralen (Solomon el al., Proc. Natl. Acad. Sci. USA 82:6470-6474, 1985; Solomon et al., Cell 53:937-947, 1988). For example, crosslinking can be performed by adding 2% formaldehyde to a mixture comprising the DNA molecule and chromatin proteins. Other examples of agents that can be used to crosslink DNA include, but are not limited to, UV light, mitomycin C, nitrogen mustard, melphalan, 1,3-butadiene diepoxide, cis diaminedichloroplatinum(II) and cyclophosphamide. Suitably, the crosslinking agent will form crosslinks that bridge relatively short distances—such as about 2 Å—thereby selecting intimate interactions that can be reversed.

Universally, procedures for probing the physical layout of chromosomes, such as Hi-C based techniques, utilize chromatin that is formed within a cell/organism, such as chromatin isolated from cultured cells or primary tissue. Chicago based methods provide not only for the use of such techniques with chromatin isolated from a cell/organism but also with reconstituted chromatin. Reconstituted chromatin is differentiated from chromatin formed within a cell/organism over various features. First, for many samples, the collection of naked DNA samples can be achieved by using a variety of noninvasive to invasive methods, such as by collecting bodily fluids, swabbing buccal or rectal areas, taking epithelial samples, etc. Second, reconstituting chromatin substantially prevents the formation of inter-chromosomal and other long-range interactions that generate artifacts for genome assembly and haplotype phasing. In some cases, a sample may have less than about 20, 15, 12, 11, 10, 9, 8, 7, 6, 5, 4, 3, 2, 1, 0.5, 0.4, 0.3, 0.2, 0.1% or less inter-chromosomal or intermolecular crosslinking according to the methods and compositions of the disclosure. In some examples, the sample may have less than about 5% inter-chromosomal or intermolecular crosslinking. In some examples, the sample may have less than about 3% inter-chromosomal or intermolecular crosslinking. In further examples, may have less than about 1% inter-chromosomal or intermolecular crosslinking. Third, the frequency of sites that are capable of crosslinking and thus the frequency of intramolecular crosslinks within the polynucleotide can be adjusted. For example, the ratio of DNA to histones can be varied, such that the nucleosome density can be adjusted to a desired value. In some cases, the nucleosome density is reduced below the physiological level. Accordingly, the distribution of crosslinks can be altered to favor longer-range interactions. In some embodiments, sub-samples with varying crosslinking density may be prepared to cover both short- and long-range associations. For example, the crosslinking conditions can be adjusted such that at least about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 40%, about 45%, about 50%, about 60%, about 70%, about 80%, about 90%, about 95%, or about 100% of the crosslinks occur between DNA segments that are at least about 50 kb, about 60 kb, about 70 kb, about 80 kb, about 90 kb, about 100 kb, about 110 kb, about 120 kb, about 130 kb, about 140 kb, about 150 kb, about 160 kb, about 180 kb, about 200 kb, about 250 kb, about 300 kb, about 350 kb, about 400 kb, about 450 kb, or about 500 kb apart on the sample DNA molecule.

High degrees of accuracy required by cancer genome sequencing can be achieved using the methods and systems described herein. Inaccurate reference genomes can make base-calling challenging when sequencing cancer genomes. Heterogeneous samples and small starting materials, for example a sample obtained by biopsy introduce additional challenges. Further, detection of large scale structural variants and/or losses of heterozygosity is often crucial for cancer genome sequencing, as well as the ability to differentiate between somatic variants and errors in base-calling.

Systems and methods described herein may generate accurate long sequences from complex samples containing 2, 3, 4, 5, 6, 7, 8, 9, 10, 12, 15, 20 or more varying genomes. Mixed samples of normal, benign, and/or tumor origin may be analyzed, optionally without the need for a normal control. In some embodiments, starting samples as little as 100 ng or even as little as hundreds of genome equivalents are utilized to generate accurate long sequences. Systems and methods described herein may allow for detection of copy number variants, large scale structural variants and rearrangements, phased variant calls may be obtained over long sequences spanning about 1 kbp, about 2 kbp, about 5 kbp, about 10 kbp, 20 kbp, about 50 kbp, about 100 kbp, about 200 kbp, about 500 kbp, about 1 Mbp, about 2 Mbp, about 5 Mbp, about 10 Mbp, about 20 Mbp, about 50 Mbp, or about 100 Mbp or more nucleotides. For example, phase variant calls may be obtained over long sequences spanning about 1 Mbp or about 2 Mbp.

Samples can comprise tissue sections of various volumes and surface areas. In some cases, a sample comprises a tissue section between about 5 μm and 10 μm in thickness. In some cases, a sample comprises a tissue section about 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1000 μm, or more in thickness. In some cases, a sample comprises a tissue section at least about 1 μm, 2 μm, 3 μm, 4 μm, 5 μm, 6 μm, 8 μm, 9 μm, 10 μm, 11 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1000 μm, or more in thickness. In some cases, a sample comprises a tissue section at most about 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1000 μm, or more in thickness. In some cases, a sample comprises a tissue section with a surface area between about 100 and 300 $mm^2$. In some cases, a sample comprises a tissue section about 10 $mm^2$, 20 $mm^2$, 30 $mm^2$, 40 $mm^2$, 50 $mm^2$, 60 $mm^2$, 70 $mm^2$, 80 $mm^2$, 90 $mm^2$, 100 $mm^2$, 200 $mm^2$, 300 $mm^2$, 400 $mm^2$, 500 $mm^2$, 600 $mm^2$, 700 $mm^2$, 800 $mm^2$, 900 $mm^2$, 1000 $mm^2$, or more in surface area. In some cases, a sample comprises a tissue section at least about 10 $mm^2$, 20 $mm^2$, 30 $mm^2$, 40 $mm^2$. 50 $mm^2$, 60 $mm^2$, 70 $mm^2$, 80 $mm^2$, 90 $mm^2$, 100 $mm^2$, 200 $mm^2$, 300 $mm^2$, 400 $mm^2$, 500 $mm^2$, 600 $mm^2$, 700 $mm^2$, 800 $mm^2$, 900 $mm^2$, 1000 $mm^2$, or more in surface area. In some cases, a sample comprises a tissue section at most about 10 $mm^2$, 20 $mm^2$. 30 $mm^2$, 40 $mm^2$, 50 $mm^2$, 60 $mm^2$, 70 $mm^2$, 80 $mm^2$, 90 $mm^2$, 100 $mm^2$, 200 $mm^2$, 300 $mm^2$, 400 $mm^2$, 500 $mm^2$, 600 $mm^2$, 700 $mm^2$, 800 $mm^2$, 900 $mm^2$, 1000 $mm^2$, or more in surface area.

Haplotypes determined using the methods and systems described herein may be assigned to computational resources, for example computational resources over a network, such as a cloud system. Short variant calls can be corrected, if necessary, using relevant information that is stored in the computational resources. Structural variants can be detected based on the combined information from short variant calls and the information stored in the computational resources. Problematic parts of the genome, such as segmental duplications, regions prone to structural variation, the highly variable and medically relevant MHC region, centromeric and telomeric regions, and other heterochromatic regions including but limited to those with repeat regions, low sequence accuracy, high variant rates, ALU repeats, segmental duplications, or any other relevant problematic parts known in the art, can be reassembled for increased accuracy.

A sample type can be assigned to the sequence information either locally or in a networked computational resource, such as a cloud. In cases where the source of the information is known, for example when the source of the information is from a cancer or normal tissue, the source can be assigned to the sample as part of a sample type. Other sample type examples generally include, but are not limited to, tissue type, sample collection method, presence of infection, type of infection, processing method, size of the sample, etc. In cases where a complete or partial comparison genome sequence is available, such as a normal genome in comparison to a cancer genome, the differences between the sample data and the comparison genome sequence can be determined and optionally output.

Methods for Haplotype Phasing

Because the read pairs generated by the methods disclosed herein are generally derived from intra-chromosomal contacts, any read pairs that contain sites of heterozygosity will also carry information about their phasing. Using this information, reliable phasing over short, intermediate and even long (megabase) distances can be performed rapidly and accurately. Experiments designed to phase data from one of the 1000 genomes trios (a set of mother/father/offspring genomes) have reliably inferred phasing. Additionally, haplotype reconstruction using proximity-ligation similar to Selvaraj et al. (*Nature Biotechnology* 31:1111-1118 (2013)) can also be used with haplotype phasing methods disclosed herein.

For example, a haplotype reconstruction using proximity-ligation based method can also be used in the methods disclosed herein in phasing a genome. A haplotype reconstruction using proximity-ligation based method combines a proximity-ligation and DNA sequencing with a probabilistic algorithm for haplotype assembly. First, proximity-ligation sequencing is performed using a chromosome capture protocol, such as the Hi-C protocol. These methods can capture DNA fragments from two distant genomic loci that looped together in three-dimensional space. After shotgun DNA-sequencing of the resulting DNA library, paired-end sequencing reads have 'insert sizes' that range from several hundred base pairs to tens of millions of base pairs. Thus, short DNA fragments generated in a Hi-C experiment can yield small haplotype blocks, long fragments ultimately can link these small blocks together. With enough sequencing coverage, this approach has the potential to link variants in discontinuous blocks and assemble every such block into a single haplotype. This data is then combined with a probabilistic algorithm for haplotype assembly. The probabilistic algorithm utilizes a graph in which nodes correspond to heterozygous variants and edges correspond to overlapping sequence fragments that may link the variants. This graph might contain spurious edges resulting from sequencing errors or trans interactions. A max-cut algorithm is then used to predict parsimonious solutions that are maximally consistent with the haplotype information provided by the set of input sequencing reads. Because proximity ligation generates larger graphs than conventional genome sequencing or mate-pair sequencing, computing time and number of iterations are modified so that the haplotypes can be predicted with reasonable speed and high accuracy. The resulting data can then be used to guide local phasing using Beagle software and sequencing data from the genome project to generate chromosome-spanning haplotypes with high resolution and accuracy.

Determining Phase Information with Paired Ends

Further provided herein are methods and compositions for determining phase information from paired ends derived from FFPE-samples. Paired ends can be generated by any of the methods disclosed or those further illustrated in the provided Examples. For example, in the case of a DNA molecule bound to a solid surface which was subsequently cleaved, following re-ligation of free ends, re-ligated DNA segments are released from the solid-phase attached DNA molecule, for example, by restriction digestion. This release results in a plurality of paired end fragments. In some cases, the paired ends are ligated to amplification adapters, amplified, and sequenced with short read technology. In these cases, paired ends from multiple different solid phase-bound DNA molecules are within the sequenced sample. However, it is confidently concluded that for either side of a paired end junction, the junction adjacent sequence is derived from a common phase of a common molecule. In cases where paired ends are linked with a punctuation oligonucleotide, the paired end junction in the sequencing read is identified by the punctuation oligonucleotide sequence. In other cases, the pair ends were linked by modified nucleotides, which can be identified based on the sequence of the modified nucleotides used.

Alternatively, following release of paired ends, the free paired ends are ligated to amplification adapters and amplified. In these cases, the plurality of paired ends is then bulk ligated together to generate long molecules which are read using long-read sequencing technology. In other examples, released paired ends are bulk ligated to each other without the intervening amplification step. In either case, the embedded read pairs are identifiable via the native DNA sequence adjacent to the linking sequence, such as a punctuation sequence or modified nucleotides. The concatenated paired ends are read on a long-sequence device, and sequence information for multiple junctions is obtained. Since the paired ends derived from multiple different solid phase-bound DNA molecules, sequences spanning two individual paired ends, such as those flanking amplification adapter sequences, are found to map to multiple different DNA molecules. However, it is confidently concluded that for either side of a paired end junction, the junction-adjacent sequence is derived from a common phase of a common molecule. For example, in the case of paired ends derived from a punctuated molecule, sequences flanking the punctuation sequence are confidently assigned to a common DNA molecule. In preferred cases, because the individual paired ends are concatenated using the methods and compositions disclosed herein, one is able to sequence multiple paired ends in a single read.

Sequencing data generated using the methods and compositions described herein are used, in preferred embodiments, to generate phased de novo sequence assemblies, determine phase information, and/or identify structural variations.

Determining Structural Variations and Other Genetic Features

Figure 9A:
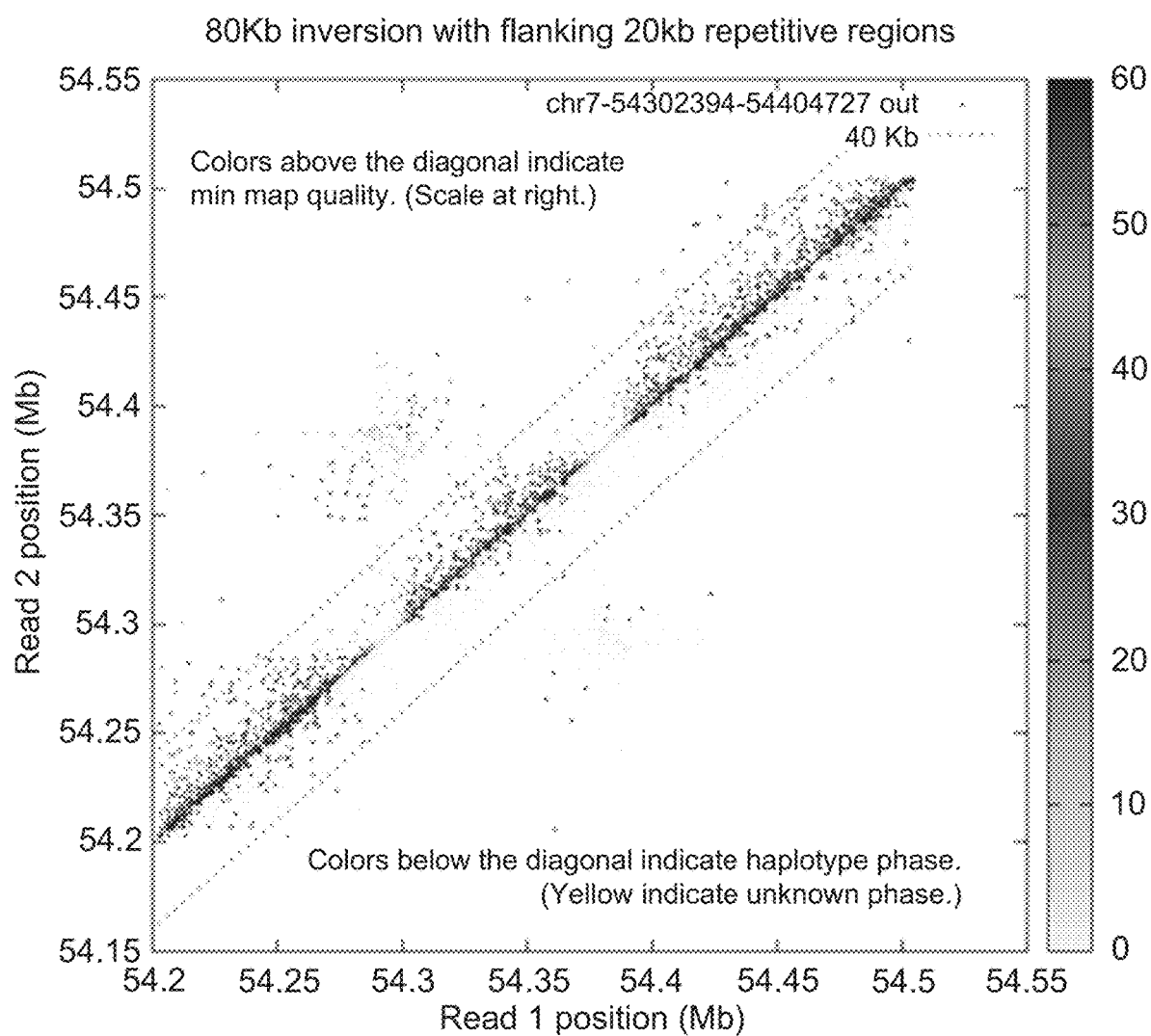
FIG. 9A and FIG. 9B illustrate the mapped locations on the GRCh38 reference sequence of read pairs are plotted in the vicinity of structural differences between GM12878 and the reference.
Figure 9B:
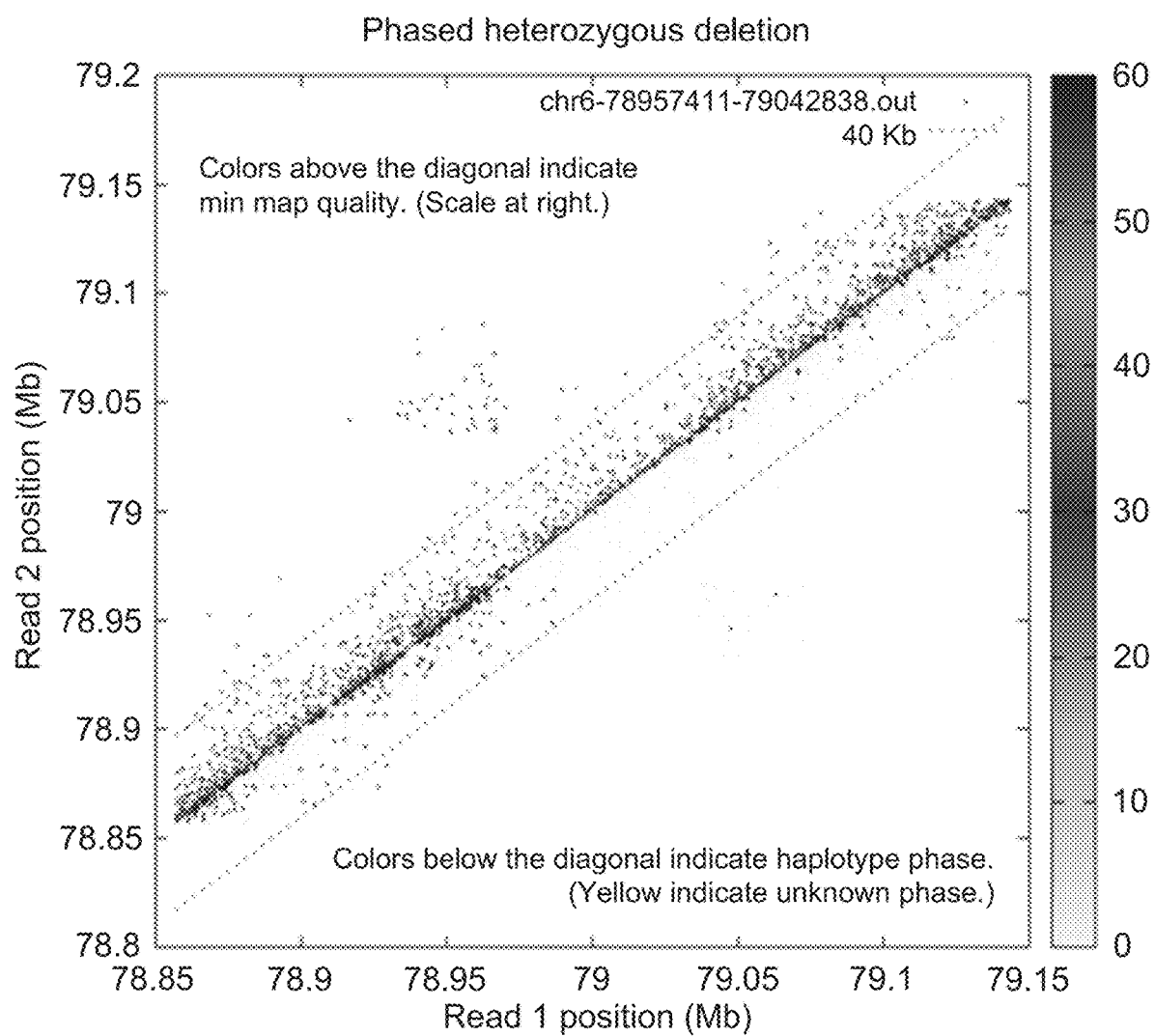

Referring to FIG. 9A and FIG. 9B, an example is provided of mapped locations on a reference sequence, e.g., GRCh38, of read pairs generated from proximity ligation of DNA from re-assembled chromatin are plotted in the vicinity of structural differences between GM12878 and the reference. Each read pair generated is represented both above and below the diagonal. Above the diagonal, shades indicates map quality score on scale shown; below the diagonal shades indicate the inferred haplotype phase of generated read pairs based on overlap with a phased SNPs. In some embodiments, plots generated depict inversions with flanking repetitive regions, as illustrated in FIG. 9B. In some embodiments, plots generated depict data for a phased heterozygous deletion, as illustrated in FIG. 9B.

Mapping paired sequence reads from one individual against a reference is the most commonly used sequence-based method for identifying differences in contiguous nucleic acid or genome structure like inversions, deletions and duplications (Tuzun et al., 2005). FIG. 9A and FIG. 9B show how read pairs generated by proximity ligation of DNA from re-assembled chromatin from GM12878 mapped to the human reference genome GRCh38 reveal two such structural differences. To estimate the sensitivity and specificity of the read pair data for identifying structural differences, a maximum likelihood discriminator on simulated data sets constructed to simulate the effect of heterozygous inversions was tested. The test data was constructed by randomly selecting intervals of a defined length L from the mapping of the NA12878 reads generated to the GRCh38 reference sequence and assigning each generated read pair independently at random to the inverted or reference haplotype, and editing the mapped coordinates accordingly. Non-allelic homologous recombination is responsible for much of the structural variation observed in human genomes, resulting in many variation breakpoints that occur in long blocks of repeated sequence (Kidd et al., 2008). The effect of varying lengths of repetitive sequence surrounding the inversion breakpoints was simulated by removing all reads mapped to within a distance W of them. In the absence of repetitive sequences at the inversion breakpoints, for 1 Kbp, 2 Kbp and 5 Kbp inversions respectively, the sensitivities (specificities) were 0.76 (0.88), 0.89 (0.89) and 0.97 (0.94) respectively. When 1 Kbp regions of repetitive (unmappable) sequence at the inversion breakpoints was used in a simulation, the sensitivity (specificity) for 5 Kbp inversions was 0.81 (0.76).

Performance

Analysis conducted with the techniques disclosed herein can be performed at high accuracy. Analysis can be conducted with an accuracy of at least about 50%, 60%, 70%, 75%, 80%, 85%, 90%, 95%, 96%, 97%, 98%, 99%, 99.9%, 99.99%, 99.999% or more. Analysis can be conducted with an accuracy of at least 70%. Analysis can be conducted with an accuracy of at least 80%. Analysis can be conducted with an accuracy of at least 90%.

Analysis conducted with the techniques disclosed herein can be performed at high specificity. Analysis can be conducted with a specificity of at least about 50%, 60%, 70%, 75%, 80%, 85%, 90%, 95%, 96%, 97%, 98%, 99%, 99.9%, 99.99%, 99.999% or more. Analysis can be conducted with a specificity of at least 70%. Analysis can be conducted with a specificity of at least 80%. Analysis can be conducted with a specificity of at least 90%.

Analysis conducted with the techniques disclosed herein can be performed at high sensitivity. Analysis can be conducted with a sensitivity of at least about 50%, 60%, 70%, 75%, 80%, 85%, 90%, 95%, 96%, 97%, 98%, 99%, 99.9%, 99.99%, 99.999% or more. Analysis can be conducted with a sensitivity of at least 70%. Analysis can be conducted with a sensitivity of at least 80%. Analysis can be conducted with a sensitivity of at least 90%.

Use of the techniques of the present disclosure can improve the functioning of the computer systems on which they are implemented. For example, the techniques can reduce the processing time for a given analysis by at least about 5%, 10%, 15%, 20%, 25%, 30%, 35%, 40%, 45%, 50%, 55%, 60%, 65%, 70%, 75%, 80%, 85%, 90%, 95%, or more. The techniques can reduce the memory requirements for a given analysis by at least about 5%, 10%, 15%, 20%, 25%, 30%, 35%, 40%, 45%, 50%, 55%, 60%, 65%, 70%, 75%, 80%, 85%, 90%, 95%, or more.

Use of the techniques of the present disclosure can enable conducting analyses that were previously not possible. For example, certain genetic features can be detected from sequence information that would not be detectable from such information without the methods of the present disclosure.

Computer Systems

Figure 10:
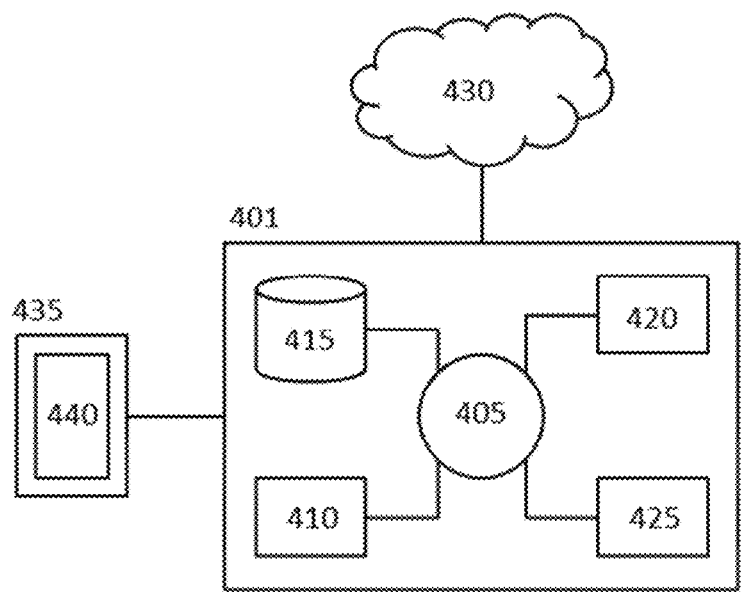
FIG. 10 shows an exemplary computer system that is programmed or otherwise configured to implement the methods provided herein.

FIG. 10 shows a computer system 1001 that is programmed or otherwise configured to implement the methods provided herein. The computer system 1001 can be an electronic device of a user or a computer system that is remotely located with respect to the electronic device. The electronic device can be a mobile electronic device.

The computer system 1001 includes a central processing unit (CPU, also "processor" and "computer processor" herein) 1005, which can be a single core or multi core processor, or a plurality of processors for parallel processing. The computer system 1001 also includes memory or memory location 1010 (e.g., random-access memory, read-only memory, flash memory), electronic storage unit 1015 (e.g., hard disk), communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communication bus (solid lines), such as a motherboard. The storage unit 1015 can be a data storage unit (or data repository) for storing data. The computer system 1001 can be operatively coupled to a computer network ("network") 1030 with the aid of the communication interface 1020. The network 1030 can be the Internet, an internet and/or extranet, or an intranet and/or extranet that is in communication with the Internet. The network 1030 in some cases is a telecommunication and/or data network. The network 1030 can include one or more computer servers, which can enable distributed computing, such as cloud computing. The network 1030, in some cases with the aid of the computer system 1001, can implement a peer-to-peer network, which may enable devices coupled to the computer system 1001 to behave as a client or a server.

The CPU 1005 can execute a sequence of machine-readable instructions, which can be embodied in a program or software. The instructions may be stored in a memory location, such as the memory 1010. The instructions can be directed to the CPU 1005, which can subsequently program or otherwise configure the CPU 1005 to implement methods of the present disclosure. Examples of operations performed by the CPU 1005 can include fetch, decode, execute, and writeback.

The CPU 1005 can be part of a circuit, such as an integrated circuit. One or more other components of the system 1001 can be included in the circuit. In some cases, the circuit is an application specific integrated circuit (ASIC).

The storage unit 1015 can store files, such as drivers, libraries and saved programs. The storage unit 1015 can store user data, e.g., user preferences and user programs. The computer system 1001 in some cases can include one or more additional data storage units that are external to the computer system 1001, such as located on a remote server that is in communication with the computer system 1001 through an intranet or the Internet.

The computer system 1001 can communicate with one or more remote computer systems through the network 1030. For instance, the computer system 1001 can communicate with a remote computer system of a user (e.g., service provider). Examples of remote computer systems include personal computers (e.g., portable PC), slate or tablet PC's (e.g., Apple® iPad, Samsung® Galaxy Tab), telephones. Smart phones (e.g., Apple® iPhone, Android-enabled device, Blackberry®), or personal digital assistants. The user can access the computer system 1001 via the network 1030.

Methods as described herein can be implemented by way of machine (e.g., computer processor) executable code stored on an electronic storage location of the computer system 1001, such as, for example, on the memory 1010 or electronic storage unit 1015. The machine executable or machine readable code can be provided in the form of software.

During use, the code can be executed by the processor 1005. In some cases, the code can be retrieved from the storage unit 1015 and stored on the memory 1010 for ready access by the processor 1005. In some situations, the electronic storage unit 1015 can be precluded, and machine-executable instructions are stored on memory 1010.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semi-conductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1001 can include or be in communication with an electronic display 1035 that comprises a user interface (UI) 1040 for providing, for example, an output or readout of the trained algorithm. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 1005.

Computer systems herein are in some cases configured to execute machine learning operations such as those disclosed in the specification herein or otherwise known to one of skill in the art.

Non-Sequencing Based Assays

Non-sequencing based assays, such as hybridization (e.g., labeling, array hybridization, fluorescent probe hybridization such as FISH, antibody hybridization) or amplification (e.g., PCR) can be employed to detect genetic features (e.g., genetic rearrangements) on DNA-protein complexes (e.g., chromatin) or other bound DNA complexes (e.g., DNA complexed with beads or other substrates).

DNA complexes (e.g., DNA-protein complexes such as chromatin or other bound DNA complexes) can be collected using techniques discussed herein. For example, DNA complexes can be recovered from preserved samples (e.g., FFPE samples) or reconstituted from isolated DNA. In an example, chromatin can be liberated from a preserved sample (e.g., an FFPE sample) by heat treatment and proteolysis.

DNA complexes can be captured or purified. For example, DNA complexes (e.g., chromatin) can be captured on a solid phase. In some cases, the solid phase comprises a carboxylated substrate, such as carboxylated paramagnetic beads.

DNA complexes can be fragmented and ligated by methods disclosed herein, including but not limited to enzymatic (e.g., restriction enzymes, fragmentase, transposase), thermal, and physical fragmentation. Ligation can be preceded by blunt ending.

DNA complexes can be partitioned for further analysis. For example, DNA complexes (e.g., chromatin) can be partitioned into droplets (e.g., microfluidic droplets), wells, array spots, or other partitions.

DNA complexes can be analyzed by a variety of means. Amplification (e.g., PCR) can be conducted (e.g., in a partition such as droplet PCR) targeting variant breakpoints (e.g., targeting with primer pairs). Hybridization assays, such as with fluorescent oligonucleotide probes, can be used to target variant breakpoints. Rearrangements can be detected by a change in signal due to changed probability of proximity ligation of nearby loci. In some cases. Taq-Man probes can be used. In some cases, SYBR probes can be used. Such an analysis can be multiplexed, for example in droplets, wells, array spots, or other partitions.

In an example, chromatin is liberated from a preserved sample (e.g., FFPE) by mild heat treatment and proteolysis. The liberated chromatin is captured on a solid phase comprising paramagnetic carboxylated polystyrene beads. DNA bound to the captured chromatin is fragmented (e.g., enzymatically) and fragmented ends are blunted. Blunt ended DNA associated with chromatin is ligated to other nearby DNA. The presence of inter-chromosomal variants is quantified, such as by droplet-based PCR or fluorescent oligonucleotide probe hybridization. Deletions and inversions change (e.g., increase) the signal due to a change (e.g., increase) in probability of proximity ligation of nearby loci.

Rearrangement assays can be combined with sequencing-based assays such as those described herein, including sequencing-based assays of rearrangement. For example, after a PCR or hybridization assay, chromatin can be sequenced and analyzed as disclosed herein.

Kits

Disclosed herein are kits for conducting the techniques disclosed herein. Kits can be contained in packaging such as boxes, with materials for a certain number of reactions in each unit of packaging. In some cases, a kit contains reagents for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more reactions.

Kits as disclosed herein comprise some or all reagents necessary to practice the methods and generate or analyze the compositions disclosed herein. In some cases the kits comprise a subset of reagents necessary to practice the methods and generate or analyze the compositions disclosed herein, and optionally include instructions relevant to reagents not included in a kit but often readily available from a reagent vendor.

Some kits disclosed herein comprise a buffer, a DNA binding agent, an affinity tag binding agent, deoxynucleotides, tagged deoxynucleotides, a DNA fragmenting agent, an end repair enzyme, a ligase, a protein removal agent, and instructions for use in obtaining genomic structural information from the preserved sample. Kits optionally comprise reagents for PCR, such as a buffer, nucleotides, a forward primer, a reverse primer, and a thermostable DNA polymerase.

Buffers in some kits comprise at least one of a restriction digest buffer, an end repair buffer, a ligation buffer, a TE buffer, a wash buffer, a TWB solution a NTB solution, a LWB solution, a NWB solution, and a crosslink reversal buffer. A representative digest buffer is a DpnII buffer, or a commercial buffer such as or functionally analogous to NEB buffer 2. Exemplary ligation buffers include T4 DNA ligase buffer, BSA, and Triton X-100.

Other exemplary reagents, either included in a kit or referred to in instructions for us in combination with kit reagents, include a TE buffer comprising tris and EDTA, a wash buffer comprising tris and sodium chloride, a TWB solution comprising one or more of tris, EDTA, and Tween 20, an NTB solution comprising one or more of tris, EDTA, and sodium chloride, an LWB solution comprising one or more of tris, lithium chloride, EDTA, and Tween 20, an NWB solution comprising at least one of tris, sodium chloride, EDTA, and Tween 20, and a crosslink reversal buffer comprising one or more of tris, SDS, and calcium chloride.

Some kits are configured to include or to be compatible with an affinity tag binding agent such as streptavidin beads, for example dynabeads.

Kits include or are compatible with nucleotides, such as dATP, dCTP, dGTP and dTTP, and in some cases biotinylated versions of the nucleotides.

DNA fragmenting agents included in kits herein or compatible therewith include at least one of a restriction enzyme such as DpnI, a transposase, a nuclease, a sonication device, a hydrodynamic shearing device, and a divalent metal cation.

End repair enzymes included in or compatible with kits herein comprise at least one of T4 DNA polymerase, klenow DNA polymerase, and T4 polynucleotide kinase An exemplary ligase in or compatible with kits herein includes T4 ligase.

Protein removal reagents included in or to be used in combination with kits herein include phenol and proteinases, such as proteinase K. *Streptomyces griseus* protease, a serine protease, a cysteine protease, a threonine protease, an aspartic protease, a glutamic protease, a metalloprotease, and an asparagine peptide lyase.

Kits optionally include or are compatible with solvents, such as solvents to be used to remove an embedding material such as paraffin.

Definitions

As used herein and in the appended claims, the singular forms "a," "and," and "the" include plural referents unless the context clearly dictates otherwise. Thus, for example, reference to "contig" includes a plurality of such contigs and reference to "probing the physical layout of chromosomes" includes reference to one or more methods for probing the physical layout of chromosomes and equivalents thereof known to those skilled in the art, and so forth.

Also, the use of "and" means "and/or" unless stated otherwise. Similarly. "comprise," "comprises," "comprising" "include," "includes," and "including" are interchangeable and not intended to be limiting.

It is to be further understood that where descriptions of various embodiments use the term "comprising." those skilled in the art would understand that in some specific instances, an embodiment can be alternatively described using language "consisting essentially of" or "consisting of."

The term "sequencing read" as used herein, refers to a fragment of DNA in which the sequence has been determined.

The term "contigs" as used herein, refers to contiguous regions of DNA sequence. "Contigs" can be determined by any number methods known in the art, such as, by comparing sequencing reads for overlapping sequences, and/or by comparing sequencing reads against databases of known sequences in order to identify which sequencing reads have a high probability of being contiguous.

The term "subject" as used herein can refer to any eukaryotic or prokaryotic organism.

The term "naked DNA" as used herein can refer to DNA that is substantially free of complexed proteins. For example, it can refer to DNA complexed with less than about 50%, about 40%, about 30%, about 20%, about 10%, about 5%, or about 1% of the endogenous proteins found in the cell nucleus.

The term "reconstituted chromatin" as used herein can refer to chromatin formed by complexing nucleic acid binding moieties to a nucleic acid such as naked DNA. In some cases these moieties are nucleic acid proteins such as nuclear proteins or histones, but other moieties such as nanoparticles are also contemplated.

The term "read pair" or "read-pair" as used herein can refer to two or more elements that are linked to provide sequence information. In some cases, the number of read-pairs can refer to the number of mappable read-pairs. In other cases, the number of read-pairs can refer to the total number of generated read-pairs.

A "tissue sample" as used herein, refers to a biological sample from an individual or an environment potentially comprising nucleic acids. Tumors, for example, are considered tissues, and a sample taken from a tumor constitutes a tissue sample, but in some cases the term refers to samples taken from a heterogeneous environment such as a stomach or intestine section, or an environmental sample comprising nucleic acids from a plurality of sources spatially distributed relative to one another.

"About," as used herein in reference to a number refers to that number +/−10% of that number. As used in reference to a range, 'about' refers to a range having a lower limit 10% less than the indicated lower limit of the range and an upper limit that is 10% greater than the indicated upper limit of the range.

A "probe" as used herein refers to a molecule that conveys information through binding to a target. Exemplary probes include olignonucleotide molecules and antibodies. Oligonucleotide molecules may act as probes by annealing to a target and conveying information either by changing a fluorescence characteristic, or alternately by annealing to a target and facilitating synthesis of a product such as an amplicon indicative of presence of the target. That is, the term probe as used herein variously contemplates antibody probes and other small molecule probes, as well as oligonucleic acid molecules, either acting by generating a signal directly through hybridization to a target leading to, for example, a change in fluorescence status, or acting by facilitating synthesis of an amplicon indicative of target presence.

As used herein, a DNA protein complex is destroyed or disrupted when proteins and nucleic acids are no longer assembled so as to form a complex. In some cases the complexes are completely denatured or disassembled, so that no protein DNA binding remains. Alternately, in some cases a DNA protein complex is substantially destroyed when a first nucleic acid segment and a second nucleic acid segment are no longer held together independent of any phosphodiester bond.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

The disclosure herein is further clarified in reference to a partial list of numbered embodiments as follows. 1. A method of obtaining genomic structural information from a preserved tissue sample comprising, isolating nucleic acids from the preserved tissue sample such that protein DNA complexes are not disrupted; tagging a protein DNA complex such that a first DNA segment and a second DNA segment are identified as arising from a common protein DNA complex; separating the first DNA segment and the second DNA segment from the common DNA complex; generating sequence information from the first DNA segment and the second DNA segment; and assigning sequence information sharing tag sequence indicative of a common protein DNA complex to a common genomic structure. 2. The method of any one of the above embodiments, such as embodiment 1, wherein the preserved tissue sample is a crosslinked paraffin-embedded tissue sample. 3. The method of any one of the above embodiments, such as embodiment 1, wherein the tag sequence comprises an oligo tag that identifies a complex. 4. The method of any one of the above embodiments, such as embodiment 1, wherein the tag sequence arises from ligating the first segment to the second segment. 5. The method of any one of the above embodiments, such as embodiment 1, wherein isolating nucleic acids from the preserved tissue sample such that protein DNA complexes are not disrupted comprises contacting the crosslinked paraffin-embedded tissue sample to xylene. 6. The method of any one of the above embodiments, such as embodiment 1, wherein isolating nucleic acids from the preserved tissue sample such that protein DNA complexes are not disrupted comprises contacting the preserved tissue sample to ethanol. 7. The method of any one of the above embodiments, such as embodiment 1, wherein isolating nucleic acids from the preserved tissue sample such that protein DNA complexes are not disrupted comprises protecting the sample from boiling conditions. 8. The method of any one of the above embodiments, such as embodiment 1, wherein separating the first DNA segment and the second DNA segment from the common DNA complex comprises proteinase K treatment. 9. The method of any one of the above embodiments, such as embodiment 1, wherein the preserved tissue sample preserves positional information reflective of its configuration in a tissue. 10. The method of any one of the above embodiments, such as embodiment 1, wherein the preserved tissue sample is not homogenized prior to isolating nucleic acids. 11. The method of any one of the above embodiments, such as embodiment 1, wherein the preserved tissue sample is stored for at least one week prior to isolating nucleic acids. 12. The method of any one of the above embodiments, such as embodiment 1, wherein the preserved tissue sample is stored for at least 6 months prior to isolating nucleic acids. 13. The method of any one of the above embodiments, such as embodiment 1, wherein the preserved tissue sample is transported from a collection point prior to isolating nucleic acids. 14. The method of any one of the above embodiments, such as embodiment 1, wherein the preserved tissue sample is collected in a sterile environment. 15. The method of any one of the above embodiments, such as embodiment 1, wherein the preserved tissue sample is positioned in a nonsterile environment prior to isolating nucleic acids. 16. A method of obtaining genomic structural information from a preserved tissue sample comprising isolating nucleic acids from the preserved tissue sample such that nucleic acid fragments of greater than 50 kb are recovered, contacting the nucleic acids to a plurality of nucleic acid binding moieties to form at least one complex such that a first DNA segment and a second DNA segment of a nucleic acid molecule are held together independent of their common phosphodiester backbone; cleaving at least one phosphodiester backbone of the at least one complex; tagging the at least one complex such that the first DNA segment and a second DNA segment are identified as arising from a common complex; separating the first DNA segment and the second DNA segment from the common complex; generating sequence information from the first DNA segment and the second DNA segment; and assigning sequence information sharing tag sequence indicative of a common protein DNA complex to a common genomic structure. 17. The method of any one of the above embodiments, such as embodiment 16, wherein the preserved tissue sample is a crosslinked paraffin embedded tissue sample. 18. The method of any one of the above embodiments, such as embodiment 16, wherein the tag sequence comprises an oligo tag that identifies a complex. 19. The method of any one of the above embodiments, such as embodiment 16, wherein the tag sequence arises from ligating the first DNA segment to the second DNA segment. 20. The method of any one of the above embodiments, such as embodiment 16, wherein isolating nucleic acids from the preserved tissue sample such that nucleic acid fragments of greater than 50 kb are recovered comprises contacting the preserved tissue sample to at least one of an anthranilate and a phosphanilate. 21. The method of any one of the above embodiments, such as embodiment 20, wherein the isolating is performed at a temperature not greater than 40 C. 22. The method of any one of the above embodiments, such as embodiment 16, wherein the isolating is performed at a temperature not greater than 40 C. 23. The method of any one of the above embodiments, such as embodiment 16, wherein separating the first DNA segment and the second DNA segment from the common DNA complex comprises proteinase K treatment. 24. The method of any one of the above embodiments, such as embodiment 16, wherein the plurality of nucleic acid binding moieties comprise nuclear proteins. 25. The method of any one of the above embodiments, such as embodiment 16, wherein the plurality of nucleic acid binding moieties comprise transposase. 26. The method of any one of the above embodiments, such as embodiment 16, wherein the plurality of nucleic acid binding moieties comprise histones. 27. The method of any one of the above embodiments, such as embodiment 16, wherein the plurality of nucleic acid binding moieties comprise nucleic acid binding proteins. 28. The method of any one of the above embodiments, such as embodiment 16, wherein the plurality of nucleic acid binding moieties comprise nanoparticles. 29. The method of any one of the above embodiments, such as embodiment 16, wherein cleaving at least one phosphodiester backbone of the at least one complex comprises contacting to a restriction endonuclease. 30. The method of any one of the above embodiments, such as embodiment 16, wherein cleaving at least one phosphodiester backbone of the at least one complex comprises contacting to a nonspecific endonuclease. 31. The method of any one of the above embodiments, such as embodiment 16, wherein cleaving at least one phosphodiester backbone of the at least one complex comprises shearing the DNA. 32. The method of any one of the above embodiments, such as embodiment 16, wherein cleaving at least one phosphodiester backbone of the at least one complex comprises contacting to a transposase. 33. The method of any one of the above embodiments, such as embodiment 16, wherein cleaving at least one phosphodiester backbone of the at least one complex comprises contacting to a topoisomerase. 34. The method of any one of the above embodiments, such as embodiment 16, wherein the preserved tissue sample preserves positional information reflective of its configuration in a tissue. 35. The method of any one of the above embodiments, such as embodiment 16, wherein the preserved tissue sample is not homogenized prior to isolating nucleic acids. 36. The method of any one of the above embodiments, such as embodiment 16, wherein the preserved tissue sample is stored for at least one week prior to isolating nucleic acids. 37. The method of any one of the above embodiments, such as embodiment 16, wherein the preserved tissue sample is stored for at least 6 months prior to isolating nucleic acids. 38. The method of any one of the above embodiments, such as embodiment 16, wherein the preserved tissue sample is transported from a collection point prior to isolating nucleic acids. 39. The method of any one of the above embodiments, such as embodiment 16, wherein the preserved tissue sample is collected in a sterile environment. 40. The method of any one of the above embodiments, such as embodiment 16, wherein the preserved tissue sample is positioned in a nonsterile environment prior to isolating nucleic acids. 41. A method of recovering spatially distributed genomic structural information from a tissue sample, comprising obtaining a tissue sample; extracting a portion from a first position of the fixed three-dimensional paraffin-embedded tissue sample; isolating nucleic acids from the portion from the first position such that protein DNA complexes are not disrupted; tagging a protein DNA complex such that a first DNA segment and a second DNA segment are identified as arising from a common protein DNA complex; separating the first DNA segment and the second DNA segment from the common DNA complex; generating sequence information from the first DNA segment and the second DNA segment; assigning sequence information sharing tag sequence indicative of a common protein DNA complex to a common genomic structure, and assigning the common genomic structure to the first position of the tissue sample. 42. The method of any one of the above embodiments, such as embodiment 41, wherein the tissue sample comprises a fixed three-dimensional paraffin-embedded tissue sample. 43. The method of any one of the above embodiments, such as embodiment 41, wherein the crosslinked paraffin-embedded tissue sample preserves positional information reflective of its configuration in a tissue. 44. The method of any one of the above embodiments, such as embodiment 41, wherein the crosslinked paraffin-embedded tissue sample is not homogenized prior to isolating nucleic acids. 45. The method of any one of the above embodiments, such as embodiment 41, wherein the crosslinked paraffin-embedded tissue sample is stored for at least one week prior to isolating nucleic acids. 46. The method of any one of the above embodiments, such as embodiment 41, wherein the crosslinked paraffin-embedded tissue sample is stored for at least 6 months prior to isolating nucleic acids. 47. The method of any one of the above embodiments, such as embodiment 41, wherein the crosslinked paraffin-embedded tissue sample is transported from a collection point prior to isolating nucleic acids. 48. The method of any one of the above embodiments, such as embodiment 41, wherein the crosslinked paraffin-embedded tissue sample is collected in a sterile environment. 49. The method of any one of the above embodiments, such as embodiment 41, wherein the crosslinked paraffin-embedded tissue sample is positioned in a nonsterile environment prior to isolating nucleic acids. 50. The method of any one of the above embodiments, such as embodiment 41, wherein the tag sequence comprises an oligo tag that identifies a complex. 51. The method of any one of the above embodiments, such as embodiment 41, wherein the tag sequence arises from ligating the first segment to the second segment. 52. The method of any one of the above embodiments, such as embodiment 41, wherein isolating nucleic acids from the crosslinked paraffin-embedded tissue sample such that protein DNA complexes are not disrupted comprises contacting the crosslinked paraffin-embedded tissue sample to xylene. 53. The method of any one of the above embodiments, such as embodiment 41, wherein isolating nucleic acids from the crosslinked paraffin-embedded tissue sample such that protein DNA complexes are not disrupted comprises contacting the crosslinked paraffin-embedded tissue sample to ethanol. 54. The method of any one of the above embodiments, such as embodiment 41, wherein isolating nucleic acids from the crosslinked paraffin-embedded tissue sample such that protein DNA complexes are not disrupted comprises protecting the sample from boiling conditions. 55. The method of any one of the above embodiments, such as embodiment 41, wherein separating the first DNA segment and the second DNA segment from the common DNA complex comprises proteinase K treatment. 56. The method of any one of the above embodiments, such as embodiment 41, wherein the tissue sample comprises a fixed three-dimensional paraffin-embedded tissue sample. 57. A method of reevaluating a treatment regimen trial outcome comprising obtaining data relating to the treatment regimen outcome in a patient population; obtaining fixed tissue samples from a plurality of patients of said patient population; extracting nucleic acid complexes from said fixed tissue samples; determining genomic structural information using said nucleic acid complexes for a plurality of said fixed tissue samples; and correlating the data relating to the treatment regimen outcome to the genomic structural information so as to identify genomic structural information relevant to the treatment regimen outcome. 58. The method of any one of the above embodiments, such as embodiment 57, wherein extracting nucleic acid complexes from said fixed tissue samples; and determining genomic structural information using said nucleic acid complexes for a plurality of said fixed tissue samples comprises the method of any one of the above embodiments, such as embodiment 1. 59. The method of any one of the above embodiments, such as embodiment 57, wherein extracting nucleic acid complexes from said fixed tissue samples; and determining genomic structural information using said nucleic acid complexes for a plurality of said fixed tissue samples comprises the method of any one of the above embodiments, such as embodiment 16. 60. The method of any one of the above embodiments, such as embodiment 57, wherein extracting nucleic acid complexes from said fixed tissue samples; and determining genomic structural information using said nucleic acid complexes for a plurality of said fixed tissue samples comprises the method of any one of the above embodiments, such as embodiment 41. 61. A method of nucleotide sequence assembly comprising: (a) providing a fixed tissue sample; (b) recovering a crosslinked DNA:protein complex from said fixed tissue sample; (c) ligating a first section of DNA from said crosslinked DNA:protein complex to a second section of DNA from said crosslinked DNA:protein complex, thereby forming a ligated DNA; (d) extracting said ligated DNA from said crosslinked DNA:protein complex; (e) sequencing at least a portion on either side of a ligation junction of said ligated DNA; and (f) using information from said sequencing to assemble a nucleotide sequence. 62. The method of any one of the above embodiments, such as embodiment 61, wherein said fixed tissue sample is formalin-fixed. 63. The method of any one of the above embodiments, such as embodiment 62, wherein said fixed tissue is formalin-fixed paraffin-embedded (FFPE). 64. The method of any one of the above embodiments, such as embodiment 61, wherein said crosslinked DNA:protein complex comprises chromatin. 65. The method of any one of the above embodiments, such as embodiment 61, wherein said ligating comprises blunt-end ligation. 66. The method of any one of the above embodiments, such as embodiment 61, further comprising, prior to said ligating, digesting DNA from said crosslinked DNA:protein complex. 67. The method of any one of the above embodiments, such as embodiment 66, wherein said digesting comprises restriction enzyme digestion. 68. The method of any one of the above embodiments, such as embodiment 66, further comprising, subsequent to said digesting, filling in sticky ends from said digesting to produce blunt ends. 69. The method of any one of the above embodiments, such as embodiment 68, wherein said filling in is performed using a biotinylated nucleotide. 70. The method of any one of the above embodiments, such as embodiment 61, wherein said recovering comprises binding DNA from said crosslinked DNA:protein complex to a solid support. 71. The method of any one of the above embodiments, such as embodiment 61, wherein said extracting comprises digesting protein from said crosslinked DNA:protein complex. 72. The method of any one of the above embodiments, such as embodiment 61, wherein said information comprises long-range information over a distance of more than 2000 base pairs (bp). 73. The method of any one of the above embodiments, such as embodiment 72, wherein said distance is more than 10,000 bp. 74. The method of any one of the above embodiments, such as embodiment 73, wherein said distance is more than 100,000 bp. 75. The method of any one of the above embodiments, such as embodiment 74, wherein said distance is more than 200,000 bp. 76. The method of any one of the above embodiments, such as embodiment 61, further comprising, prior to said recovering, dissolving an embedding material of said fixed tissue sample. 77. The method of any one of the above embodiments, such as embodiment 76, wherein said embedding material comprises paraffin. 78. The method of any one of the above embodiments, such as embodiment 61, wherein the crosslinked paraffin-embedded tissue sample preserves positional information reflective of its configuration in a tissue. 79. The method of any one of the above embodiments, such as embodiment 61, wherein the crosslinked paraffin-embedded tissue sample is not homogenized prior to isolating nucleic acids. 80. The method of any one of the above embodiments, such as embodiment 61, wherein the crosslinked paraffin-embedded tissue sample is stored for at least one week prior to isolating nucleic acids. 81. The method of any one of the above embodiments, such as embodiment 61, wherein the crosslinked paraffin-embedded tissue sample is stored for at least 6 months prior to isolating nucleic acids. 82. The method of any one of the above embodiments, such as embodiment 61, wherein the crosslinked paraffin-embedded tissue sample is transported from a collection point prior to isolating nucleic acids. 83. The method of any one of the above embodiments, such as embodiment 61, wherein the crosslinked paraffin-embedded tissue sample is collected in a sterile environment. 84. The method of any one of the above embodiments, such as embodiment 61, wherein the crosslinked paraffin-embedded tissue sample is positioned in a nonsterile environment prior to isolating nucleic acids. 85. A method of tissue sample analysis, comprising: (a) providing a fixed tissue sample; (b) collecting a first portion of said fixed tissue sample and a second portion of said fixed tissue sample, wherein said first portion and said second portion are from different regions of said fixed tissue sample, (c) recovering a first crosslinked DNA:protein complex from said first portion and a second crosslinked DNA:protein complex from said second portion; (d) (i) ligating a first section of DNA from said first crosslinked DNA:protein complex to a second section of DNA from said first crosslinked DNA:protein complex, thereby forming a first ligated DNA, and (ii) ligating a second section of DNA from said second crosslinked DNA:protein complex to a second section of DNA from said second crosslinked DNA:protein complex, thereby forming a second ligated DNA; (e) extracting said first ligated DNA from said first crosslinked DNA:protein complex and said second ligated DNA from said second crosslinked DNA:protein complex; (f) sequencing said first ligated DNA and said second ligated DNA; and (g) using information from said sequencing to assemble a first nucleotide sequence and a second nucleotide sequence. 86. The method of any one of the above embodiments, such as embodiment 85, wherein said fixed tissue sample is formalin-fixed. 87. The method of any one of the above embodiments, such as embodiment 86, wherein said fixed tissue is formalin-fixed paraffin-embedded (FFPE). 88. The method of any one of the above embodiments, such as embodiment 85, wherein said first crosslinked DNA:protein complex and said second crosslinked DNA:protein complex each comprise chromatin. 89. The method of any one of the above embodiments, such as embodiment 85, wherein said ligating in (dxi) and in (d)(ii) comprises blunt-end ligation. 90. The method of any one of the above embodiments, such as embodiment 85, further comprising, prior to said ligating in (d)(i) and in (d)(ii), digesting DNA from said first crosslinked DNA:protein complex and from said second crosslinked DNA:protein complex. 91. The method of any one of the above embodiments, such as embodiment 90, wherein said digesting comprises restriction enzyme digestion. 92. The method of any one of the above embodiments, such as embodiment 90, further comprising, subsequent to said digesting, filling in sticky ends from said digesting to produce blunt ends. 93. The method of any one of the above embodiments, such as embodiment 92, wherein said filling in is performed using a biotinylated nucleotide. 94. The method of any one of the above embodiments, such as embodiment 85, wherein said recovering comprises binding DNA from said first crosslinked DNA:protein complex and from said second crosslinked DNA:protein complex to a solid support. 95. The method of any one of the above embodiments, such as embodiment 85, wherein said extracting comprises digesting protein from said first crosslinked DNA:protein complex and from said second crosslinked DNA:protein complex. 96. The method of any one of the above embodiments, such as embodiment 85, wherein said information comprises long-range information over a distance of more than 2000 base pairs (bp). 97. The method of any one of the above embodiments, such as embodiment 96, wherein said distance is more than 10,000 bp. 98. The method of any one of the above embodiments, such as embodiment 97, wherein said distance is more than 100,000 bp. 99. The method of any one of the above embodiments, such as embodiment 98, wherein said distance is more than 200,000 bp. 100. The method of any one of the above embodiments, such as embodiment 85, further comprising, prior to said recovering, dissolving an embedding material of said fixed tissue sample. 101. The method of any one of the above embodiments, such as embodiment 100, wherein said embedding material comprises paraffin. 102. The method of any one of the above embodiments, such as embodiment 85, wherein the fixed tissue sample preserves positional information reflective of its configuration in a tissue. 103. The method of any one of the above embodiments, such as embodiment 85, wherein the fixed tissue sample is not homogenized prior to isolating nucleic acids. 104. The method of any one of the above embodiments, such as embodiment 85, wherein the fixed tissue sample is stored for at least one week prior to isolating nucleic acids. 105. The method of any one of the above embodiments, such as embodiment 85, wherein the fixed tissue sample is stored for at least 6 months prior to isolating nucleic acids. 106. The method of any one of the above embodiments, such as embodiment 85, wherein the fixed tissue sample is transported from a collection point prior to isolating nucleic acids. 107. The method of any one of the above embodiments, such as embodiment 85, wherein the fixed tissue sample is collected in a sterile environment. 108. The method of any one of the above embodiments, such as embodiment 85, wherein the fixed tissue sample is positioned in a nonsterile environment prior to isolating nucleic acids. 109. A method of detecting a genomic rearrangement from a preserved tissue sample comprising isolating protein DNA complexes from the preserved tissue sample such that protein DNA complexes are not destroyed; ligating exposed DNA ends of the complexes to form at least one paired end ligation product; contacting the at least one paired end ligation product to a pair of probes, wherein the pair of probes bind to a first region and a second region rearranged in a cell type. 110. The method of any one of the above embodiments, such as embodiment 109, wherein the protein DNA complexes are isolated such that a first segment and a second segment are held together independent of a phosphodiester backbone. 111. The method of any one of the above embodiments, such as embodiment 109, wherein the preserved sample is crosslinked. 112. The method of any one of the above embodiments, such as embodiment 109, wherein the pair of probes is labeled. 113. The method of any one of the above embodiments, such as embodiment 109, wherein the pair of probes comprises fluorophores. 114. The method of any one of the above embodiments, such as embodiment 109, wherein the pair of probes comprises oligonucleotide probes. 115. The method of any one of the above embodiments, such as embodiment 110, further comprising assaying for annealing of the pair of oligonucleic acids onto a common paired end ligation product. 116. The method of any one of the above embodiments, such as embodiment 115, further comprising sequencing at least some of the isolated nucleic acids. 117. The method of any one of the above embodiments, such as embodiment 109, wherein the pair of probes comprises a forward primer and a reverse primer, wherein at least one of the forward primer and the reverse primer anneal to DNA segments implicated in a rearrangement. 118. The method of any one of the above embodiments, such as embodiment 117, further comprising performing nucleic acid amplification using the forward primer and the reverse primer. 119. The method of any one of the above embodiments, such as embodiment 118, comprising sequencing at least some of the isolated nucleic acids. 120. The method of any one of the above embodiments, such as embodiment 109, wherein the genomic rearrangement is selected from an inversion, an insertion, a deletion, and a translocation. 121. The method of any one of the above embodiments, such as embodiment 109, wherein the preserved tissue sample is formalin-fixed. 122. The method of any one of the above embodiments, such as embodiment 109, wherein the preserved tissue is formalin-fixed paraffin-embedded (FFPE). 123. The method of any one of the above embodiments, such as embodiment 109, further comprising, prior to the isolating, removing an embedding material of the fixed tissue sample. 124. The method of any one of the above embodiments, such as embodiment 123, wherein the embedding material comprises paraffin. 125. The method of any one of the above embodiments, such as embodiment 109, wherein the isolating comprises contacting the preserved tissue sample to xylene. 126. The method of any one of the above embodiments, such as embodiment 109, wherein the isolating comprises contacting the preserved tissue sample to ethanol. 127. The method of any one of the above embodiments, such as embodiment 109, wherein the isolating comprises protecting the sample from boiling conditions. 128. The method of any one of the above embodiments, such as embodiment 109, wherein the isolating comprises contacting the crosslinked tissue sample to at least one of an anthranilate and a phosphanilate. 129. The method of any one of the above embodiments, such as embodiment 109, wherein the isolating is performed at a temperature not greater than 40° C. 130. The method of any one of the above embodiments, such as embodiment 109, wherein the crosslinked DNA:protein complex comprises chromatin. 131. The method of any one of the above embodiments, such as embodiment 109, wherein the isolating comprises binding DNA from the crosslinked DNA:protein complex to a solid support. 132. A method of detecting a genomic rearrangement in a DNA segment comprising obtaining genome locus interaction information for the DNA segment; and comparing an observed distribution of genome locus interaction information to an expected distribution of genome locus interaction information. 133. The method of any one of the above embodiments, such as embodiment 132, wherein a difference between the observed distribution and the expected distribution indicates a rearrangement of the DNA segment. 134. The method of any one of the above embodiments, such as embodiment 132, wherein the genome locus interaction information comprises paired end read pair information for ligated subsets of the DNA segment. 135. The method of any one of the above embodiments, such as embodiment 132, wherein the genomic rearrangement is selected from an inversion, an insertion, a deletion, and a translocation. 136. The method of any one of the above embodiments, such as embodiment 132, wherein an interaction frequency of the observed distribution is greater than the interaction frequency of the expected distribution and the genomic rearrangement comprises an inversion. 137. The method of any one of the above embodiments, such as embodiment 132, wherein an interaction frequency of the observed distribution is less than the interaction frequency of the expected distribution and the genomic rearrangement comprises a deletion. 138. The method of any one of the above embodiments, such as embodiment 132, wherein the DNA segment is obtained from a crosslinked tissue sample. 139. The method of any one of the above embodiments, such as embodiment 138, wherein the crosslinked tissue sample is formalin-fixed. 140. The method of any one of the above embodiments, such as embodiment 138, wherein the crosslinked tissue sample is formalin-fixed paraffin-embedded (FFPE). 141. The method of any one of the above embodiments, such as embodiment 138, wherein the crosslinked tissue sample is treated to isolate nucleic acids from the crosslinked tissue sample such that protein DNA complexes are not destroyed. 142. The method of any one of the above embodiments, such as embodiment 141, wherein the protein DNA complexes are isolated such that a first segment and a second segment are held together independent of a phosphodiester backbone. 143. The method of any one of the above embodiments, such as embodiment 141, wherein, prior to the treating, dissolving an embedding material of the fixed tissue sample is dissolved. 144. The method of any one of the above embodiments, such as embodiment 142, wherein the embedding material comprises paraffin. 145. The method of any one of the above embodiments, such as embodiment 141, wherein the treating comprises contacting the crosslinked paraffin-embedded tissue sample to xylene. 146. The method of any one of the above embodiments, such as embodiment 141, wherein the treating comprises contacting the crosslinked paraffin-embedded tissue sample to ethanol. 147. The method of any one of the above embodiments, such as embodiment 141, wherein the treating comprises protecting the sample from boiling conditions. 148. The method of any one of the above embodiments, such as embodiment 141, wherein the treating comprises contacting the crosslinked tissue sample to at least one of an anthranilate and a phosphanilate. 149. The method of any one of the above embodiments, such as embodiment 141, wherein the treating is performed at a temperature not greater than 40° C. 150. The method of any one of the above embodiments, such as embodiment 141, wherein the DNA protein complexes comprise chromatin. 151. A composition comprising a first DNA protein complex and a second DNA protein complex derived from a common preserved sample, wherein the first DNA protein complex comprises tagged DNA segments such that the segments are identified as arising from a common complex, and wherein the first DNA protein complex is assignable to a first location of the common preserved sample and the second DNA protein complex is assignable to a second location of the common preserved sample. 152. The composition of any one of the above embodiments, such as embodiment 151, wherein the tagged DNA segments are tagged using oligonucleotides having sequence indicative of a common complex. 153. The composition of any one of the above embodiments, such as embodiment 151, wherein the tagged DNA segments are tagged by ligation to form paired ends, such that unique sequence on either side of a ligation junction is assigned to a common complex. 154. The composition of any one of the above embodiments, such as embodiment 151, wherein the common preserved sample is contacted to a crosslinking agent. 155. The composition of any one of the above embodiments, such as embodiment 151, wherein the crosslinking agent comprises at least one of a formaldehyde or a formalin. 156. The composition of any one of the above embodiments, such as embodiment 151, wherein the crosslinking agent comprises at least one of UV light, mitomycin C, nitrogen mustard, melphalan, 1,3-butadiene diepoxide, cis diaminedichloroplatinum(II) and cyclophosphamide. 157. The composition of any one of the above embodiments, such as embodiment 151, wherein the preserved sample is formalin fixed paraffin-embedded (FFPE). 158. The composition of any one of the above embodiments, such as embodiment 151, wherein the preserved tissue sample is treated to isolate nucleic acids from the preserved tissue sample such that protein DNA complexes are not destroyed. 159. The method of any one of the above embodiments, such as embodiment 158, wherein the protein DNA complexes are isolated such that a first segment and a second segment are held together independent of a phosphodiester backbone. 160. The composition of any one of the above embodiments, such as embodiment 158, further comprising, prior to the treating, dissolving an embedding material of the preserved tissue sample. 161. The composition of any one of the above embodiments, such as embodiment 159, wherein the embedding material comprises paraffin. 162. The composition of any one of the above embodiments, such as embodiment 151, wherein the treating comprises contacting the crosslinked paraffin-embedded tissue sample to xylene. 163. The composition of any one of the above embodiments, such as embodiment 151, wherein the treating comprises contacting the crosslinked paraffin-embedded tissue sample to ethanol. 164. The composition of any one of the above embodiments, such as embodiment 151, wherein the treating comprises protecting the sample from boiling conditions. 165. The composition of any one of the above embodiments, such as embodiment 151, wherein the treating comprises contacting the crosslinked tissue sample to at least one of an anthranilate and a phosphanilate. 166. The composition of any one of the above embodiments, such as embodiment 151, wherein the treating is performed at a temperature not greater than 40° C. 167. The composition of any one of the above embodiments, such as embodiment 151, wherein the first DNA protein complex or the second DNA protein complex comprises chromatin. 168. A method, comprising obtaining a preserved sample from a subject, the sample comprising nucleic acids; and deriving genomic structural information by analyzing the nucleic acids in the sample. 169. The method of any one of the above embodiments, such as embodiment 168, wherein the preserved sample is crosslinked. 170. The method of any one of the above embodiments, such as embodiment 169, wherein the preserved sample is crosslinked using at least one of a formaldehyde, a formalin, UV light, mitomycin C, nitrogen mustard, melphalan, 1,3-butadiene diepoxide, cis diaminedichloroplatinum(II) and cyclophosphamide. 171. The method of any one of the above embodiments, such as embodiment 169, wherein the preserved sample is crosslinked using formalin. 172. The method of any one of the above embodiments, such as embodiment 168, wherein the preserved sample maintains positional information as to nucleic acids within it. 173. The method of any one of the above embodiments, such as embodiment 168, wherein the preserved sample is an embedded sample. 174. The method of any one of the above embodiments, such as embodiment 168, wherein the preserved sample is a formalin fixed paraffin-embedded (FFPE) sample. 175. The method of any one of the above embodiments, such as embodiment 168, wherein the genomic structural information is indicative of at least one of an inversion, an insertion, a deletion, and a translocation relative to a reference genome. 176. The method of any one of the above embodiments, such as embodiment 175, wherein the reference genome is a wild type genome of a species common to the subject. 177. The method of any one of the above embodiments, such as embodiment 175, wherein the reference genome is obtained from a reference tissue of the subject. 178. The method of any one of the above embodiments, such as embodiment 168, comprising deriving information indicative of phase status for a first segment and a second segment of the nucleic acids. 179. The method of any one of the above embodiments, such as embodiment 168, comprising tagging exposed nucleic acid ends of the sample so as to convey physical linkage information. 180. The method of any one of the above embodiments, such as embodiment 179, wherein the tagging comprises ligating oligonucleotides to a DNA protein complex released from the preserved sample such that the oligonucleotides convey information indicative of a common complex. 181. The method of any one of the above embodiments, such as embodiment 180, wherein the oligonucleotides comprise base sequence specific to a complex. 182. The method of any one of the above embodiments, such as embodiment 180, wherein the oligonucleotides comprise base sequence unique to a complex. 183. The method of any one of the above embodiments, such as embodiment 179, wherein the tagging comprises ligating a first nucleic acid segment of the complex to a second segment of the complex to form a paired end molecule. 184. The method of any one of the above embodiments, such as embodiment 183, comprising sequencing a portion of the first nucleic acid segment and a portion of the second nucleic acid segment. 185. The method of any one of the above embodiments, such as embodiment 184, comprising assigning contigs having unique sequence common to the portion of the first nucleic acid segment and contigs having unique sequence common to the portion of the second nucleic acid segment to a common scaffold in a nucleic acid assembly. 186. The method of any one of the above embodiments, such as embodiment 183, comprising contacting the paired end nucleic acid molecule to a set of nucleic acid probes. 187. The method of any one of the above embodiments, such as embodiment 186, wherein the set of nucleic acid probes are fluorescent probes. 188. The method of any one of the above embodiments, such as embodiment 186, wherein the set of nucleic acid probes anneal to a first locus and a second locus implicated in a genome structural rearrangement. 189. The method of any one of the above embodiments, such as embodiment 188, wherein the first locus and the second locus are not adjacent in a genome unaffected by the genome structural rearrangement. 190. The method of any one of the above embodiments, such as embodiment 188, wherein the first locus and the second locus are adjacent in a genome unaffected by the genome structural rearrangement. 191. The method of any one of any one of the above embodiments, such as embodiments 186-190, comprising sequencing nucleic acids of the sample when contacting the set of nucleic acid probes indicates a rearrangement. 192. The method of any one of the above embodiments, such as embodiment 183, comprising contacting the paired end nucleic acid molecule to a set of nucleic acid primers. 193. The method of any one of the above embodiments, such as embodiment 192, wherein the set of nucleic acid primers anneal to a first locus and a second locus implicated in a genome structural rearrangement. 194. The method of any one of the above embodiments, such as embodiment 193, wherein the set of nucleic acid primers yield an amplicon in a nucleic acid amplification reaction when the first locus and the second locus form a ligated paired end molecule. 195. The method of any one of the above embodiments, such as embodiment 193, wherein the set of nucleic acid primers do not yield an amplicon in a nucleic acid amplification reaction when the first locus and the second locus do not form a ligated paired end molecule. 1%. The method of any one of the above embodiments, such as embodiment 188, wherein the first locus and the second locus are not adjacent in a genome unaffected by the genome structural rearrangement. 197. The method of any one of the above embodiments, such as embodiment 188, wherein the first locus and the second locus are adjacent in a genome unaffected by the genome structural rearrangement. 198. The method of any one of any one of the above embodiments, such as embodiments 192-197, comprising sequencing nucleic acids of the sample when an amplicon is generated from the set of nucleic acid primers contacted to the paired end nucleic acid molecule. 199. The method of any one of the above embodiments, such as embodiment 169, wherein the preserved tissue sample is treated to isolate nucleic acids such that protein DNA complexes are not destroyed. 200. The method of any one of the above embodiments, such as embodiment 199, wherein the protein DNA complexes are isolated such that a first segment and a second segment are held together independent of a phosphodiester backbone. 201. The method of any one of the above embodiments, such as embodiment 199, wherein the preserved tissue sample is treated by contacting the preserved tissue sample to xylene. 202. The method of any one of the above embodiments, such as embodiment 199, wherein the preserved tissue sample is treated by contacting the preserved tissue sample to ethanol. 203. The method of any one of the above embodiments, such as embodiment 199, wherein the preserved tissue sample is treated by protecting the sample from boiling conditions. 204. The method of any one of the above embodiments, such as embodiment 199, wherein the preserved tissue sample is treated by contacting the preserved tissue sample to at least one of an anthranilate and a phosphanilate. 205. The method of any one of the above embodiments, such as embodiment 199, wherein the preserved tissue sample is treated at a temperature not greater than 40° C. 206. The method of any one of the above embodiments, such as embodiment 199, wherein the DNA protein complexes comprise chromatin. 207. The method of any one of the above embodiments, such as embodiment 168, wherein the preserved tissue sample preserves positional information reflective of its configuration in a tissue. 208. The method of any one of the above embodiments, such as embodiment 168, wherein the preserved tissue sample is not homogenized prior to isolating nucleic acids. 209. The method of any one of the above embodiments, such as embodiment 168, wherein the preserved tissue sample is stored for at least one week prior to isolating nucleic acids. 210. The method of any one of the above embodiments, such as embodiment 168, wherein the preserved tissue sample is stored for at least 6 months prior to isolating nucleic acids. 211. The method of any one of the above embodiments, such as embodiment 168, wherein the preserved tissue sample is transported from a collection point prior to isolating nucleic acids. 212. The method of any one of the above embodiments, such as embodiment 168, wherein the preserved tissue sample is collected in a sterile environment. 213. The method of any one of the above embodiments, such as embodiment 168, wherein the preserved tissue sample is positioned in a nonsterile environment prior to isolating nucleic acids. 214. A kit for obtaining genomic structural information from a preserved sample comprising: a buffer, a DNA binding agent, an affinity tag binding agent, deoxynucleotides, tagged deoxynucleotides, a DNA fragmenting agent, an end repair enzyme, a ligase, a protein removal agent, and instructions for use in obtaining genomic structural information from the preserved sample. 215. The kit of any one of the above embodiments, such as embodiment 214, further comprising reagents for PCR. 216. The kit of any one of the above embodiments, such as embodiment 215, wherein reagents for PCR comprise a buffer, nucleotides, a forward primer, a reverse primer, and a thermostable DNA polymerase. 217. The kit of any one of the above embodiments, such as embodiment 214, wherein the buffer comprises at least one of a restriction digest buffer, an end repair buffer, a ligation buffer, a TE buffer, a wash buffer, a TWB solution a NTB solution, a LWB solution, a NWB solution, and a crosslink reversal buffer. 218. The kit of any one of the above embodiments, such as embodiment 217, wherein the restriction digest buffer comprises a DpnII buffer. 219. The kit of any one of the above embodiments, such as embodiment 217, wherein the end repair buffer comprises NEB buffer 2. 220. The kit of any one of the above embodiments, such as embodiment 217, wherein the ligation buffer comprises T4 DNA ligase buffer, BSA, and Triton X-100. 221. The kit of any one of the above embodiments, such as embodiment 217, wherein the TE buffer comprises tris and EDTA. 222. The kit of any one of the above embodiments, such as embodiment 217, wherein the wash buffer comprises tris and sodium chloride. 223. The kit of any one of the above embodiments, such as embodiment 217, wherein the TWB solution comprises tris, EDTA, and Tween 20. 224. The kit of any one of the above embodiments, such as embodiment 217, wherein the NTB solution comprises tris, EDTA, and sodium chloride. 225. The kit of any one of the above embodiments, such as embodiment 217, wherein the LWB solution comprises tris, lithium chloride, EDTA, and Tween 20. 226. The kit of any one of the above embodiments, such as embodiment 217, wherein the NWB solution comprises tris, sodium chloride. EDTA, and Tween 20. 227. The kit of any one of the above embodiments, such as embodiment 217, wherein the cross-link reversal buffer comprises tris, SDS, and calcium chloride. 228. The kit of any one of the above embodiments, such as embodiment 214, wherein the DNA binding agent comprises chromatin capture beads. 229. The kit of any one of the above embodiments, such as embodiment 228, wherein the chromatin capture beads comprise a PEG-800 powder, a tris buffer, sodium chloride, EDTA, a surfactant, TE buffer, and sera-mag beads. 230. The kit of any one of the above embodiments, such as embodiment 214, wherein the affinity tag binding agent comprises streptavidin beads. 231. The kit of any one of the above embodiments, such as embodiment 230, wherein the streptavidin beads comprise dynabeads. 232. The kit of any one of the above embodiments, such as embodiment 214, wherein the deoxynucleotides comprise at least three of dATP, dTTP, dGTP, and dCTP. 233. The kit of any one of the above embodiments, such as embodiment 214, wherein the biotinylated deoxynucleotide comprises at least one of biotinylated dCTP, biotinylated dATP, biotinylated dTTP, and biotinylated dGTP. 234. The kit of any one of the above embodiments, such as embodiment 214, wherein the DNA fragmenting agent is at least one of a restriction enzyme, a transposase, a nuclease, a sonication device, a hydrodynamic shearing device, and a divalent metal cation. 235. The kit of any one of the above embodiments, such as embodiment 234, wherein restriction enzyme comprises DpnII. 236. The kit of any one of the above embodiments, such as embodiment 214, wherein the end repair enzyme comprises at least one of T4 DNA polymerase, klenow DNA polymerase, and T4 polynucleotide kinase. 237. The kit of any one of the above embodiments, such as embodiment 214, wherein the ligase comprises a T4 DNA ligase. 238. The kit of any one of the above embodiments, such as embodiment 214, wherein the protein removal agent comprises at least one of a protease and a phenol. 239. The kit of any one of the above embodiments, such as embodiment 238, wherein the protease comprises at least one of a proteinase K, a *Streptomyces griseus* protease, a serine protease, a cysteine protease, a threonine protease, an aspartic protease, a glutamic protease, a metalloprotease, and an asparagine peptide lyase. 240. The kit of any one of the above embodiments, such as embodiment 214, further comprising a solvent for removing an embedding material. 241. The kit of any one of the above embodiments, such as embodiment 240, wherein the solvent is at least one of a xylene, a benzene, and a toluene.

The following examples are intended to illustrate but not limit the disclosure. While they are typical of those that might be used, other procedures known to those skilled in the art may alternatively be used.

EXAMPLES

Example 1. Read-Pair Library Generation from FFPE-Sample

AJ GIAB ('Genome In A Bottle') samples GM24149 (father) and GM24385 (son) were procured from Horizon Discovery. The cell lines had been previously embedded in FFPE. Sections approximately 15-20 microns thick containing about $3 \times 10^5$ cells per section were used in this experiment. The sections were washed with xylene to remove the paraffin wax. The xylene was removed by washing the sections with ethanol. The released tissue samples were then re-suspended in a detergent buffer. Samples containing nucleic acids were then subjected to end ligation, which involves digesting the DNA with a restriction enzyme, in this example Mbo1, then filling in the resulting overhangs with biotinylated nucleotides. The blunt ends were ligated together followed by release of the ligated ends. Biotinylated fragments were obtained and end sequenced, and read pairs were taken to indicate that the contigs to which each mapped were physically linked on a common nucleic acid molecule in the sample.

Sequencing was performed in order to determine the distance between paired ends of the recovered fragments by comparing the location of the isolated sequences to a genome assembly. Results revealed that the FFPE-Chicago method (Table 1—GIAB column) resulted in long distance read pair frequencies comparable to (>200 kbp insert) or greater than (100 kbp-200 kbp inserts) Chicago methods performed on non-FFPE samples (Table 1—Chicago columns). These data were also analyzed to determine the complexity and raw sequencing coverage of the FFPE-Chicago library (Table 2). Complexity of a library refers to the variety of different molecules within the library.

TABLE 1

Insert length frequencies.

|  | GIAB | CHICAGO | CHICAGO |
|---|---|---|---|
| 0 < Insert <= 2 kbp | 48.078% | 20.731% | 9.92% |
| 2 kbp < Insert <= 10 kbp | 0.458% | 6.045% | 1.811% |
| 10 kbp < Insert <= 100 kbp | 0.553% | 5.356% | 1.884% |
| 100 kbp < Insert <= 200 kbp | 0.171% | 0.022% | 0.044% |
| 200 kbp < Insert | 1.49% | 1.828% | 1.499% |

TABLE 2

Complexity and Raw physical coverage

|  | FFPE | CHICAGO |
|---|---|---|
| Library Complexity (Poisson) | 229,196,982 | 1,013,303,912 |
| Raw Physical Coverage scaled to 150M read pairs | 5.622 X | 66.343 X |

Example 2. Phase Determination from FFPE-Chicago Libraries

The sequencing data generated in Example 1 was used to determine phasing information of sets of SNPs known to be in the starting GIAB sample. In other words, the sequencing data was used to determine if sets of SNPs were present on the same or different DNA molecules. These data were then compared to the known sequence of the GIAB sample to determine the accuracy of the phase-calling.

Each of the Bins in Table 3 shows the number of SNPs found and which are concordant up until the size of the next bin. For example, the first line shows that between 0-10,000, there were 132796 SNPS found and 99.059% were in the correct phase. A high concordance (>95%) is seen up until about 1.5 MB (with the exception of the 70-80 kb bin, which missed 1 of 13 and the 1.1-1.3 MB bin which missed 2 of 15). In the 1.7-1.9 MB range, 7 of 7 SNP pair phases were properly called.

From these data, it is concluded that, despite low levels of spurious linkage, proper long-range information is determined using the FFPE-Chicago method, even up to the megabase range. Importantly, these 'concordance' prediction rates are 95% or greater, significantly higher than the 50% success rate one would expect from random chance).

TABLE 3

SNPs in each bin.

| Bin | Concordance | Concordant n | Discordant n | Total Read Pairs |
|---|---|---|---|---|
| 0 | 99.059 | 131547 | 1249 | 132796 |
| 10000 | 99.346 | 152 | 1 | 153 |
| 20000 | 100 | 60 | 0 | 60 |
| 30000 | 97.619 | 41 | 1 | 42 |
| 40000 | 97.222 | 35 | 1 | 36 |
| 50000 | 100 | 26 | 0 | 26 |
| 60000 | 100 | 26 | 0 | 26 |
| 70000 | 92.308 | 12 | 1 | 13 |
| 80000 | 100 | 18 | 0 | 18 |
| 90000 | 100 | 8 | 0 | 8 |
| 100000 | 98.148 | 159 | 3 | 162 |
| 300000 | 95.238 | 80 | 4 | 84 |
| 500000 | 98 | 49 | 1 | 50 |
| 700000 | 100 | 28 | 0 | 28 |
| 900000 | 96.552 | 28 | 1 | 29 |
| 1100000 | 86.667 | 13 | 2 | 15 |
| 1300000 | 100 | 16 | 0 | 16 |
| 1500000 | 78.571 | 11 | 3 | 14 |
| 1700000 | 100 | 7 | 0 | 7 |
| 1900000 | 85.714 | 6 | 1 | 7 |
| 2000000 | 87.097 | 27 | 4 | 31 |
| 3000000 | 72.222 | 26 | 10 | 36 |
| 4000000 | 84 | 21 | 4 | 25 |
| 5000000 | 69.565 | 16 | 7 | 23 |
| 6000000 | 52.941 | 9 | 8 | 17 |
| 7000000 | 77.778 | 7 | 2 | 9 |
| 8000000 | 61.111 | 11 | 7 | 18 |
| 10000000 | 64.183 | 267 | 149 | 416 |

Example 3. Improving DNA Extraction

Changing the detergent buffer from an SDS containing buffer to a triton X containing buffer is made and visualization of the pellet described in Example 1 resulted in increased DNA extraction. Subsequent library analysis revealed this library had increased complexity while maintaining a high level of long reads when compared to the library described in Examples 1 and 2. Results are shown in Table 4.

Human sample 1 data was collected from a GIAB sample treated as described in Example 1 (blunt end ligation performed on FFPE sample). All DNA from the sample was used in the library preparation.

Human sample 2 data was collected from a second GIAB sample treated as described in Example 1 (blunt end ligation performed on FFPE sample). All DNA from the sample was used in the library preparation.

Human sample 3 data was collected from a third GIAB sample treated as described in Example 1 (blunt end ligation performed on FFPE sample). Approximately 500 ng of DNA from the sample was used in the library preparation.

Human sample 4 data was collected from a third GIAB sample (same sample as Human sample 3) treated as described in Example 1 (blunt end ligation performed on FFPE sample). Approximately 50 ng of DNA from the sample was used in the library preparation.

Human sample 5 data was collected from a third GIAB sample (same sample as Human sample 3 and 4) treated as described in Example 1 (blunt end ligation performed on FFPE sample). Approximately 10 ng of DNA from the sample was used in the library preparation.

TABLE 4

Results with improved DNA extraction.

| Project | Human (1) | Human (2) | Human (3) |
|---|---|---|---|
| Library ID | DPH593_chicago_miseq | DPH594_chicago_miseq | DPH595_chicago_miseq |
| PCR/Optical Duplicates | 0.166% | 0.17% | 0.179% |
| Unmapped | 8.157% | 8.364% | 8.263% |
| Low Map Quality | 10.12% | 10.134% | 9.99% |
| Different Scaffold | 16.481% | 16.374% | 13.779% |
| 0 < Insert <= 2 kbp | 57.001% | 56.383% | 60.844% |
| 2 kbp < Insert <= 10 kbp | 1.661% | 1.794% | 1.456% |
| 10 kbp < Insert <= 100 kbp | 1.438% | 1.57% | 1.245% |
| 100 kbp < Insert <= 200 kbp | 0.44% | 0.476% | 0.382% |
| 200 kbp < Insert | 4.536% | 4.735% | 3.861% |
| Library Complexity (Poisson) | 1,295,157,213 | 1,144,409,461 | 1,321,625,959 |
| Raw Physical Coverage scaled to 150M read pairs | 15.426 X | 16.808 X | 13.372 X |

| Project | Human (4) | Human (5) |
|---|---|---|
| Library ID | DPH596_chicago_miseq | DPH597_chicago_miseq |
| PCR/Optical Duplicates | 0.546% | 1.717% |
| Unmapped | 8.559% | 8.358% |
| Low Map Quality | 9.809% | 9.628% |
| Different Scaffold | 10.576% | 10.557% |
| 0 < Insert <= 2 kbp | 65.109% | 64.924% |
| 2 kbp < Insert <= 10 kbp | 1.154% | 1.001% |
| 10 kbp < Insert <= 100 kbp | 0.979% | 0.859% |
| 100 kbp < Insert <= 200 kbp | 0.303% | 0.266% |
| 200 kbp < Insert | 2.965% | 2.69% |
| Library Complexity (Poisson) | 497,115,139 | 107,132,825 |
| Raw Physical Coverage scaled to 150M read pairs | 10.616 X | 9.447 X |

Example 4. Unsuccessful DNA Extraction from FFPE Samples

BA tumor sample is biopsied from a cancer patient and fixed with formalin prior to embedding in paraffin. The FFPE-sample is then stored. Six months later, the patient enters a clinical study with the aim of tracking tumor progression while being treated with a new compound. During treatment FFPE tumor biopsy samples are prepared every few weeks and stored. The patient responds very well to the treatment and the clinical team is interested in learning more about the patient's specific cancer subtype. To determine the structural variations present in the tumor at each stage of the study, the clinical team attempts to extract DNA from the FFPE tumor samples. Unfortunately, the DNA recovered is highly fragmented and only short fragments reads are recovered. These short fragment reads are inadequate for determining structural variation and therefore, critical clinical information is lost.

Example 5. Successful Long-Distance Data from Native Chromatin in FFPE Samples The FFPE tumor samples from Example 4 are processed in a gentle way in order to preserve native DNA-protein complexes. DNA extract is performed by washing the FFPE samples with xylene in order to remove the paraffin wax. The xylene is removed by washing with ethanol. The sample is then re-suspended in a detergent buffer before undergoing Hi-C processing. Fixed DNA protein complexes isolated from the FFPR sample are digested to generate sticky overhangs which are filled in with biotin labeled nucleotides. The resulting blunt ends are ligated together to generate paired ends of DNA sequences originating from the same DNA protein complex. The paired ends are released from the DNA protein complexes by DNA shearing and isolated using streptavidin beads. The recovered paired ends are ligated to sequencing adapters and sequenced to generate a read pair library.

The clinical team is able to analyze the read pair library to determine the structural variations of the patient's tumor over time, including the sample taken six months prior to the study. These data are used to determine the subtype of the cancer and in order to inform treatment prognosis of other patients with the same cancer subtype.

Example 6. Successful Long-Distance Data from Reconstituted Chromatin from FFPE Samples DNA is extracted from FFPE samples as described in Example 5. Naked DNA is isolated and size selected for fragments over 50 kb in length. Reconstituted chromatin is generated by binding the size-selected DNA to purified chromatin proteins such that each DNA protein complex comprises a single DNA molecule. These DNA proteins are then crosslinked using formaldehyde. The crosslinked complexes are then digested and treated to generate paired ends from DNA sequences originating from the same DNA molecule. The paired ends are sequenced in order to generate read pair libraries. Data from the read pair libraries reveal long-distance sequence information used to determine phasing and structural variation information useful in characterizing the tumor sample of the above-described patient.

Example 7. Determining Genomic Heterogeneity from FFPE-Samples

The FFPE samples from Example 4 are used in a study to determine the genomic heterogeneity in different regions of the tumor. Punch biopsies are taken from different segments of the FFPE tumor sample and then processed as described in Example 5. The generated data is used to determine the growing edge of the tumor and to learn how mutations and structural variations progress and accumulate or disappear during tumor growth or regression due to treatment with the novel compound described in Example 5.

Example 8. Solubilization of FFPE and Sample Lysis

One milliliter of xylene is added to an FFPE sample and vortexed until the paraffin is dissolved. The sample is centrifuged at 14,000 revolutions per minute for two minutes. Xylene is gently removed. One milliliter of 100% ethanol is added and the sample is vortexed to detach the cell pellet from the inner wall of the tube. The sample is centrifuged again at max speed for two minutes and then the ethanol is then removed. The pellet is allowed to air dry. Once the pellet is fully dry, 50 microliters of lysis buffer (50 mM Tris pH 8, 50 mM NaCl, 1% SDS, 0.15% Triton, 1 mM EDTA) is added to the sample. The sample is incubated at 37° C. for 15 minutes while being lightly shaken. The entire sample is then transferred to a 1.5 mL tube. The sample is repeatedly pipetted to break up the cell pellet. To the sample, 100 µL of SPRI (solid phase reversible immobilization) beads are then added in a 2:1 ratio of SPRI beads to soluble chromatin followed by incubation at room temperature for 10 minutes. The SPRI beads are then washed twice. The SPRI-bead isolated sample is then used for down-stream techniques such as Chicago or Hi-C.

Example 9: FFPE Samples Preserve Long-Range Genomic Linkage Information

Figure 11A:
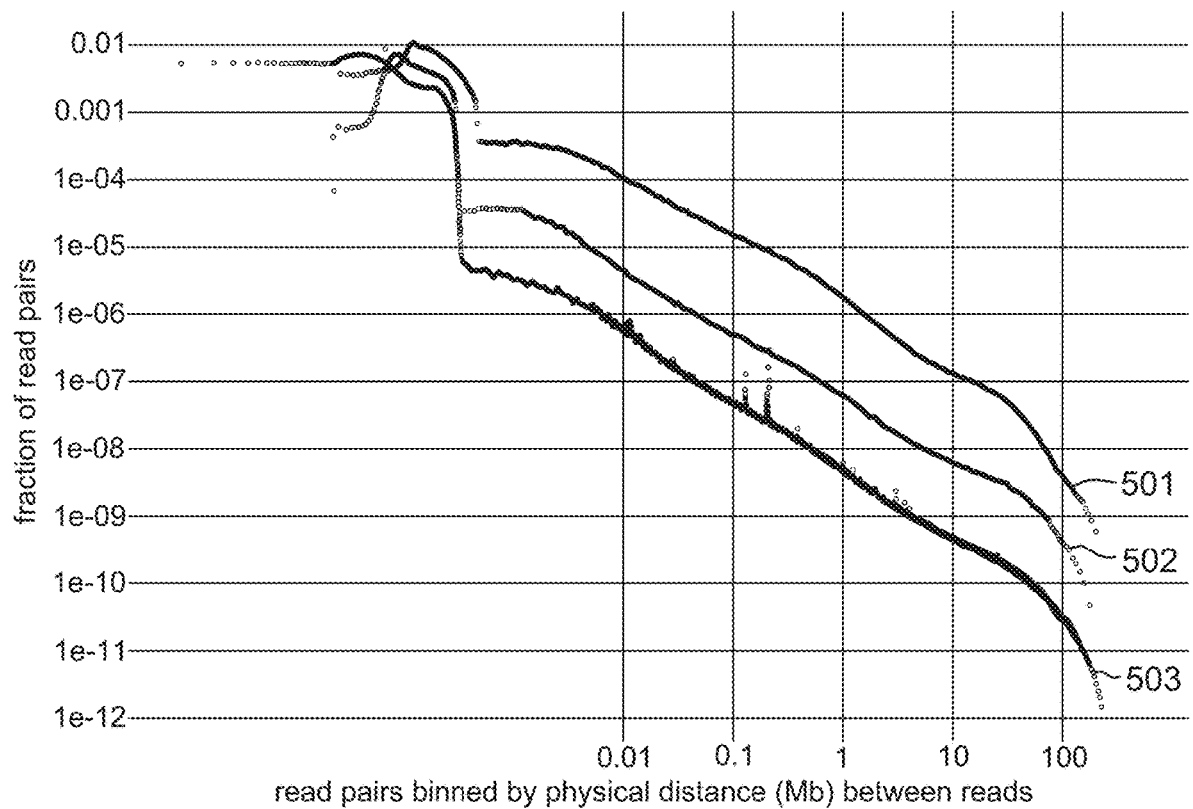
FIG. 11A shows results from analysis of FFPE tissue and FFPE cell culture samples by methods of the present disclosure, with comparison to cell culture analyzed by Hi-C.

FFPE samples were obtained and processed according to methods of the present disclosure to extract genomic linkage data. FIG. 11A shows the results from analysis of three samples. Human cell culture (red, 1103) and spleen tissue (green, 1102) FFPE samples were obtained and processed according to methods of the present disclosure to extract genomic linkage data. Paired ends were mapped to the hg19 reference, and the physical distance between reads of each read pair was calculated. These data were compared against data prepared using a cell culture sample with a Hi-C method (blue, 1101). The x-axis shows read pairs binned by physical distance (Mb) between reads (axis numbers from left to right of 0.01, 0.1, 1, 10, and 100). The y-axis shows the fraction of read pairs (axis numbers from top to bottom of 0.01, 0001, $10^{-4}$, $10^{-5}$, $10^{-6}$, $10^{-7}$, $10^{-8}$, $10^{-9}$, $10^{-10}$, $10^{-11}$, and $10^{-12}$).

Figure 11B:
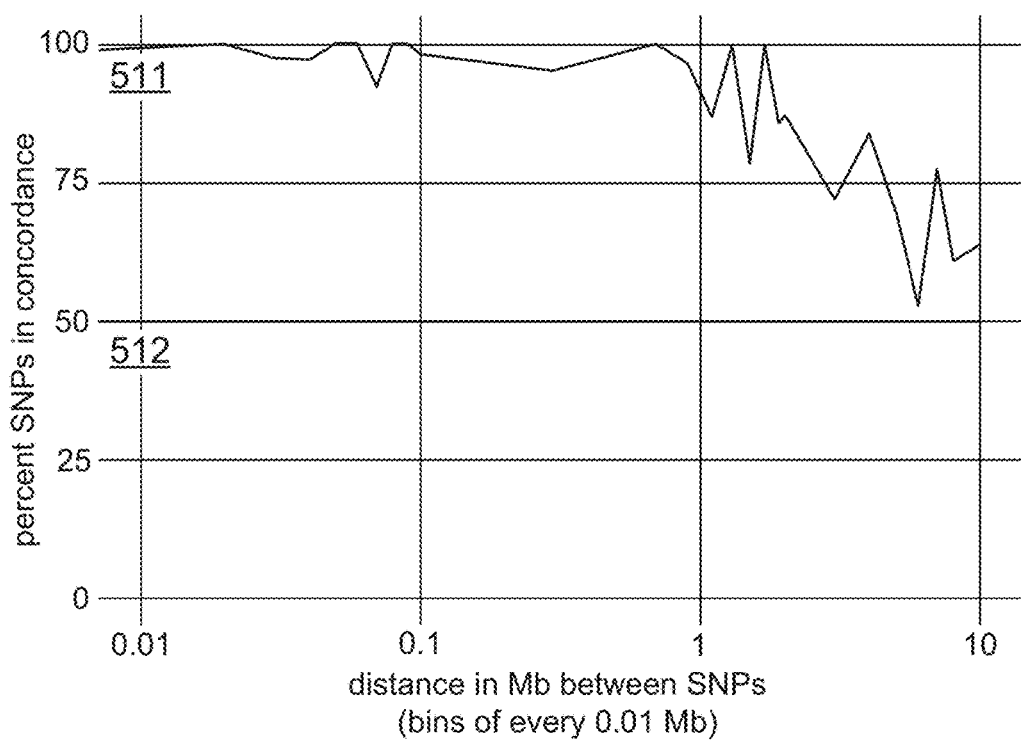
FIG. 11B, FIG. 11C, and FIG. 11D show results from analysis of an Ashkenazi father (GM24149) cell culture FFPE sample to generate long-range genomic linkage data

Example 10: SNP Concordance in a FFPE Sample Processed to Extract Long-Range Genomic Linkage Information FIG. 11B shows results from analysis of an Ashkenazi father (GM24149) cell culture FFPE sample was processed to generate long-range genomic linkage data according to methods of the present disclosure. These data were filtered for high confidence SNPs present in both paired end reads. This filtered dataset was organized into bins based on the physical distance between the two reads (x-axis), and the percent of SNP pairs in concordance was calculated for each bin (y-axis). The upper, red line (1111) shows SNPs in concordance, and the lower, blue line (1112) shows random concordance for reference.

Example 11: FFPE Samples Preserve Long-Range Genomic Linkage Information that Permit Structural Variation (SV) Identification Data were also extracted from an Ashkenazi father (GM24149) cell culture FFPE sample and analyzed for the presence of structural variants by mapping read pairs against the hg19 reference. The midpoints of paired reads were plotted on the x-axis and corresponding physical separation on the y-axis of FIG. 11C and FIG. 11D. The map quality score is shown by the grayscale of each data point as shown in the legend.

Figure 11C:
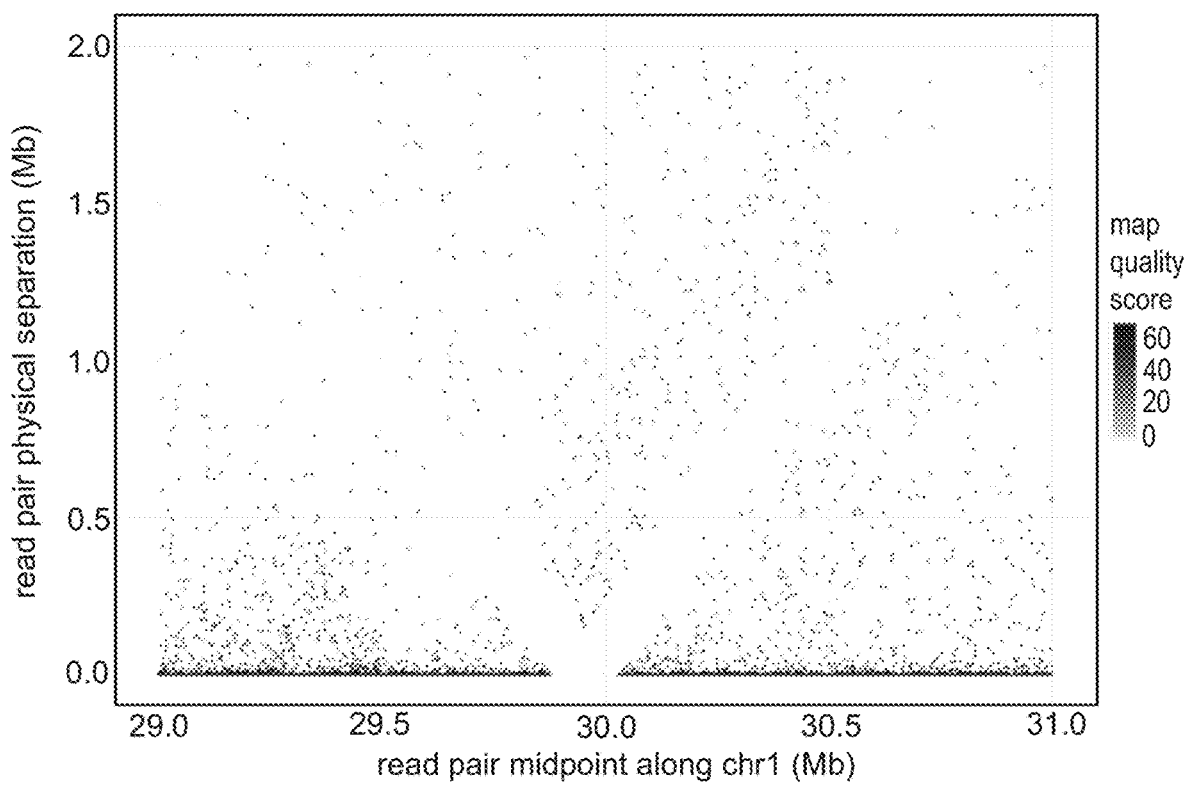

FIG. 11C shows that a ~100 Kb chromosome 1 deletion is evident based on the low density of read pairs with midpoints that correspond with the missing genome segment.

Figure 11D:
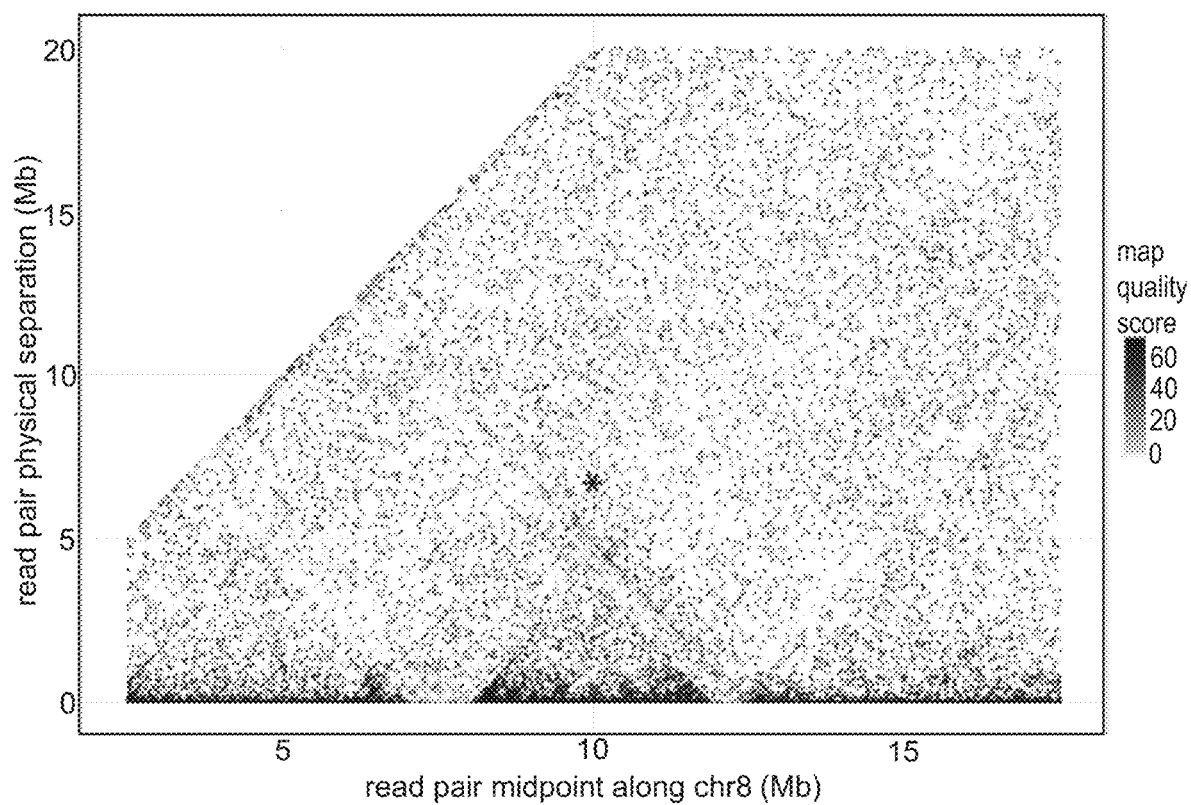

FIG. 11D shows that a ~4 Mb chromosome 8 inversion is evident based on the higher than expected density of reads below the asterisk. Inversions are commonly flanked by repetitive regions that generally yield low map quality scores.

Example 12. Sample Collection, Subsequent Analysis, and Treatment Selection

A patient undergoes surgery to remove a tissue. The tissue is excised in a sterile environment and deposited in formalin. No homogenization of the tissue occurs pursuant to collection.

The tissue is preserved and the patient is monitored. The patient is observed to undergo regrowth at the site of excision. The tissue is subjected to analysis in a laboratory setting, including excision of nucleic acid protein complexes from positions including the interior and the perimeter of the preserved tissue.

Genomic information is obtained from nucleic acid protein complexes obtained from the preserved tissue. A genomic rearrangement is identified from perimeter tissue that indicates a particular genomic configuration implicated in tumor metastasis.

A chemotherapeutic treatment is selected based upon known efficacy relative to the genomic configuration implicated in tumor metastasis. The patient is administered the chemotherapeutic treatment and the tumor is observed to cease regrowth.

Example 13. Drug Trial Reassessment

A drug trial is performed on individuals having a common tumor type. A tumor sample is taken concomitant to the drug trial. A subset of treated individuals respond positively to the treatment, but the treatment as a whole is not observed to have an efficacy sufficient to warrant development of the drug.

Samples of the treated population are subjected to shotgun genome sequencing. Short read sequence information is obtained, but no substantial genome structural information is obtained. Individual sequence information, such as single nucleotide polymorphism information, is not observed to correlate with treatment efficacy.

After a substantial passage of time, the samples are reassessed. Samples are subjected to nucleic acid protein complex excision such that complex integrity is preserved, and are subjected to analysis as disclosed herein.

Complexes are isolated, and exposed nucleic acid ends are ligated to form paired end fragments. The paired end fragments are isolated using a biotinylated base introduced at ligation sites.

Read pairs are sequenced to obtain sequence information on either side of ligation junctions. The read pair information is analyzed and a subset of the samples are observed to comprise genomic rearrangements not apparent from the shotgun sequencing analysis.

Drug response is reassessed in light of the genomic structural information, and it is observed that a particular rearrangement correlates with treatment efficacy. The genomic rearrangement correlating with treatment efficacy is developed as a marker to identify responders, and the drug is used in combination with a test for the marker to treat the disorder.

Example 14. Sequence-Free Rearrangement Detection

A paired end library is generated from a plurality of preserved samples. The library is probed using primers that anneal to regions of a genome that are known to be brought into phase during a genomic translocation implicated in cancer.

The library is observed to generate amplicons indicative of physical linkage among translocated segments with a higher frequency for a subset of samples. The libraries yielding amplicons are subjected to sequencing and paired end analysis, and are found to independently harbor translocations suspected of being implicated in cancer. The translocations are non-identical, and vary in location of orientation and proximity of the translocated segment, such that a direct PCR analysis of the genomes is unlikely to detect the majority of translocations. However, through ligated paired end library generation, oligonucleotide primers are effective in probing the samples for the presence of the translocation. This approach allows one to select libraries from a subset of samples for downstream sequence analysis, thereby preserving resources.

What is claimed is:

1. A method, comprising
   obtaining a formalin fixed paraffin-embedded (FFPE) sample from a subject, the FFPE sample comprising protein-DNA complexes;
   treating the FFPE sample with a proteinase to isolate nucleic acids such that the protein-DNA complexes are not destroyed, such that a first double-stranded segment and a second double-stranded segment are held together independent of a phosphodiester backbone, and such that the first double-stranded segment and the second double-stranded segment each have at least one exposed nucleic acid end; and
   deriving genomic structural information by analyzing nucleic acids of the protein-DNA complexes in the FFPE sample,
   wherein the treating the FFPE sample with the proteinase does not comprise overnight proteinase treatment.

2. The method of claim 1, wherein the FFPE sample is crosslinked.

3. The method of claim 2, wherein the FFPE sample is crosslinked using at least one of a formaldehyde, a formalin, UV light, mitomycin C, nitrogen mustard, melphalan, 1,3-butadiene diepoxide, cis diaminedichloroplatinum(II), and cyclophosphamide.

4. The method of claim 1, wherein the FFPE sample maintains positional information as to nucleic acids within it.

5. The method of claim 1, wherein the genomic structural information is indicative of a structural variant comprising at least one of an inversion, an insertion, a deletion, a chromosomal translocation, a copy number variant, a loss of heterozygosity, or a gene fusion relative to a reference genome.

6. The method of claim 1, comprising deriving information indicative of phase status for the first double-stranded segment and the second double-stranded segment of the nucleic acids.

7. The method of claim 1, comprising tagging an exposed nucleic acid end of the first double-stranded segment and an exposed nucleic acid end of the second double-stranded segment so as to convey physical linkage information.

8. The method of claim 7, wherein the tagging comprises ligating an oligonucleotide to the exposed end of the first double-stranded segment of the FFPE sample such that the oligonucleotide conveys information indicative of genomic structural information.

9. The method of claim 7, wherein the tagging comprises ligating the exposed end of the first double-stranded segment to the exposed end of the second double-stranded segment to form a paired end molecule.

10. The method of claim 1, wherein the FFPE sample is treated by contacting the FFPE sample to at least one of xylene and ethanol.

11. The method of claim 1, wherein the FFPE sample is treated by contacting the FFPE sample to at least one of an anthranilate and a phosphanilate.

12. The method of claim 1, wherein the FFPE sample preserves positional information reflective of its configuration in a tissue.

13. The method of claim 1, wherein the FFPE sample is not homogenized prior to isolating nucleic acids.

14. The method of claim 1, wherein the FFPE sample is stored for at least one week prior to isolating nucleic acids.

15. The method of claim 1, wherein the FFPE sample is stored for at least 6 months prior to isolating nucleic acids.

16. The method of claim 1, wherein the FFPE sample is transported from a collection point prior to isolating nucleic acids.

17. The method of claim 1, wherein the treating the FFPE sample with the proteinase is conducted for a time not greater than 1 hour.

* * * * *